US006870043B2

(12) United States Patent
Xiang et al.

(10) Patent No.: US 6,870,043 B2
(45) Date of Patent: Mar. 22, 2005

(54) FULL-LENGTH GB VIRUS C (HEPATITIS G VIRUS) RNA TRANSCRIPTS ARE INFECTIOUS IN PRIMARY CD4 POSITIVE T CELLS

(75) Inventors: Jinhua Xiang, Iowa City, IA (US); Sabina Wünschmann, Coralville, IA (US); Warren Schmidt, Oxford, IA (US); Jack Stapleton, Iowa City, IA (US)

(73) Assignee: The University of Iowa Research Foundation, Iowa City, IA (US)

( * ) Notice: Subject to any disclaimer, the term of this patent is extended or adjusted under 35 U.S.C. 154(b) by 0 days.

(21) Appl. No.: 09/828,498

(22) Filed: Apr. 5, 2001

(65) Prior Publication Data

US 2003/0170870 A1 Sep. 11, 2003

Related U.S. Application Data

(60) Provisional application No. 60/253,390, filed on Nov. 27, 2000, and provisional application No. 60/195,597, filed on Apr. 6, 2000.

(51) Int. Cl.[7] .............................................. C07H 21/04

(52) U.S. Cl. ............................... 536/23.72; 424/189.1; 424/218.1; 435/69.1; 435/320.1; 536/23.1

(58) Field of Search .......................... 424/189.1, 218.1; 435/69.1, 320.1; 536/23.1, 23.72

(56) References Cited

U.S. PATENT DOCUMENTS

| | | | | |
|---|---|---|---|---|
| 5,620,896 A | | 4/1997 | Herrmann et al. | 435/320.1 |
| 5,766,840 A | | 6/1998 | Kim et al. | 435/5 |
| 5,766,916 A | | 6/1998 | Belyaev et al. | 435/219 |
| 5,824,507 A | | 10/1998 | Kim et al. | 435/69.3 |
| 5,849,532 A | | 12/1998 | Kim et al. | 435/69.3 |
| 5,856,134 A | | 1/1999 | Kim et al. | 435/69.3 |
| 5,859,230 A | | 1/1999 | Kim et al. | 536/24.33 |
| 5,874,563 A | | 2/1999 | Kim et al. | 536/23.72 |
| 5,958,895 A | | 9/1999 | Pachuk et al. | 514/44 |
| 6,004,799 A | | 12/1999 | Luciw et al. | 435/236 |
| 6,156,495 A | * | 12/2000 | Pilot-Matias et al. | 435/5 |

OTHER PUBLICATIONS

Pang et al. Development of dengue virus replicons expressing HIV–1 gp120 and other heterolgous genes: a potenial future too for dual vaccination against dengue virus and HIV. BMC Microbiology (2001) vol. 1, No. 28, pp. 1–9.*

Agnello, et al., "Hepatitis C virus and other Flaviviridae viruses enter cells via low density lipoprotein receptor," *PNAS*, 96(22):12766–12771, 1999.

Akiyoshi, et al., "Intraspousal Transmission of GB Virus C/Hepatitis G Virus in an Hepatitis C Virus Hyperendemic Area in Japan," *Am. J. Gastroenterol.*, 94(6):1627–1631, 1999.

Alter, et al., "Acute non–A–E Hepatitis in the United States and the Role of Hepatitis G Virus Infection," *N. Engl. J. Med.*, 336(11):741–746. 1997.

Alter, et al., "The Incidence of Transfusion–Associated Hepatitis G Virus Infection and Its Relation to Liver Disease," *N. Engl. J. Med.*, 336(11):747–754. 1997.

Asada, et al., "Human Herpesvirus 6 Infects Dendritic Cells and Suppresses Human Immunodeficiency Virus Type 1 Replication in Coinfected Cultures," *J.Virol.* 73(5):4019–4028, 1999.

Beard, et al., "An Infectious Molecular Clone of a Japanese Genotype 1b Hepatitis C Virus," *Hepatology*, 30(1):316–324, 1999.

Birkenmeyer, et al., "Isolation of a GB Virus–Related Genome From a Chimpanzee," *J. Med. Virol.*, 56:44–51, 1998.

Bukh, et al., "Experimental Infection of Chimpanzees with Hepatitis G Virus and Genetic Analysis of the Virus," *J. Inf. Dis.*, 177:855–862, 1998.

Bukh, et al., "Toward a Surrogate Model for Hepatitis C Virus: An Infectious Molecular Clone of the GB Virus–B Hepatitis Agent," *Virol.*, 262:470–478, 1999.

Cohen, et al., "Hepatitis A Virus cDNA and Its RNA Transcripts Are Infectious in Cell Culture," *J. Virol.*, 61(10):3035–3039, 1987.

Dawson, et al., "Prevalence Studies of GB Virus–C Infection Using Reverse Transcriptase–Polymerase Chain Reaction," *J. Med. Virol.*, 50:97–103, 1996.

de Martino, et al., "Hepatitis G Virus Infection in Human Immunodeficiency Virus Type 1–Infected Mothers and Their Children," *J. Infect. Dis.*, 178:862–865, 1998.

Deacon, et al., "Genomic Structures of an Attenuated Quasi Species of HIV–1 from a Blood Transfusion Donor and Recipients," *Science*, 270:988–991, 1995.

Dickens, et al., "GB Virus C, Hepatitis G Virus, or Human Orphan Flavivirus?" *Hepatology*, 25(5):1285–1286, 1997.

Easterbrook, "Long–term Non–Progression in HIV Infection: Definitions and Epidemiological Issues," *J.Infect,*. 38:71–73, 1999.

(List continued on next page.)

*Primary Examiner*—Ulrike Winkler
(74) *Attorney, Agent, or Firm*—Fulbright & Jaworski L.L.P.

(57) ABSTRACT

GB virus C (GBV-C or hepatitis G virus) is a recently described flavivirus that frequently leads to chronic viremia in humans. Although associated with acute post-transfusion hepatitis, it is not clear if GBV-C is pathogenic for humans. A full-length cDNA was constructed from the plasma of a person with chronic GBV-C viremia. Peripheral blood mononuclear cells (PBMCs) transfected with full-length RNA transcripts from this GBV-C clone resulted in viral replication, demonstrating an isolated infectious GBV-C nucleic acid molecule. In addition to composition involving an isolated infectious GBV-C nucleic acid molecule, the present invention concerns methods of inhibiting and treating HIV infections.

16 Claims, 19 Drawing Sheets

OTHER PUBLICATIONS

Elvander, et al., "An Experimental Study of a Concurrent Primary Infection with Bovine Respiratory Syncytial Virus (BRSV) and Bovine Viral Diarrhoea Virus (BVDV) in Calves," *Acta.Vet.Scand,*. 39:251–264, 1998.

Emerson, et al., "cDNA Clone of Hepatitis A Virus Encoding a Virulent Virus: Induction of Viral Hepatitis by Direct Nucleic Acid Transfection of Marmosets," *J. Virol.*, 66(11):6649–6654, 1992.

Feucht, et al., "Distribution of Hepatitis G Viremia and Antibody Response to Recombinant Proteins With Special Regard to Risk Factors in 709 Patients," *Hepatology*, 26(2):491–494, 1997.

Fogeda, et al.,. In Vitro Infection of Human Peripheral Blood Mononuclear Cells by GB Virus C/Hepatitis G Virus, *J. Virol.* 73(5):4052–4061, 1999.

Gale, Jr,. et al., "Control of PKR Protein Kinase by Hepatitis C Virus Nonstructural 5A Protein: Molecular Mechanisms of Kinase Regulation," *Mol.Cell.Biol.* 18(9):5208–5218, 1998.

Gutierrez, et al., "Seroprevalence of GB Virus C and Persistence of RNA and Antibody," *J. Med. Virol.*, 53:167–173, 1997.

Hong, et al., "Generation of Transmissible Hepatitis C Virions from a Molecular Clone in Chimpanzees," *Virology*, 256:36–44, 1999.

Huang, et al., "The role of a mutant CCR5 allele in HIV–1 transmission and disease progression," *Nature Med.*, 2:1240–1243, 1996.

Kolykhalov, et al., "Identification of a Highly Conserved Sequence Element at the 3' Terminus of Hepatitis C Virus Genome RNA," *J. Virol.*, 70(6):3363–3371, 1996.

Kolykhalov, et al., "Transmission of Hepatitis C by Intrahepatic Inoculation with Transcribed RNA," *Science*, 277:570–574, 1997.

Laskus, et al., "Detection of Hepatitis G Virus Replication Sites by Using Highly Strand–Specific Tth–Based Reverse Transcriptase PCR," *J. Virol.*, 72(4):3072–3075, 1998.

Leary, et al., "Sequence and Genomic Organization of GBV–C: A Novel Member of the Flaviviridae Associated With Human Non–A–E Hepatitis," *J. Med. Virol.*, 48:60–67, 1996.

Lefrère, et al., "Carriage of GB Virus C/Hepatitis G Virus RNA Is Associated with a Slower Immunologic, Virologic, and Clinical Progression of Human Immunodeficiency Virus Disease in Coinfected Persons," *J.Infect.Dis.*, 179:783–789, 1999.

Linnen, et al., "Molecular Cloning and Disease Association of Hepatitis G Virus: A Transfusion–Transmissible Agent," *Science*, 271:505–508, 1996.

Melvin, et al., "Biophysical characterization of GB virus C from human plasma," *J. Virol. Methods*, 71:147–157, 1998.

Nerurkar, et al., "High Prevalence of GB Virus C/Hepatitis G Virus Infection Among Homosexual Men Infected With Human Immunodeficiency Virus Type 1: Evidence for Sexual Transmission," *J. Med. Virol.*, 56:123–127, 1998.

Okamoto, et al., "The entire nucleotide sequences of two GB virus C/hepatitis G virus isolates of distinct genotypes from Japan," *J. Gen. Virol.*, 78:737–745. 1997.

Pessoa, et al., "Quantitation of Hepatitis G and C Viruses in the Liver: Evidence That Hepatitis G Virus Is Not Hepatotropic," *Hepatol* ., 27(3):877–880, 1998.

Pinto, et al., "Inhibition of Human Immunodeficiency Virus Type 1 Replication prior to Reverse Transcription by Influenza Virus Stimulation," *J.Virol.* 74(10):4505–4511, 2000.

Rinaldo, Jr. et al., "Fetal and Adult Bovine Interferon Production During Bovine Viral Diarrhea Virus Infection," *Infect.Immun.* 14(3):660–666, 1976.

Robertson, et al., "Classification, nomenclature, and database development for hepatitis C virus (HCV) and related viruses: proposals for standardization," *Arch. Virol.*, 143(12):2493–2503, 1998.

Rowland–Jones, "Long–term Non–progression in HIV Infection: Clinico pathological Issues," *J.Infect.*, 38:67–70, 1999.

Sabin, et al., "Effect of Coinfection With Hepatitis G Virus on HIV Disease Progression in Hemophilic Men," *J.Acquir-.Immun Defic.Syndr.*, 19:546–547, 1998.

Schmidt, et al., "Direct Detection of Hepatitis C Virus (HCV) RNA From Whole Blood, and Comparison With HCV RNA in Plasma and Peripheral Blood Monouclear Cells," *J. Med. Virol.*, 47:153–160, 1995.

Seipp, et al., "Hepatotropism of GB virus C (GBV–C): GBV–C replication in human hepatocytes and cells of human hepatoma cell lines," *J. Hepatol.*, 30:570–579, 1999.

Shimizu, "Replication of GB Virus C (Hepatitis G Virus) in Interferon–Resistant Daudi Cells," *J. Virol.*, 73(10):8411–8414, 1999.

Simons, et al., "Identification of two flavivirus–like genomes in the GB hepatitis agent," *Proc.Natl.Acad-.Sci.*USA 92:34013405, 1995.

Simons, et al., "Isolation of novel virus–like sequences associated with human hepatitis," *Nature Med.*, 1(6):564–569, 1995.

Simons, et al., "Translation Initiation in GB Viruses A and C: Evidence for Internal Ribosome Entry and Implications for Genome Organization," *J. Virol.*, 70(9):6126–6135, 1996.

Stapleton, et al., "Prospective Comparison of Whole–Blood– and Plasma–Based Hepatitis C Virus RNA Detection Systems: Improved Detection Using Whole Blood as the Source of Viral RNA," *J. Clin. Microbiol.*, 37(3):484–489, 1999.

Tacke, et al., "Humoral Immune Response to the E2 Protein of Hepatitis G Virus Is Associated With Long–Term Recovery From Infection and Reveals a High Frequency of Hepatitis G Virus Exposure Among Healthy Blood Donors," *Hepatol.*, 26(6):1626–1633, 1997.

Tanaka, et al., "Acute hepatitis caused by sexual or household transmission of GBV–C," *J. Hepatol.*, 27:1110–1112, 1997.

Taylor, et al., "Inhibition of the Interferon–Inducible Protein Kinase PKR by HCV E2 Protein," *Science*, 285:107–110, 1999.

Thomas, et al., "Association of Antibody to GB Virus C (Hepatitis G Virus) with Viral Clearance and Protection from Reinfection," *J.Infect.Dis.*, 177:539–542, 1998.

Toyoda, et al., "Comparison of Characteristics Between Patients With GB Virus C/Hepatitis G Virus (GBV–C/HGV) RNA and Those With GBV–C/HGV E2–Antibody in Patients With Hemophilia," *J.Med.Virol.*, 60:34–38, 2000.

Wu, et al., "Prevalence and Risk Factor Analysis of GBV–C/HGV Infection in Prostitutes," *J. Med. Virol.*, 52:83–85, 1997.

Wu, et al., "Promoter–Dependent Tissue–Specific Expressive Nature of Imprinting Gene, Insulin–like Growth Factor II, in Human Tissues," *Biochem. Biophys. Res. Commun.*, 233(1):221–6, 1997.

Wünschmann & Stapleton, "Fluorescence–Based Quantitative Methods for Detecting Human Immunodeficiency Virus Type 1–Induced Syncytia," *J.Clin.Microbiol.*, 38(8):3055–3060, 2000.

Wünschmann, et al., "Characterization of Hepatitis C Virus (HCV) and HCV E2 Interactions with CD81 and the Low–Density Lipoprotein Receptor," *J. Virol.*, 74(21):10055–10062, 2000.

Xiang, et al., "Characterization of Hepatitis G Virus (GB–C Virus) Particles: Evidence for a Nucleocapsid and Expression of Sequences Upstream of the E1 Protein," *J. Virol.*, 72(4):2738–2744, 1998.

Xiang, et al., "Full–Length GB Virus C (Hepatitis G Virus) RNA Transcripts Are Infectious in Primary CD4–Positive T Cells," *J. Virol.*, 74(19):9125–9133, 2000.

Xiang, et al., "Visualization and characterization of GB virus–C particles: evidence for a nucleocapsid," *J. Viral Hepat.*, 6(S1):16–22, 1999.

Yanagi, et al., "Transcripts from a single full–length cDNA clone of hepatitis C virus are infectious when directly transfected into the liver of a chimpanzee," *Proc. Nat'l. Acad. Sci.*, 94:8738–8743, 1997.

Yanagi, et al., "Transcripts of a Chimeric cDNA Clone of Hepatitis C Virus Genotype 1b Are Infectious in Vivo," *Virology*, 244:161–172, 1998.

* cited by examiner

FULL-LENGTH GB VIRUS C (HEPATITIS G VIRUS) RNA TRANSCRIPTS ARE INFECTIOUS IN PRIMARY CD4 POSITIVE T CELLS

This application claims priority to U.S. provisional patent application Ser. No. 60/253,390, filed Nov. 27, 2000, and U.S. provisional patent application Ser. No. 60/195,597, filed on Apr. 6, 2000, which are herein incorporated by reference.

The U.S. Government may own rights in this invention pursuant to grant number R01AA12671 from the National Institutes of Health and a merit grant awarded to Jack Stapleton from the Veterans Administration.

BACKGROUND OF THE INVENTION

I. Field of the Invention

The present invention relates generally to the fields of molecular biology and virology. More particularly, it concerns an infectious clone of GBV-C, which can be used in treatment of other related hepatitis viruses infections and HIV, as well as broader uses in therapeutic and preventative therapies.

II. Description of Related Art

A. GB Virus Type C

Hepatitis C virus (HCV) is responsible for causing hepatitis C, a disease that chronically affects approximately four million Americans, many of whom may develop liver disease. Hepatitis C annually accounts for as many as 1,000 liver transplants in the United States and between 8,000 and 10,000 deaths. There is no vaccine or preventative treatment against HCV infection and treatment regimens may cause unwanted side effects.

GB virus type C (GBV-C), also known as hepatitis G virus (HGV), is a recently described virus whose genomic organization and nucleotide sequence places it in the Flavivirus family (Robertson et al., 1998). It is the most closely related human virus to HCV (Leary et al., 1996; Linnen et al., 1996; Simons et al., 1995), a major, worldwide pathogen (Robertson et al., 1998). It has been suggested that these viruses should be classified together with non-human GB-hepatitis agents as the hepacivirus genus. Both GBV-C and HCV appear to utilize the LDL receptor for viral entry (Agnello et al., 1999). Thus, comparison of GBV-C and HCV may provide insight into the reasons why HCV does not appear to replicate as efficiently in cell culture as GBV-C, and why GBV-C is cleared more efficiently by the host immune response than HCV (Gutierrez et al., 1997; Thomas et al., 1998; Toyoda et al., 2000).

Although GBV-C was originally associated with post-transfusion hepatitis in humans (Linnen et al., 1996), subsequent epidemiological studies indicated that it does not cause acute or chronic hepatitis (Alter et al., 1997a; Alter et al., 1997b). In addition, experimental GBV-C infection of chimpanzees was not associated with acute hepatitis (Bukh et al., 1998).

Persistent GBV-C viremia (as detected by RT-PCR) is common, with 0.9% to 3% of healthy U.S. blood donors and approximately 20%–30% of patients with HCV infection persistently infected with GBV-C (Dawson et al., 1996; Feucht et al., 1997; Guitierrez et al., 1997; Simons et al., 1995a; Simons et al., 1995b; Tacke et al., 1997). Following infection, about 80% of people clear their viremia, concomitantly developing antibody to the GBV-C E2 protein (Feucht et al., 1997; Gutierrez et al., 1997; Thomas et al., 1998).

Thus, it is estimated that approximately 20% of infected people remain viremic for long periods of time. GBV-C appears to be transmitted primarily by parenteral exposure (Simons et al., 1995), although there are data suggesting that sexual and/or household transmission of GBV-C infection may occur (Akiyoshi et al., 1999; de Martino et al., 1998; Nerurkar et al., 1998; Tanaka et al., 1997; Wu et al., 1997).

B. GBV-C and HIV

Recently, GBV-C has been investigated in the context of HIV infection. The course of HIV-1 infection is extremely variable among infected individuals, although the reasons for this observation are incompletely understood. Individuals whose HIV disease progresses slowly are often called long-term non-progressors (LTNPs). The prevalence of LTNPs varies from 1% to 25% of infected people, depending upon the definition used (reviewed in Easterbrook, 1999). There are no specific clinical criteria for LTNP; however, non-progression generally implies the absence of HIV-related clinical disease 10 or more years following infection and an absolute CD4 count of ≧500 cells/$mm^3$ (Easterbrook, 1999). Evaluation of LTNP's has identified HIV isolates with deletions in key replicative genes (Deacon et al., 1995) and host genetic factors, including specific HLA haplotypes (reviewed in reference Rowland-Jones, 1999) or, in some individuals, polymorphisms that result in absent or reduced expression of HIV co-receptors (Huang et al., 1996). However, these findings are uncommon and thought to account for no more than one-third of LTNP's (Rowland-Jones, 1999).

Persistent GBV-C infection is common in humans, with infection rates of approximately 1.8% in healthy blood donors, 15% in HCV positive people (Dawson et al., 1996), and 35%–40% in HIV positive individuals. GBV-C infection can persist for decades in the absence of any clinical morbidity or mortality. Among immune-competent individuals, it is estimated that 60% to 75% of GBV-C-infected people clear the infection, concomitantly developing antibodies to the envelope glycoprotein E2 (Thomas et al., 1998). GBV-C has been propagated in cultures of peripheral blood mononuclear cells (PBMC's) (Fogeda et al., 1999).

In 1998, Toyoda et al. found that hemophiliacs co-infected with HIV and GBV-C (also known as hepatitis G virus, HGV, or GBVC-HGV) had a lower plasma HIV RNA concentration and a lower incidence of AIDS diagnoses compared to those infected with HIV alone (Toyoda et al., 1998), although the differences were not statistically significant. In contrast, Sabin and colleagues found an increased rate of AIDS and death in hemophiliacs "exposed" to GBV-C (Sabin et al., 1998) compared to non-exposed individuals. This study included HIV-positive subjects who were either GBV-C viremic as determined by detection of GBV-C RNA in plasma, or HIV-infected people who were not viremic but were anti-GBV-C E2 antibody-positive. Although the mortality rate was higher among the GBV-C "exposed" individuals, the results were not statistically significant. Looking at HIV-infected persons, Lefrere and colleagues reported a significant delay in the rate of CD4+ T cell decline, development of AIDS, and death in 23 HIV-positive individuals with GBV-C viremia compared to 72 HIV-infected people without GBV-C viremia (Lefrère et al., 1999). In this study, HIV-infected individuals who were also GBV-C-positive were compared to HIV-infected individuals who were GBV-C-negative. When these subjects were matched by age, sex, baseline HIV RNA load, and baseline CD4 T cell count, HIV disease progression appeared to be worse in GBV-C-negative subjects.

Human herpesvirus 6 suppresses HIV replication in CD4+ T cells and dendritic cells (Asada et al., 1999), and recently, Pinto et al. demonstrated induction of in vitro anti-HIV activity by influenza virus (Pinto et al., 2000). Pinto and colleagues demonstrated that this anti-HIV activity was inhibited in part by anti-interferon alpha (γ-IFN) antibodies. GBV-C and its close relative HCV are unusual among human RNA viruses in that they cause persistent infection without a DNA intermediate or known latent stage in their replication cycle. Although the mechanism by which GBV-C is able to persist in vivo is unknown, there are some suggestive data potentially explaining HCV persistence. Two HCV proteins (the envelope glycoprotein E2 and the nonstructural protein NS5a) interact and inhibit an interferon-induced, RNA dependent protein kinase (PKR) (Gale et al., 1998; Taylor et al., 1999). PKR is one of several enzymes induced by γ-IFN, and one of the activities of PKR is to inhibit viral protein synthesis. Since GBV-C and HCV contain numerous predicted stem-loop structures in their positive sense RNA genomes, and replicate via a negative sense RNA intermediate, both viruses would potentially induce -IFN in PBMC cultures by presenting double stranded RNA in the cytoplasm of the cell. There appears to be an animal model supportive of this hypothesis. Two reports suggest that bovine viral diarrhea virus (BVDV; a flavivirus related to GBV-C) induces γ-IFN in cattle (Rinaldo, et al., 1976), and BVDV infection ameliorates experimental bovine respiratory syncytial virus infection in calves (Elvander et al., 1998).

During progressive human immunodeficiency virus type 1 (HIV-1) infection, the virus-specific immune responses of an infected subject gradually deteriorate, leading to the development of acquired immunodeficiency syndrome (AIDS). Most infected patients do not exhibit overt clinical manifestations of the disease for six to ten years following initial infection, however, most individuals infected with HIV eventually die from conditions or infections that the individual's immune system is no longer equipped to fight. While treatment for AIDS has been forthcoming, no effective cure has been reported. Thus, preventative and treatment options against HIV infection and the development of AIDS remain highly desirable. Use of GBV-C is advantageous because of the relative innocuousness of the virus.

C. Infectious Nucleic Acids

Full length cDNAs or RNA transcripts of several RNA viruses including hepatitis A virus, GBV-B, and HCV are infectious in cell culture or animal inoculation studies (Beard et al., 1999; Bukh et al., 1999; Cohen et al., 1987; Emerson et al., 1992; Hong et al., 1999; Kolykhalov et al., 1997; Yanagi et al., 1997; Yanagi et al., 1998). These infectious clones are useful for genetic studies and allow a precise method for evaluating evolution of viruses that normally exist in molecular quasispecies. Although several infectious HCV clones have been described, all of these rely upon inoculation of transcribed RNA into susceptible primate species, and none were shown to be infectious in vitro (Beard et al., 1999; Hong et al., 1999; Kolykhalov et al., 1997; Yanagi et al., 1997; Yanagi et al., 1998). Thus, these HCV infectious clones have only limited application (Beard et al., 1999; Hong et al., 1999; Kolykhalov et al., 1997; Yanagi et al., 1997; Yanagi et al., 1998). As the most closely related human flavivirus to HCV, the construction of an infectious GBV-C cDNA clone that replicates in vitro would provide an important tool for studying human hepacivirus replication.

SUMMARY OF THE INVENTION

The compositions and methods of the present invention take advantage of the discovery of an isolated and purified nucleic acid molecule encoding an infectious GBV-C. "Isolated and purified" indicates the nucleic acid molecule is not part of an intact GBV-C virus. These nucleic acid molecules have been produced in the form of a DNA construct or expression construct, as well as an infectious full-length GBV-C RNA transcript expressed from the DNA construct (collectively referred to as "recombinant GBV-C"). A cDNA clone made from the full-length or a less-than full-length transcript is also contemplated within the scope of the invention. The full-length transcript is approximately 9.7 kilobases (kb) in length. A nucleic acid sequence of the entire GBV-C genome is represented by SEQ ID NO: 1, which corresponds to Genbank accession number AF121950 and is approximately 9.4 kb. The sequence is provided as a DNA sequence, however, it may also be an RNA sequence with the corresponding thymidines (T) being substituted with uracils (U). The protein sequence encoded by this nucleic acid sequence is represented in SEQ ID NO:2. While nucleic acid molecules comprising all of SEQ ID NO: 1 are contemplated, smaller transcripts and clones containing less than the full-length of GBV-C sequences are considered within the present invention; particularly useful are transcripts or clones containing less than the entire-GBV-C sequence but also capable of producing an infectious GBV-C virus particle. Such viral particles made by recombinant techniques would be considered "recombinant." Viruses isolated from serum, for example, whose genome has not been altered recombinantly are considered non-recombinant. While the present invention is directed at recombinant forms of GVB-C, in some methods of the invention, non-recombinant viruses may be used as recombinant viruses.

In some embodiments of the invention, infectious GBV-C nucleic acid molecules and GBV-C viral particles produced from these molecules contain heterologous nucleic acid sequences. These heterologous sequences encode non-GBV-C sequences. For example, the heterologous sequence could encode HCV sequences, such that a chimeric virus is produced. GBV-C can be used a viral vector to provide a cell with an exogenous nucleic acid sequence. Alternatively, the compositions of the invention may be used as a vaccine to evoke an immune response against either GBV-C or a polypeptide or polypeptides encoded by heterologous sequences in the GBV-C nucleic acid molecules. These heterologous sequences could encode any sequence with therapeutic, preventative, or diagnostic functions. They could encode for antisense sequences, ribozymes, peptides, or polypeptides. Furthermore, they could be derived from non-GBV-C viruses, prokaryotes, or eukaryotes, such as mammals, or even humans. Transcription of a heterologous sequence may be controlled by a regulatory region, such as a promoter and/or enhancer, that is from GBV-C or a heterologous region. In some cases, the control region may be endogenous to the host cell, or it may be the control region that is normally associated with the heterologous sequence. The promoter and enhancers for use with the present invention may be eukaryotic, such as from a mammal, or it may be prokaryotic, such as T3, T7, and Sp6, or viral. In a further embodiment, the infectious GBV-C nucleic acid molecule exhibits resistance to interferon.

The present invention is also directed at methods of preparing or producing an infectious GBV-C. In some embodiments, an infectious GBV-C is prepared by: incubating a nucleic acid molecule containing GBV-C sequence under conditions effective to allow transcription of at least a portion of the GBV-C sequence; collecting the RNA transcript, and providing the RNA transcripts to a cell. A cell, which can be a prokaryotic or eukaryotic cell, can be provided with the transcript by a number of ways, including transfection methods, which are well known to those of skill in the art. In other methods, the transfected cell is incubated in appropriate media with or without serum to allow the cell the live. In any of the methods of the present invention, the cell may be prokaryotic or eukaryotic; the cell may be a mammalian cell. In other examples, the cell is a lymphocyte, while in still further examples, the cell is a CD4+ lymphocyte cell. A lymphocyte cell may be a T cell or a B cell. In the methods of the present invention, after sufficient time to allow the virus to propagate has passed, the supernatant can be collected from the cell. Any of the compositions described above and herein may be used to prepare infectious GBV-C. Any and all progeny GBV-C particles produced using the method and compositions of the present invention are encompassed by the invention.

In further aspects of the present invention, methods of producing infectious GBV-C are provided. Such methods may be accomplished by providing to a cell any composition of the present invention such as an isolated and purified nucleic acid molecule encoding an infectious GBV-C, or a GBV-C produced from such a molecule. In some cases the molecule will further comprise a heterologous sequence, with or without a heterologous, exogenous, or endogenous promoter. This cell may then be incubated under conditions that will permit replication and/or integration of viral nucleic acid molecules encoding an infectious GBV-C. The transfected or infected cell will eventually produce viral particles that can be collected from the supernatant.

The methods of the present invention may also include the steps of taking the supernatant from an infected or transfected cell and contacting a second cell with the supernatant of the first infected or transfected cell; incubating the second cell under conditions to permit replication of a GBV-C viral genome; and collecting the supernatant from the second cell.

The invention includes methods of expressing a heterologous nucleic acid sequence by providing to a cell an isolated and purified nucleic acid molecule encoding an infectious GBV-C sequence and the heterologous nucleic acid sequence. These methods can be utilized in vitro or in vivo.

Because the compositions of the invention can comprise a heterologous sequence encoding a polypeptide, they can be used to produce an immune response as well as antibodies in a subject given these compositions. For example, methods of producing an immune response in a subject can be accomplished by administering to the subject an effective amount of an expression construct comprising GBV-C sequences and a heterologous nucleic acid sequence operably linked to a promoter, such that the heterologous nucleic acid sequence encodes a polypeptide that elicits an immune response against the polypeptide.

In other methods of the invention, HIV disease progression (AIDS) is inhibited in a subject infected with HIV. This can be accomplished by administering to the subject an effective amount of an isolated and purified nucleic acid molecule encoding an infectious GBV-C sequence. The nucleic acid molecule may be RNA or DNA, or it may be a virus produced by such an isolated and purified nucleic acid molecule. The molecule may also contain the sequence of SEQ ID NO:1, be 9.3–9.7 kb in length, or comprise a portion of SEQ ID NO:1. These methods may be implemented in conjunction with other AIDS treatments such as AZT, HAART, or at least one protease inhibitor. Alternatively, these methods can be used to prevent HIV infection in an uninfected subject as well. Such methods could be employed by administering an effective amount of an isolated and purified nucleic acid molecule encoding an infectious GBV-C to a subject. This could be used to prevent HIV infection of a person's CD4+ cell.

Other embodiments of the invention include methods of treating a subject infected with HIV comprising administering to a cell of the subject an effective amount of an infectious GBV-C comprising a heterologous nucleic acid sequence. The method may be practiced in vitro or in vivo. If cells are treated in vitro, they may then be placed in a subject. In some embodiments, a recombinant infectious GVB-C is employed, while in others non-recombinant GVB-C is employed.

Methods of treating a subject infected with HIV may be implemented according to the present invention by administering to the subject an effective amount of an expression construct comprising a GBV-C sequence, such that the subject is provided a therapeutic benefit. Other ways of practicing the treatment methods of the invention include administering to the subject other AIDS treatments before, after, or concurrently with the expression construct. In some embodiments, a cell infected with HIV is contacted with an isolated and purified nucleic acid molecule comprising a nucleic acid sequence of SEQ ID NO:1, such that all or part of a GBV-C polypeptide is expressed in the cell. The polypeptide may cause HIV replication to be inhibited. It is contemplated that the isolated and purified nucleic acid molecule may encode an infectious GBV-C and inhibit HIV replication in the HIV-infected cell. The cell may be in an animal, such as a human. It is further contemplated that the cell may be one typically infected by HIV such as a CD4+ cell. Traditional AIDS therapy such as AZT or a protease inhibitor or HAART may be implemented in combination with any of the treatment methods described herein.

In other embodiments, a subject may be evaluated for cytokine inductions. Cytokine levels in a subject may be assayed before and/or after exposure to an infectious GVB-C sequence. In some embodiments, IL-2, IL-1B, IL-8, or IL-15 may be assayed by techniques well known to those of skill in the art.

The cells of the various methods may be eukaryotic or prokaryotic. In some cases, the cells are mammalian. In other cases, the cells are lymphocytes or are PBMCs. Alternatively, the cells may be CD4+. In still further embodiments, the cell may be any cell that supports the infection and/or propagation of a GBV-C, such as HepG2, Daudi, MT-2, and PH5CH cells. Cells may also be sustained in culture or in an organism.

In any of the compositions or methods of the present invention, a heterologous sequence may be comprised within a nucleic acid molecule encoding GBV-C sequences. The heterologous sequence is any nucleic acid sequence that does not encode GBV-C sequences. It may encode more than one gene or regulatory region. A heterologous sequence may encode an untranslated RNA such as an antisense construct or ribozyme, or a polypeptide that has therapeutic, preventative, or diagnostic uses. It may also encode a selectable or screenable marker by itself or in conjunction with another heterologous coding region. The untranslated RNA or polypeptide may be derived from an eukaryote, prokaryote, or virus. Examples of RNA and polypeptides encoded by heterologous sequences are provided below, but the invention should not be limited to those examples.

It is also contemplated that the invention covers all subsequent generations of GBV-C produced using the compositions and methods of the present invention. For example, if an isolated and purified nucleic acid molecule encoding a GBV-C virus is introduced into a cell such that the cell produces infectious GBV-C particles (first generation), the invention covers not only the particles, but also the viruses produced from the first generation particles, which would include viruses from generations 2, 3, 4, 5, 6, 7, 8, 9, 10, 15, 20, and later.

In other embodiments of the invention, an effective amount of an infectious GVB-C may be administered to cells or a subject to induce expression of IL-2, IL-1B, IL-8, or IL-15. Alternatively, an effective amount of an infectious GBV-C may be administered to reduce or inhibit the expression of IL-13. It is contemplated that GBV-C may be administered to cells or a subject to alter the cytokines in FIG. 14 accordingly.

In some embodiments of the invention, an infectious GBV-C can be used to inhibit or prevent apoptosis in a cell. An effective amount of GBV-C may be administered to a cell in vitro or in vivo to prevent or delay apoptosis.

The use of the word "a" or "an" when used in conjunction with the term "comprising" in the claims and/or the specification may mean "one," but it is also consistent with the meaning of "one or more," "at least one," and "one or more than one." Furthermore, where multiple steps of a method of process are cited, it is understood that the steps are not required to be performed in the particular order recited unless one of skill in the art is not be able to practice the method in a different order.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1A:
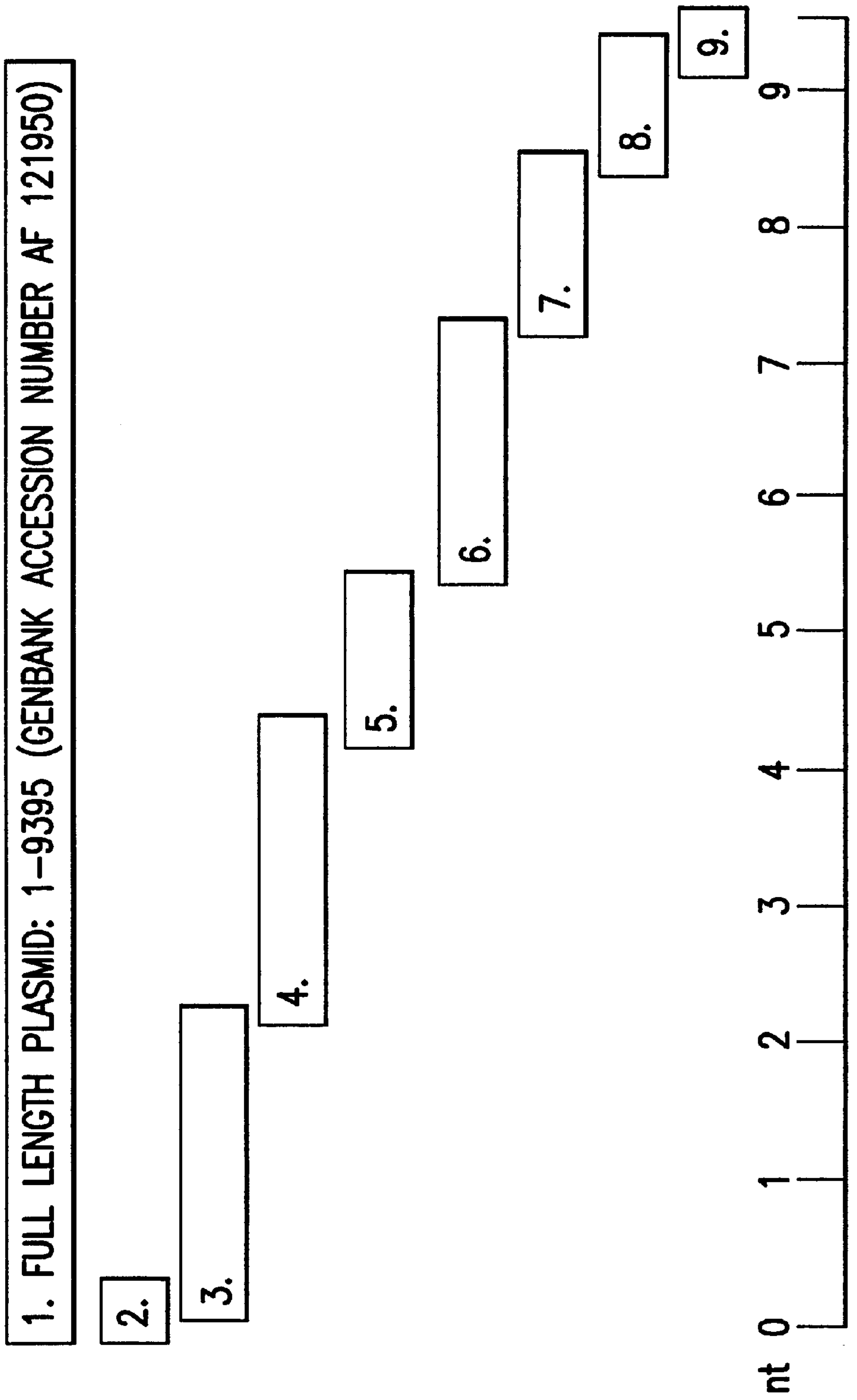
FIGS. 1A–B Cloning strategy for GBV-C full length clone. FIG. A. This schematically presents the full-length GBV-C cDNA sequences at the top. Each box beneath the full-length sequence represent the cDNAs amplified by RT-PCR used to make the full length clone. The 5' and 3' ends were generated using the RACE methods. The specific primer sets used for RT-PCR are shown in Table 4. FIG. B. This demonstrates RNA transcripts from GBV-C and HCV full-length cDNA. HCV and GBV-C RNA transcripts are indicated, and the RNA size marker is depicted.

Several full-length GBV-C sequences have been submitted to Genbank; however, the present invention provides a cDNA clone encoding a full-length GBV-C RNA transcripts that are infectious in peripheral blood mononuclear cell (PBMC) cultures. Unlike most previous full-length HCV constructions, the present invention is not a product of a consensus sequence, but instead, an authentic GBV-C sequence obtained from direct amplification of viral RNA. Replication was demonstrated by serial passage of culture supernatants, expression of the envelope glycoprotein E2, RNA replication (positive and negative strand RNA synthesis), and the detection of viral particles by sucrose gradient centrifugation and immune electron microscopy.

Thus, the present invention concerns the discovery of an infectious GBV-C clone. GBV-C is the most closely related virus to HCV, the cause of hepatitis C.

It was recently reported that GBV-C infection in HIV-infected patients correlates with a delayed onset of HIV (LeFrere et al., 1999); this report, however, is in conflict with a previous study (Sabin et al., 1998). Thus, the art at this time was confused about whether a correlation exists between onset of AIDS and GBV-C infection. Furthermore, any evidence that did exist was merely correlative; it did not involve evaluating whether GBV-C was involved in the observed delay of HIV. The experiments described herein also demonstrate a correlation. Unlike the previously reported studies, only subjects with viremia, as demonstrated by the detection of GBV-C RNA by RT-PCR, were evaluated; people with GBV-C anti-E2 antibody were not included. The studies disclosed herein also show that GBV-C inhibits HIV replication, but they significantly extend the observation of a correlation and provide a mechanism by which GBV-C delays the onset of HIV. Since this study employed an infectious GBV-C clone, they further indicate the advantage of the GBV-C clones of the present invention. Therefore, an infectious GBV-C of the present invention can be implemented in preventative or therapeutic treatments for HIV infection and the development of AIDS.

I. GBV-C

Like other members of the Flaviviridae, GBV-C is a positive-strand RNA virus that encodes a single long open reading frame (Leary et al., 1996). As discussed above, it does not cause acute or chronic hepatitis, yet it is the family member most closely related to HCV, the cause of hepatitis C. While sequences of GBV-C have been previously reported, for example in U.S. Pat. No. 5,874,563, which is specifically incorporated by reference, an infectious GBV-C clone has not been previously described.

The GBV-C polyprotein is predicted to be cleaved into two envelope proteins (E1 and E2), an RNA helicase, a trypsin-like serine protease, and an RNA-dependent RNA polymerase. A major difference between GBV-C and HCV is in the amino terminus of the polyprotein. In many isolates, this region is truncated, and no core (or nucleocapsid) protein is present (Simons et al., 1995; Xiang et al., 1999). In vitro translation experiments suggest that the AUG immediately upstream of the putative E1 protein is preferentially used to initiate translation, although there may be as many as four AUG's in frame with the polyprotein upstream of this AUG (Simons et al., 1996). In addition, the mutation frequency in codon position 1 and 2 of the region upstream of this AUG suggest that it is a non-coding region (Okamoto et al., 1997). These observations have led to speculation that GBV-C may not have a core protein or nucleocapsid (Dickens and Lenon, 1997; Simons et al., 1996). However, the inventors and others have shown that the sedimentation profiles of GBV-C particles are consistent with the presence of a nucleocapsid (Melvin et al., 2000; Xiang et al., 1998), and electron microscopy of plasma-derived GBV-C demonstrated enveloped particles with a nucleocapsid structure (Xiang et al., 1999). Although the amino acid composition of the nucleocapsid remains undefined, some infected individuals have antibody to a peptide representing amino acids upstream of the predicted E1 protein in frame with the polyprotein (Xiang et al., 1998). Thus, this region may encode the nucleocapsid.

Simons et al., 1996 demonstrated that the AUG codon at the amino terminus of putative El protein (AUG-554 in the isolate) was capable of initiating translation, whereas the upstream AUG's were not (Simons et al., 1996). In many isolates, the amino terminus of the predicted HGV polyprotein is truncated or absent (Leary et al., 1996; Linnen et al., 1996; Okamoto et al., 1997), and the frequency of polymorphisms in codon position 1 and 2 in the upstream ORF suggests that the region is not a coding region (Okamoto et al., 1997). Thus, it has been suggested that GBV-C may not have a core protein (Dickens and Lemon, 1997). It was previously shown that GBV-C particles have similar densities and sedimentation characteristics in sucrose and cesium chloride gradients as HCV (Xiang et al., 1998); subsequently particles of approximately 65 nm particle were shown with a 50 nm nucleocapsid structure (Xiang et al., 1999). In this study, two GBV-C particles types were identified with densities of 1.07 and 1.18 g/ml, consistent with virions and nucleocapsids respectively (Xiang et al., 1998). Furthermore, electron dense structures approximately 50–55 nm in size were visualized within the enveloped particle (FIG. 8). Thus the data support previous work identifying a nucleocapsid for GBV-C. The truncation of the polyprotein upstream of AUG-554 would be abolished if most isolates did not contain a single nucleotide deletion at position 381. Given the fact that all sequences produced thus far utilized nested RT-PCR, this may represent a polymerase artifact. Nevertheless, propagation of GBV-C in culture should allow the production of sufficient virus for ultimate characterization of the protein content of the GBV-C nucleocapsid. With the exception of the 5' ntr region, the remaining GBV-C sequences are highly conserved among geographically diverse isolates. Although there is less than 50% sequence homology in the 3' ntr region between GBV-C, GBV-B and HCV, the predicted secondary structures of these viruses bear striking similarities. GBV-C does not include a polypyrimidine tract, but does have three stem-loop structures at the extreme 3' end (FIG. 3). This indicates that the polypyrimidine regions of HCV and GBV-B are not requirements of hepacivirus replication.

The site of GBV-C replication has not been clearly identified, but it appears that replication in the hepatocyte, if it occurs, is not the primary source of virus in infected individuals (Laskus et al., 1998; Pessoa et al., 1998; Seipp et al., 1999). Recently, there were reports that human peripheral blood mononuclear cells (PBMC's) and interferon-resistant Daudi cells are permissive for GBV-C replication (Fogeda et al., 1999; Shimizu, 1999). In addition, transient replication of GBV-C was described in MT-2 cells (a human T-cell line), and PH5CH (a human hepatocyte line immortalized with simian virus 40 large T antigen) (Seipp et al., 1999).

A. Polynucleotides

1. Infectious GBV-C

The present invention concerns infectious GBV-C polynucleotides or nucleic acid molecules, isolatable and purifiable from GBV-C or mammalian cells infected with GBV-C, indicating they are free from total viral genomic RNA and proteins and are capable of infecting cells and propagating infectious GBV-C particles. It is contemplated that an isolated and purified infectious GBV-C nucleic acid molecule may take the form of RNA or DNA. An infectious GBV-C nucleic acid molecule refers to an RNA or DNA molecule that is capable of yielding an infectious GBV-C particle from a transfected cell.

As used herein, the term "RNA transcript" refers to an RNA molecule that has been isolated free of total genomic viral RNA and virus proteins and that is the product of transcription from a nucleic acid molecule for which at least one strand is DNA. A "full-length RNA transcript" refers to an RNA transcript that is full-length when compared to the genomic coding region, for example of GBV-C. Therefore, a full-length GBV-C RNA transcript encoding the GBV-C genome refers to an RNA segment that contains GBV-C sequences capable of producing an infectious GBV-C, yet is isolated away from, or purified free from, total GBV-C viral genomic RNA and GBV-C proteins. Such a full-length transcript may encode for one or more polypeptides, as well as contain regions controlling the regulation, e.g., transcription, translation, and RNA stability, of these polypeptides.

As used in this application, the term "polynucleotide" refers to a nucleic acid molecule, RNA or DNA, that has been isolated free of total genomic nucleic acid. Therefore, a "polynucleotide encoding an infectious GBV-C" refers to a nucleic acid segment that contains GBV-C coding sequences, yet is isolated away from, or purified and free of, total viral genomic RNA and proteins; similarly, a "polynucleotide encoding full-length GBV-C" refers to a nucleic acid segment that contains full-length GBV-C coding sequences yet is isolated away from, or purified and free of, total viral genomic RNA and protein. Therefore, when the present application refers to the function or activity of an infectious GBV-C that is encoded by a GBV-C polynucleotide, it is meant that the polynucleotide encodes a molecule that has the ability to propagate an infectious GBV-C virus particle from a cell. It is contemplated that an infectious GBV-C polynucleotide may refer to a GBV-C RNA transcript that is able to propagate an infectious GBV-C virus particle after introduction to a cell or to a GBV-C expression construct, clone, or vector composed of double-stranded DNA or DNA/RNA hybrid that is similarly capable.

The term "cDNA" is intended to refer to DNA prepared using RNA as a template. The advantage of using a cDNA, as opposed to genomic RNA or an RNA transcript is stability and the ability to manipulate the sequence using recombinant DNA technology (See Maniatis, 1989; Ausubel, 1994). There may be times when the full or partial genomic sequence is preferred. Alternatively, cDNAs may be advantageous because it represents coding regions of a polypeptide and eliminates introns and other regulatory regions.

It also is contemplated that a given GBV-C from a given cell may be represented by natural variants or strains that have slightly different nucleic acid sequences but, nonetheless, encode the same viral polypeptides (see Table 1 above). Consequently, the present invention also encompasses derivatives of GBV-C with minimal amino acid changes in its viral proteins, but that possess the same activities.

The term "gene" is used for simplicity to refer to a functional protein, polypeptide, or peptide-encoding unit. As will be understood by those in the art, this functional term includes genomic sequences, cDNA sequences, and smaller engineered gene segments that express, or may be adapted to express, proteins, polypeptides, domains, peptides, fusion proteins, and mutants. The nucleic acid molecule encoding GBV-C may contain a contiguous nucleic acid sequence encoding one or more GBV-C genes and regulatory regions and be of the following lengths: about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 441, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000 or more nucleotides, nucleosides, or base pairs. Such sequences may be identical or complementary to SEQ ID NO:1 or Genbank Accession number AF070476.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid segment as originally isolated, and does not exclude genes or coding regions later added to the segment by human manipulation.

In particular embodiments, the invention concerns isolated nucleic acid segments and recombinant vectors incorporating DNA sequences that encode GBV-C polypeptides or peptides that include within its amino acid sequence a contiguous amino acid sequence in accordance with, or essentially corresponding to GBV-C polypeptides.

In other embodiments, the invention concerns isolated nucleic acid segments and DNA recombinant vectors incorporating nucleic acid sequences that encode GBV-C polypeptides or peptides, particularly those necessary for infection, that include within its amino acid sequence a contiguous amino acid sequence in accordance with, or essentially corresponding to all strains of GBV-C polypeptides.

The nucleic acid segments used in the present invention, regardless of the length of the coding sequence itself, may be combined with other DNA or RNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol.

It is contemplated that the nucleic acid constructs of the present invention may encode full-length GBV-C or an infectious GBV-C, with or without heterologous sequences. A "heterologous" sequence refers to a sequence that is foreign or exogenous to the remaining sequence. A heterologous gene refers to a gene that is not found in nature adjacent to the sequences with which it is now placed.

In a non-limiting example, one or more nucleic acid constructs may be prepared that include a contiguous stretch of nucleotides identical to or complementary to GBV-C. A nucleic acid construct may be about 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 11,000, 12,000, 13,000, 14,000, 15,000, 20,000, 30,000, 50,000, 100,000, 250,000, about 500,000, 750,000, to about 1,000,000 nucleotides in length, as well as constructs of greater size, up to and including chromosomal sizes (including all intermediate lengths and intermediate ranges), given the advent of nucleic acids constructs such as a yeast artificial chromosome are known to those of ordinary skill in the art. It will be readily understood that "intermediate lengths" and "intermediate ranges," as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, about 97001, about 1,001, about 1002, about 50,001, about 50,002, about 750,001, about 750,002, about 1,000,001, about 1,000,002, etc. Non-limiting examples of intermediate ranges include about 3 to about 32, about 150 to about 500,001, about 3,032 to about 7,145, about 5,000 to about 15,000, about 20,007 to about 1,000,003, etc.

The nucleic acid segments used in the present invention encompass biologically functional equivalent GBV-C proteins and peptides. Such sequences may arise as a consequence of codon redundancy and functional equivalency that are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by human may be introduced through the application of site-directed mutagenesis techniques, e.g., to introduce improvements to the antigenicity of the protein or to test mutants in order to examine DNA binding activity at the molecular level.

2. Vectors Encoding Infectious GBV-C

The present invention encompasses the use of vectors to encode for an infectious GBV-C. The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Maniatis et al., 1988 and Ausubel et al., 1994, both incorporated herein by reference.

The term "expression vector" or "expression construct" refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra. It is contemplated that the infectious GBV-C particles of the present invention may arise from a vector containing GBV-C sequence or RNA encoding GBV-C sequence into a cell. Either of these, or any other nucleic acid molecules of the present invention may be constructed with any of the following nucleic acid control sequences. Thus, the full-length RNA transcript may contain the benefit of recombinant DNA technology such that it contains exogenous control sequences or genes.

a. Promoters and Enhancers

A "promoter" is a control sequence that is a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and/or expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. No. 4,683,202, U.S. Pat. No. 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the nucleic acid segment in the cell type, organelle, and organism chosen for expression. Those of skill in the art of molecular biology generally know the use of promoters, enhancers, and cell type combinations for protein expression, for example, see Sambrook et al. (1989), incorporated herein by reference. The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or exogenous, i.e., from a different source than GBV-C sequence. In some examples, a prokaryotic promoter is employed for use with in vitro transcription of a desired sequence. Prokaryotic promoters for use with many commercially available systems include T7, T3, and Sp6.

Table 1 lists several elements/promoters that may be employed, in the context of the present invention, to regulate the expression of a gene. This list is not intended to be exhaustive of all the possible elements involved in the promotion of expression but, merely, to be exemplary thereof. Table 2 provides examples of inducible elements, which are regions of a nucleic acid sequence that can be activated in response to a specific stimulus.

TABLE 1

Promoter and/or Enhancer

| Promoter/Enhancer | References |
|---|---|
| Immunoglobulin Heavy Chain | Banerji et al., 1983; Gilles et al., 1983; Grosschedl et al., 1985; Atchinson et al., 1986, 1987; Imler et al., 1987; Weinberger et al., 1984; Kiledjian et al., 1988; Porton et al., 1990 |
| Immunoglobulin Light Chain | Queen et al., 1983; Picard et al., 1984 |
| T-Cell Receptor | Luria et al., 1987; Winoto et al., 1989; Redondo et al.; 1990 |
| HLA DQ a and/or DQ β | Sullivan et al., 1987 |
| β-Interferon | Goodbourn et al., 1986; Fujita et al., 1987; Goodbourn et al., 1988 |
| Interleukin-2 | Greene et al., 1989 |
| Interleukin-2 Receptor | Greene et al., 1989; Lin et al., 1990 |
| MHC Class II 5 | Koch et al., 1989 |
| MHC Class II HLA-DRa | Sherman et al., 1989 |
| β-Actin | Kawamoto et al., 1988; Ng et al.; 1989 |
| Muscle Creatine Kinase (MCK) | Jaynes et al., 1988; Horlick et al., 1989; Johnson et al., 1989 |
| Prealbumin (Transthyretin) | Costa et al., 1988 |
| Elastase I | Omitz et al., 1987 |
| Metallothionein (MTII) | Karin et al., 1987; Culotta et al., 1989 |
| Collagenase | Pinkert et al., 1987; Angel et al., 1987 |
| Albumin | Pinkert et al., 1987; Tronche et al., 1989, 1990 |
| α-Fetoprotein | Godbout et al., 1988; Campere et al., 1989 |
| γ-Globin | Bodine et al., 1987; Perez-Stable et al., 1990 |
| β-Globin | Trudel et al., 1987 |
| c-fos | Cohen et al., 1987 |
| c-HA-ras | Triesman, 1986; Deschamps et al., 1985 |
| Insulin | Edlund et al., 1985 |
| Neural Cell Adhesion Molecule (NCAM) | Hirsh et al., 1990 |
| $\alpha_1$-Antitrypain | Latimer et al., 1990 |
| H2B (TH2B) Histone | Hwang et al., 1990 |
| Mouse and/or Type I Collagen | Ripe et al., 1989 |
| Glucose-Regulated Proteins (GRP94 and GRP78) | Chang et al., 1989 |
| Rat Growth Hormone | Larsen et al., 1986 |
| Human Serum Amyloid A (SAA) | Edbrooke et al., 1989 |
| Troponin I (TN I) | Yutzey et al., 1989 |
| Platelet-Derived Growth Factor (PDGF) | Pech et al., 1989 |
| Duchenne Muscular Dystrophy | Klamut et al., 1990 |
| SV40 | Banerji et al., 1981; Moreau et al., 1981; Sleigh et al., 1985; Firak et al., 1986; Herr et al., 1986; Imbra et al., 1986; Kadesch et al., 1986; Wang et al., 1986; Ondek et al., 1987; Kuhl et al., 1987; Schaffner et al., 1988 |
| Polyoma | Swartzendruber et al., 1975; Vasseur et al., 1980; Katinka et al., 1980, 1981; Tyndell et al., 1981; Dandolo et al., 1983; de Villiers et al., 1984; Hen et al., 1986; Satake et al., 1988; Campbell and/or Villarreal, 1988 |
| Retroviruses | Kriegler et al., 1982, 1983; Levinson et al., 1982; Kriegler et al., 1983, 1984a, b, 1988; Bosze et al., 1986; Miksicek et al., 1986; Celander et al., 1987; Thiesen et al., 1988; Celander et al., 1988; Chol et al., 1988; Reisman et al., 1989 |

TABLE 1-continued

| Promoter and/or Enhancer | |
|---|---|
| Promoter/Enhancer | References |
| Papilloma Virus | Campo et al., 1983; Lusky et al., 1983; Spandidos and/or Wilkie, 1983; Spalholz et al., 1985; Lusky et al., 1986; Cripe et al., 1987; Gloss et al., 1987; Hirochika et al., 1987; Stephens et al., 1987; Glue et al., 1988 |
| Hepatitis B Virus | Bulla et al., 1986; Jameel et al., 1986; Shaul et al., 1987; Spandau et al., 1988; Vannice et al., 1988 |
| Human Immunodeficiency Virus | Muesing et al., 1987; Hauber et al., 1988; Jakobovits et al., 1988; Feng et al., 1988; Takebe et al., 1988; Rosen et al., 1988; Berkhout et al., 1989; Laspia et al., 1989; Sharp et al., 1989; Braddock et al., 1989 |
| Cytomegalovirus (CMV) | Weber et al., 1984; Boshart et al., 1985; Foecking et al., 1986 |
| Gibbon Ape Leukemia Virus | Holbrook et al., 1987; Quinn et al., 1989 |

TABLE 2

| Inducible Elements | | |
|---|---|---|
| Element | Inducer | References |
| MT II | Phorbol Ester (TFA) Heavy metals | Palmiter et al., 1982; Haslinger et al., 1985; Searle et al., 1985; Stuart et al., 1985; Imagawa et al., 1987, Karin et al., 1987; Angel et al., 1987b; McNeall et al., 1989 |
| MMTV (mouse mammary tumor virus) | Glucocorticoids | Huang et al., 1981; Lee et al., 1981; Majors et al., 1983; Chandler et al., 1983; Lee et al., 1984; Ponta et al., 1985; Sakai et al., 1988 |
| β-Interferon | poly(rI)x poly(rc) | Tavernier et al., 1983 |
| Adenovirus 5 E2 | E1A | Imperiale et al., 1984 |
| Collagenase | Phorbol Ester (TPA) | Angel et al., 1987a |
| Stromelysin | Phorbol Ester (TPA) | Angel et al., 1987b |
| SV40 | Phorbol Ester (TPA) | Angel et al., 1987b |
| Murine MX Gene | Interferon, Newcastle Disease Virus | Hug et al., 1988 |
| GRP78 Gene | A23187 | Resendez et al., 1988 |
| α-2-Macroglobulin | IL-6 | Kunz et al., 1989 |
| Vimentin | Serum | Rittling et al., 1989 |
| MHC Class I Gene H-2κb | Interferon | Blanar et al., 1989 |
| HSP70 | E1A, SV40 Large T Antigen | Taylor et al., 1989, 1990a, 1990b |
| Proliferin | Phorbol Ester-TPA | Mordacq et al., 1989 |
| Tumor Necrosis Factor | PMA | Hensel et al., 1989 |
| Thyroid Stimulating Hormone α Gene | Thyroid Hormone | Chatterjee et al., 1989 |

The identity of tissue-specific promoters or elements, as well as assays to characterize their activity, is well known to those of skill in the art. Examples of such regions include the human LIMK2 gene (Nomoto et al. 1999), the somatostatin receptor 2 gene (Kraus et al., 1998), murine epididymal retinoic acid-binding gene (Lareyre et al., 1999), human CD4 (Zhao-Emonet et al., 1998), mouse alpha2 (XI) collagen (Tsumaki, et al., 1998), D1A dopamine receptor gene (Lee, et al., 1997), insulin-like growth factor II (Wu et al., 1997), human platelet endothelial cell adhesion molecule-1 (Almendro et al., 1996).

b. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

c. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

d. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression. (See Chandler et al., 1997, herein incorporated by reference.)

e. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and/or to minimize read through from the cassette into other sequences.

Terminators contemplated for use in the invention include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

f. Polyadenylation Signals

For expression, particularly eukaryotic expression, one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

g. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

h. Selectable and Screenable Markers

In certain embodiments of the invention, the cells containing a nucleic acid construct of the present invention may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformnants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

3. Host Cells

As used herein, the terms "cell," "cell line," and "cell culture" may be used interchangeably. All of these terms also include their progeny, which refers to any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

Characterization of PBMC subsets identified the CD4+ T cells as the cells supporting GBV-C replication. Although early studies suggested that GBV-C replicates in the liver, most reported studies indicate that GBV-C is not hepatotropic (Kiyosawa and Tanaka, 1999; Laskus et al., 1998). The inability to demonstrate infection of HepG2 cells is consistent with this, although the inventors were also unable to demonstrate persistent replication in the CD4+ T cell line (MOLT-4). Thus, host cell factors in primary cells may be necessary for replication. Studies are underway with primary hepatocyte cultures to test this hypothesis. Nevertheless, several studies have found GBV-C replication in PBMC's, and the concentration of virus in plasma relative to liver tissues suggests that the hepatocyte is not a prominent source of virus (Kobayashi et al., 1999). Taken together, these data suggest that GBV-C may be lymphotropic. As such, any lymphocyte-derived cell or cell line, particularly a CD4+ cell, is preferred for use with the present invention, however, any other cell line that permits transfection and/or propagation of an infectious GBV-C nucleic acid molecule is contemplated for use with the present invention. In other embodiments, the CD4+ cell may be infected with HIV, and such cells are contemplated to be targets for treatment to prevent or inhibit the progression of AIDS.

Nonetheless, host cells may be derived from prokaryotes or eukaryotes, depending upon whether the desired result is replication of the vector, expression of part or all of the vector-encoded nucleic acid sequences, or production of infectious viral particles. Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla). Alternatively, bacterial cells such as *E. coli* LE392 could be used as host cells for phage viruses.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either an eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

4. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROEN® and BACPACK™ BACULOVIRUS EXPRESSION SYSTEM from CLONTECH®.

Other examples of expression systems include STRATAGENE®'S COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. The Tet-On™ and Tet-Off™ systems from CLONTECH® can be used to regulate expression in a mammalian host using tetracycline or its derivatives. The implementation of these systems is described in Gossen et al., 1992 and Gossen et al., 1995, and U.S. Pat. No. 5,650,298, all of which are incorporated by reference.

INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

5. Non-Translated Nucleic Acid Sequences

In some embodiments of the present invention, a GBV-C clone or infectious GBV-C nucleic acid molecule encodes a heterologous nucleic acid sequence that is transcribed into RNA but that is not translated. Examples of this type of heterologous nucleic acid sequence include antisense molecules or sequences and ribozymes.

a. Antisense Constructs

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is altered.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences that are completely complementary will be sequences which are entirely complementary throughout their entire length and have no base mismatches. Other sequences with lower degrees of homology also are contemplated. For example, an antisense construct that has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

Particular oncogenes that are targets for antisense constructs are ras, myc, neu, raf, erb, src, fms, jun, trk, ret, hst, gsp, bcl-2, and abl. Also contemplated to be useful are anti-apoptotic genes and angiogenesis promoters. Other antisense constructs can be directed at genes encoding viral or microbial genes to reduce or eliminate pathogenicity, such as HCV or HIV genes. Specific constructs target genes such as viral env, pol, gag, rev, tat, taf or coat or capsid genes, or microbial endotoxin, recombination, replication, or transcription genes.

b. Ribozymes

Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme. Targets for this embodiment will include angiogenic genes such as VEGFs and angiopoietins as well as the oncogenes (e.g., ras, myc, neu, raf, erb, src, fms, jun, trk, ret, hst, gsp, bcl-2, EGFR, grb2 and abl). Other constructs will include overexpression of anti-apoptotic genes such as bcl-2, as well as microbial genes directed to viral or bacterial genes.

c. Other Heterologous Sequences

As the present invention is directed in some embodiments to the delivery of a sequence that is heterologous either to the virus or to a transduced cell, a variety of heterologous sequences are envisioned as part of the invention. Nucleic acid molecules that inhibit infection by non-GBV-C viruses are contemplated to be such sequences, for example, nucleotide inhibitors of HIV such as inhibitors of reverse transcriptase or integrase. In addition to encoding nucleic acid molecules, some embodiments of the invention concern the expression of a heterologous sequence as a polypeptide, and this would include proteinaceous inhibitors such as peptidic protease inhibitors, such as inhibitors of proteases associated with viral infection.

6. Introduction of Nucleic Acids into Cells

There are a number of ways in which nucleic acid molecules such as expression vectors may be introduced into cells. In certain embodiments of the invention, the expression vector comprises a GBV-C infectious particle or engineered vector derived from a GBV-C genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986). "Viral expression vector" is meant to include those vectors containing sequences of that virus sufficient to (a) support packaging of the vector and (b) to express a polynucleotide that has been cloned therein. In this context, expression may require that the gene product be synthesized. The present invention encompasses the use of an infectious GBV-C clone as a viral vector to transport and express a heterologous sequence in a host cell. Alternatively, a viral expression vector could be used to generate RNA transcripts encoding viral packing sequences and a heterologous gene, such that transfection of the transcripts into a host cell yield infectious viral particles containing the heterologous sequence.

A number of such viral vectors have already been thoroughly researched, including adenovirus, adeno-associated viruses, retroviruses, herpesviruses, and vaccinia viruses.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and also are required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses (HBV), new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991). A GBV-C viral vector may be constructed and propagated in a manner similar to HBV.

7. Methods of Gene Transfer

In order to effect expression of gene constructs, the expression vector or RNA transcripts must be delivered into a cell. This delivery may be accomplished in vitro, as in laboratory procedures for transforming cells lines, or in vivo or ex vivo, as in the treatment of certain disease states. One mechanism for delivery is via viral infection where the expression vector is encapsidated in an infectious viral particle. These methods are described above.

Several non-viral methods for the transfer of expression vectors into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression vector or RNA transcript has been delivered into the cell the nucleic acid encoding the gene of interest may be positioned and expressed at different sites. In certain embodiments, the nucleic acid encoding a gene or genes may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression vector is delivered to a cell and where in the cell the nucleic acid remains is dependent on the type of expression vector employed.

Transfer of a nucleic acid molecule may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest also may be transferred in a similar manner in vivo and express the gene product.

An embodiment of the claimed invention transfers RNA transcripts or a combination of transcripts into cells via perfusion. Continuous perfusion of an expression construct or a viral construct also is contemplated. The amount of construct or peptide delivered in continuous perfusion can be determined by the amount of uptake that is desirable. The present invention discloses an example of perfusion whereby a cell culture with an initial concentration of $10^6$ cells/ml can first be labeled, washed, and then incubated with 100 $\mu$g of isolated RNA for two hours.

In still another embodiment of the invention for transferring a nucleic acid molecule into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, nucleic acid encoding a particular gene such as GBV-C packing polypeptides may be delivered via this method and still be incorporated by the present invention.

In a further embodiment of the invention, the nucleic acid molecule may be entrapped in a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated are lipofectamine-nucleic acid complexes.

Liposome-mediated nucleic acid delivery and expression of foreign nucleic acid in vitro has been very successful. Wong et al., (1980) demonstrated the feasibility of liposome-mediated delivery and expression of foreign DNA in cultured chick embryo, HeLa and hepatoma cells. Nicolau et al., (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression vectors have been successfully employed in transfer and expression of nucleic acid in vitro and in vivo, then they are applicable for the present invention. Where a bacterial promoter is employed in the DNA vector, it also will be desirable to include within the liposome an appropriate bacterial polymerase.

Lipid based non-viral formulations provide an alternative to adenoviral gene therapies. Although many cell culture studies have documented lipid based non-viral gene transfer, systemic gene delivery via lipid based formulations has been limited. A major limitation of non-viral lipid based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in lipid vehicle stability in the presence and absence of serum proteins. The interaction between lipid vehicles and serum proteins has a dramatic impact on the stability characteristics of lipid vehicles (Yang and Huang, 1997). Cationic lipids attract and bind negatively charged serum proteins. Lipid vehicles associated with serum proteins are either dissolved or taken up by macrophages leading to their removal from circulation. Current in vivo lipid delivery methods use subcutaneous, intradermal, intratumoral, or intracranial injection to avoid the toxicity and stability problems associated with cationic lipids in the circulation. The interaction of lipid vehicles and plasma proteins is responsible for the disparity between the efficiency of in vitro (Felgner et al., 1987) and in vivo gene transfer (Zhu et al., 1993; Philip et al., 1993; Solodin et al., 1995; Liu et al., 1995; Thierry et al., 1995; Tsukamoto et al., 1995; Aksentijevich et al., 1996).

Recent advances in lipid formulations have improved the efficiency of gene transfer in vivo (Smyth-Templeton et al. 1997; WO 98/07408). A novel lipid formulation composed of an equimolar ratio of 1,2-bis(oleoyloxy)-3-(trimethyl ammonio)propane (DOTAP) and cholesterol significantly enhances systemic in vivo gene transfer, approximately 150 fold. The DOTAP:cholesterol lipid formulation is said to form a unique structure termed a "sandwich liposome". This formulation is reported to "sandwich" DNA between an invaginated bi-layer or 'vase' structure. Beneficial characteristics of these lipid structures include a positive ρ, colloidal stabilization by cholesterol, two dimensional DNA packing and increased serum stability.

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Lipid encapsulation has resulted in a lower toxicity and a longer serum half-life for such compounds (Gabizon et al., 1990). Numerous disease treatments are using lipid based gene transfer strategies to enhance conventional or establish novel therapies.

In certain embodiments of the invention, the lipid vehicle may be complexed with a hemagglutinating virus (HVJ). This has been shown to facilitate fusion with the cell membrane and promote cell entry of lipid-encapsulated DNA (Kaneda et al., 1989). In other embodiments, the lipid vehicle may be complexed or employed in conjunction with nuclear non-histone chromosomal proteins (HMG-1) (Kato et al., 1991). In yet further embodiments, the lipid vehicle may be complexed or employed in conjunction with both HVJ and HMG-1.

Protamine may also be used to form a complex with an expression construct. Such complexes may then be formulated with the lipid compositions described above for adminstration to a cell. Protamines are small highly basic nucleoproteins associated with DNA. Their use in the delivery of nucleic acids is described in U.S. Pat. No. 5,187,260, which is incorporated by reference.

Other expression vectors that can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). A synthetic neoglycoprotein, which recognizes the same receptor as ASOR, has been used as a gene delivery vehicle (Ferkol et al., 1993; Perales et al., 1994) and epidermal growth factor (EGF) also has been used to deliver genes to squamous carcinoma cells (Myers, EPO 0273085).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Continuous perfusion of an expression vector or a viral vector also is contemplated. The amount of vector or peptide delivered in continuous perfusion can be determined by the amount of uptake that is desirable.

Primary mammalian cell cultures may be prepared in various ways. In order for the cells to be kept viable while in vitro and in contact with the nucleic acid molecule, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

During in vitro culture conditions the expression construct may then deliver and express a nucleic acid encoding GBV-C proteins and/or a heterologous gene(s) into the cells. Finally, the cells may be reintroduced into the original animal, or administered into a distinct animal, in a pharmaceutically acceptable form by any of the means described below. Thus, providing an ex vivo method of treating a mammal with a pathologic condition is within the scope of the invention.

8. Nucleic Acid Detection

In addition to their use in yielding GBV-C proteins, polypeptides and/or peptides, the nucleic acid sequences disclosed herein have a variety of other uses. For example, they have utility as probes or primers for embodiments involving nucleic acid hybridization, such as sequence comparison and detection of infection.

a. Hybridization

The use of a probe or primer of between 13 and 100 nucleotides, preferably between 17 and 100 nucleotides in length, or in some aspects of the invention up to 1–2 kilobases or more in length, allows the formation of a duplex molecule that is both stable and selective. Molecules having complementary sequences over contiguous stretches greater than 20 bases in length are generally preferred, to increase stability and/or selectivity of the hybrid molecules obtained. One will generally prefer to design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

Accordingly, the nucleotide sequences of the invention may be used for their ability to selectively form duplex molecules with complementary stretches of DNAs and/or RNAs or to provide primers for amplification of DNA or RNA from samples. Depending on the application envisioned, one would desire to employ varying conditions of hybridization to achieve varying degrees of selectivity of the probe or primers for the target sequence.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

For certain applications, for example, site-directed mutagenesis, it is appreciated that lower stringency conditions are preferred. Under these conditions, hybridization may occur even though the sequences of the hybridizing strands are not perfectly complementary, but are mismatched at one or more positions. Conditions may be rendered less stringent by increasing salt concentration and/or decreasing temperature. For example, a medium stringency condition could be provided by about 0.1 to 0.25 M NaCl at temperatures of about 37° C. to about 55° C. while a low stringency condition could be provided by about 0.15 M to about 0.9 M salt, at temperatures ranging from about 20° C. to about 55° C. Hybridization conditions can be readily manipulated depending on the desired results.

In other embodiments, hybridization may be achieved under conditions of, for example, 50 mM Tris-HCl (pH 8.3), 75 mM KCl, 3 mM $MgCl_2$, 1.0 mM dithiothreitol, at temperatures between approximately 20° C. to about 37° C.

Other hybridization conditions utilized could include approximately 10 mM Tris-HCl (pH 8.3), 50 mM KCl, 1.5 mM $MgCl_2$, at temperatures ranging from approximately 40° C. to about 72° C.

In certain embodiments, it will be advantageous to employ nucleic acids of defined sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of being detected. In preferred embodiments, one may desire to employ a fluorescent label or an enzyme tag such as urease, alkaline phosphatase or peroxidase, instead of radioactive or other environmentally undesirable reagents. In the case of enzyme tags, colorimetric indicator substrates are known that can be employed to provide a detection means that is visibly or spectrophotometrically detectable, to identify specific hybridization with complementary nucleic acid containing samples.

In general, it is envisioned that the probes or primers described herein will be useful as reagents in solution hybridization, as in PCR™, for detection of expression of corresponding genes, as well as in embodiments employing a solid phase. In embodiments involving a solid phase, the test DNA (or RNA) is adsorbed or otherwise affixed to a selected matrix or surface. This fixed, single-stranded nucleic acid is then subjected to hybridization with selected probes under desired conditions. The conditions selected will depend on the particular circumstances (depending, for example, on the G+C content, type of target nucleic acid, source of nucleic acid, size of hybridization probe, etc.). Optimization of hybridization conditions for the particular application of interest is well known to those of skill in the art. After washing of the hybridized molecules to remove non-specifically bound probe molecules, hybridization is detected, and/or quantified, by determining the amount of bound label. Representative solid phase hybridization methods are disclosed in U.S. Pat. Nos. 5,843,663, 5,900,481 and 5,919,626. Other methods of hybridization that may be used in the practice of the present invention are disclosed in U.S. Pat. Nos. 5,849,481, 5,849,486 and 5,851,772. The relevant portions of these and other references identified in this section of the Specification are incorporated herein by reference.

b. Amplification of Nucleic Acids

Nucleic acids used as a template for amplification may be isolated from cells, tissues or other samples according to standard methodologies (Sambrook et al., 1989). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to GBV-C sequences are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids contain one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Affymax technology; Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1990, each of which is incorporated herein by reference in their entirety.

A reverse transcriptase PCR™ amplification procedure may be performed to quantify the amount of mRNA amplified. Methods of reverse transcribing RNA into cDNA are well known and described in Sambrook et al., 1989. Alternative methods for reverse transcription utilize thermostable DNA polymerases. These methods are described in WO 90/07641. Polymerase chain reaction methodologies are well known in the art. Representative methods of RT-PCR are described in U.S. Pat. No. 5,882,864.

Another method for amplification is ligase chain reaction ("LCR"), disclosed in European Application No. 320 308, incorporated herein by reference in its entirety. U.S. Pat. No. 4,883,750 describes a method similar to LCR for binding probe pairs to a target sequence. A method based on PCR™ and oligonucleotide ligase assay (OLA), disclosed in U.S. Pat. No. 5,912,148, may also be used.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Qbeta Replicase, described in PCT Application No. PCT/US87/00880, may also be used as an amplification method in the present invention. In this method, a replicative sequence of RNA that has a region complementary to that of a target is added to a sample in the presence of an RNA polymerase. The polymerase will copy the replicative sequence which may then be detected.

An isothermal amplification method, in which restriction endonucleases and ligases are used to achieve the amplification of target molecules that contain nucleotide 5'-[-alpha-thio]triphosphates in one strand of a restriction site may also be useful in the amplification of nucleic acids in the present invention (Walker et al., 1992). Strand Displacement Amplification (SDA), disclosed in U.S. Pat. No. 5,916,779, is another method of carrying out isothermal amplification of nucleic acids which involves multiple rounds of strand displacement and synthesis, i e., nick translation.

Other nucleic acid amplification procedures include transcription-based amplification systems (TAS), including nucleic acid sequence based amplification (NASBA) and 3SR (Kwoh et al., 1989; Gingeras et al., PCT Application WO 88/10315, incorporated herein by reference in their entirety). Davey et al., European Application No. 329 822 disclose a nucleic acid amplification process involving cyclically synthesizing single-stranded RNA ("ssRNA"), ssDNA, and double-stranded DNA (dsDNA), which may be used in accordance with the present invention.

Miller et al., PCT Application WO 89/06700 (incorporated herein by reference in its entirety) disclose a nucleic acid sequence amplification scheme based on the hybridization of a promoter region/primer sequence to a target single-stranded DNA ("ssDNA") followed by transcription of many RNA copies of the sequence. This scheme is not cyclic, i.e., new templates are not produced from the resultant RNA transcripts. Other amplification methods include "race" and "one-sided PCR" (Frohman, 1990; Ohara et al., 1989a).

c. Detection of Nucleic Acids

Following any amplification, it may be desirable to separate the amplification product from the template and/or the excess primer. In one embodiment, amplification products are separated by agarose, agarose-acrylamide or polyacrylamide gel electrophoresis using standard methods (Sambrook et al., 1989). Separated amplification products may be cut out and eluted from the gel for further manipulation. Using low melting point agarose gels, the separated band may be removed by heating the gel, followed by extraction of the nucleic acid.

Separation of nucleic acids may also be effected by chromatographic techniques known in art. There are many kinds of chromatography that may be used in the practice of the present invention, including adsorption, partition, ion-exchange, hydroxylapatite, molecular sieve, reverse-phase, column, paper, thin-layer, and gas chromatography as well as HPLC.

In certain embodiments, the amplification products are visualized. A typical visualization method involves staining of a gel with ethidium bromide and visualization of bands under UV light. Alternatively, if the amplification products are integrally labeled with radio- or fluorometrically-labeled nucleotides, the separated amplification products can be exposed to x-ray film or visualized under the appropriate excitatory spectra.

In one embodiment, following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, or another binding partner carrying a detectable moiety.

In particular embodiments, detection is by Southern blotting and hybridization with a labeled probe. The techniques involved in Southern blotting are well known to those of skill in the art. See Sambrook et al., 1989. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

Other methods of nucleic acid detection that may be used in the practice of the instant invention are disclosed in U.S. Pat. Nos. 5,840,873, 5,843,640, 5,843,651, 5,846,708, 5,846,717, 5,846,726, 5,846,729, 5,849,487, 5,853,990, 5,853,992, 5,853,993, 5,856,092, 5,861,244, 5,863,732, 5,863,753, 5,866,331, 5,905,024, 5,910,407, 5,912,124, 5,912,145, 5,919,630, 5,925,517, 5,928,862, 5,928,869, 5,929,227, 5,932,413 and 5,935,791, each of which is incorporated herein by reference.

d. Other Assays

Other methods for genetic screening may be used within the scope of the present invention, for example, to detect mutations in genomic DNA, cDNA and/or RNA samples. Methods used to detect point mutations include denaturing gradient gel electrophoresis ("DGGE"), restriction fragment length polymorphism analysis ("RFLP"), chemical or enzymatic cleavage methods, direct sequencing of target regions amplified by PCR™ (see above), single-strand conformation polymorphism analysis ("SSCP") and other methods well known in the art.

One method of screening for point mutations is based on RNase cleavage of base pair mismatches in RNA/DNA or RNA/RNA heteroduplexes. As used herein, the term "mismatch" is defined as a region of one or more unpaired or mispaired nucleotides in a double-stranded RNA/RNA, RNA/DNA or DNA/DNA molecule. This definition thus includes mismatches due to insertion/deletion mutations, as well as single or multiple base point mutations.

U.S. Pat. No. 4,946,773 describes an RNase A mismatch cleavage assay that involves annealing single-stranded DNA or RNA test samples to an RNA probe, and subsequent treatment of the nucleic acid duplexes with RNase A. For the detection of mismatches, the single-stranded products of the RNase A treatment, electrophoretically separated according to size, are compared to similarly treated control duplexes. Samples containing smaller fragments (cleavage products) not seen in the control duplex are scored as positive.

Other investigators have described the use of RNase I in mismatch assays. The use of RNase I for mismatch detection is described in literature from Promega Biotech. Promega markets a kit containing RNase I that is reported to cleave three out of four known mismatches. Others have described using the MutS protein or other DNA-repair enzymes for detection of single-base mismatches.

Alternative methods for detection of deletion, insertion or substitution mutations that may be used in the practice of the present invention are disclosed in U.S. Pat. Nos. 5,849,483, 5,851,770, 5,866,337, 5,925,525 and 5,928,870, each of which is incorporated herein by reference in its entirety.

B. Polypeptides

The present application is directed to the function or activity of an infectious GBV-C, which indicates it has the ability to propagate itself in a cell to produce an infectious GBV-C virus particle; expression of certain GBV-C polypeptides are required for virus activity, including replication, processing, and infection. The translated product of SEQ ID NO:1 is provided by SEQ ID NO:2. It is contemplated that the compositions and methods disclosed herein may be utilized to express part or all of SEQ ID NO:2. Determination of which molecules possess this ability may be achieved using functional assays measuring infectivity familiar to those of skill in the art. In other embodiments of the invention, heterologous polypeptides may be encoded by a sequence that also contains GBV-C sequences. "Heterologous" polypeptide indicates the polypeptide is not a GBV-C polypeptide. An endogenous GBV-C polypeptide refers to a polypeptide encoded by GBV-C viral RNA. Such a polypeptide would possess the same or similar sequence as SEQ ID NO:2.

1. Variants of Polypeptides

Amino acid sequence variants of the polypeptide can be substitutional, insertional or deletion variants. Deletion variants lack one or more residues of the native protein that are not essential for function or immunogenic activity, and are exemplified by the variants lacking a transmembrane sequence described above. Another common type of deletion variant is one lacking secretory signal sequences or signal sequences directing a protein to bind to a particular part of a cell. Insertional mutants typically involve the addition of material at a non-terminal point in the polypeptide. This may include the insertion of an immunoreactive epitope or simply a single residue. Terminal additions, called fusion proteins, are discussed below.

Substitutional variants typically contain the exchange of one amino acid for another at one or more sites within the protein, and may be designed to modulate one or more properties of the polypeptide, such as stability against proteolytic cleavage, without the loss of other functions or properties. Substitutions of this kind preferably are conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine.

The term "biologically functional equivalent" is well understood in the art and is further defined in detail herein. Accordingly, sequences that have between about 70% and about 80%; or more preferably, between about 81% and about 90%; or even more preferably, between about 91% and about 99%; of amino acids that are identical or functionally equivalent to the amino acids of GBV-C polypeptides, for example SEQ ID NO:2, provided the biological activity of the protein is maintained.

The term "functionally equivalent codon" is used herein to refer to codons that encode the same amino acid, such as the six codons for arginine or serine, and also refers to codons that encode biologically equivalent amino acids (see Table 3, below).

TABLE 3

CODON TABLE

| Amino Acids | | | Codons |
|---|---|---|---|
| Alanine | Ala | A | GGA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |

TABLE 3-continued

CODON TABLE

| Amino Acids | | | Codons |
|---|---|---|---|
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also will be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The following is a discussion based upon changing of the amino acids of a protein to create an equivalent, or even an improved, second-generation molecule. For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity, as discussed below. Table 3 shows the codons that encode particular amino acids.

In making such changes, the hydropathic index of amino acids may be considered. The importance of the hydropathic amino acid index in conferring interactive biologic function on a protein is generally understood in the art (Kyte & Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine *−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still produce a biologically equivalent and immunologically equivalent protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

2. Fusion Proteins

A specialized kind of insertional variant is the fusion protein. This molecule generally has all or a substantial portion of the native molecule, linked at the N- or C-terminus, to all or a portion of a second polypeptide. For example, fusions typically employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes such as a hydrolase, glycosylation domains, cellular targeting signals or transmembrane regions.

3. In Vitro Protein Production

Following transduction with a vector according to some embodiments of the present invention, primary mammalian cell cultures may be prepared in various ways. A host cell strain may be chosen that modulates the expression of the inserted sequences, or that modifies and processes the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production and/or presentation of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

A number of selection systems may be used including, but not limited to, HSV thymidine kinase, hypoxanthine-guanine phosphoribosyltransferase and adenine phosphoribosyltransferase genes, in tk-, hgprt- or aprt-cells, respectively. Also, anti-metabolite resistance can be used as the basis of selection: for dhfr, which confers resistance to; gpt, which confers resistance to mycophenolic acid; neo, which confers resistance to the aminoglycoside G418; and hygro, which confers resistance to hygromycin.

Animal cells can be propagated in vitro in two modes: as non-anchorage-dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established cell lines are the most widely used means of large scale production of cells and cell products. However, suspension cultured cells have limitations, such as tumorigenic potential and lower protein production than adherent cells.

4. Protein Purification

It may be desirable to purify GBV-C polypeptides, heterologous peptides and polypeptides, or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) is characterized by a very rapid separation with extraordinary resolution of peaks. This is achieved by the use of very fine particles and high pressure to maintain an adequate flow rate. Separation can be accomplished in a matter of minutes, or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (e.g., alter pH, ionic strength, and temperature.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand also should provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

II. Therapies

A. Treatment with a Heterologous Sequence

Some of the therapeutic embodiments contemplated by the present invention involve administering or supplying an infectious GBV-C nucleic acid molecule. Heterologous sequences, such as a gene or genes, may be included in the molecule such that these sequences are provided to and expressed within a cell via an infectious GBV-C virus, transcripts, or viral vector. The heterologous sequences may be from a prokaryote, eukaryote, or non-GBV-C virus. In some embodiments the infectious GBV-C nucleic acid molecule is employed simply as an effective vehicle for transporting heterologous sequences to a cell. In some cases, the heterologous gene is a wild-type copy, which will be provided to a cell lacking the wild-type gene. In addition to encoding non-expressed sequences such as ribozymes and antisense sequences, heterologous sequences could encode, but are not limited to, the following classes of gene products: cytokines, tumor suppressors, protein kinases, protein phosphorylases, proteases, protease inhibitors, receptors, transcription factors, ion channels, neurotransmitters, hormones and chemokines, toxins, transporters, ligands, cell cycle proteins, adhesion proteins, structural proteins, proteins involved in post-translational modification; chaperones; proteins that provokes an immune response (antigen); proteins involved in cell division; repair enzymes; proteins involved in replication, transcription, or translation; proteins involved in apoptosis; scavenger proteins; and housekeeping proteins. Some of these are discussed in more detail below. The compositions and methods of the present invention may be used with any of the genes or proteins, or with a combination of these genes and proteins, discussed elsewhere infra.

1. Tumor Suppressors p53 currently is recognized as a tumor suppressor gene. High levels of mutant p53 have been found in many cells transformed by chemical carcinogenesis, ultraviolet radiation, and several viruses. The p53 gene is a frequent target of mutational inactivation in a wide variety of human tumors and is already documented to be the most frequently-mutated gene in common human cancers. It is mutated in over 50% of human NSCLC (Hollstein et al., 1991) and in a wide spectrum of other tumors.

Wild-type p53 is recognized as an important growth regulator in many cell types. Missense mutations are common for the p53 gene and are essential for the transforming ability of the oncogene. A single genetic change prompted by point mutations can create carcinogenic p53, in as much as mutations in p53 are known to abrogate the tumor suppressor capability of wild-type p53. Casey and colleagues have reported that transfection of DNA encoding wild-type p53 into two human breast cancer cell lines restores growth suppression control in such cells (Casey et al., 1991). A similar effect also has been demonstrated on transfection of wild-type, but not mutant, p53 into human lung cancer cell lines (Takahasi et al., 1992). p53 appears dominant over the mutant gene and will select against proliferation when transfected into cells with the mutant gene. Normal expression of the transfected p53 does not affect the growth of normal or non-malignant cells with endogenous p53. Thus, such constructs might be taken up by normal cells without adverse effects. It is thus proposed that the treatment of p53-associated cancers with wild-type p53 will reduce the number of malignant cells or their growth rate.

The major transitions of the eukaryotic cell cycle are triggered by cyclin-dependent kinases, or CDK's. One CDK, cyclin-dependent kinase 4 (CDK4), regulates progression through the $G_1$. The activity of this enzyme may be to phosphorylate Rb at late $G_1$. The activity of CDK4 is controlled by an activating subunit, D-type cyclin, and by an inhibitory subunit $p16^{INK4}$. The $p16^{INK4}$ has been biochemically characterized as a protein that specifically binds to and inhibits CDK4, and thus may regulate Rb phosphorylation (Serrano et al., 1993; Serrano et al., 1995). Since the $p16^{INK4}$ protein is a CDK4inhibitor (Serrano, 1993), deletion of this gene may increase the activity of CDK4, resulting in hyperphosphorylation of the Rb protein. p16 also is known to regulate the function of CDK6.

$p16^{INK4}$ belongs to a newly described class of CDK-inhibitory proteins that also includes $p15^{INK4B}$, $p21^{WAF1}$, and $p27^{KIP1}$. The $p16^{INK4}$ gene maps to 9p21, a chromosome region frequently deleted in many tumor types. Homozygous deletions and mutations of the $p16^{INK4}$ gene are frequent in human tumor cell lines. This evidence suggests that the $p16^{INK4}$ gene is a tumor suppressor gene. This interpretation has been challenged, however, by the observation that the frequency of the $p16^{INK4}$ gene alterations is much lower in primary uncultured tumors than in cultured cell lines (Caldas et al., 1994; Cheng et al., 1994; Hussussian et al., 1994; Kamb et al., 1994; Kamb et al., 1994; Mori et al., 1994; Okamoto et al., 1994; Nobori et al., 1995; Orlow et al., 1994; Arap et al., 1995). However, it was later shown that while the p16 gene was intact in many primary tumors, there were other mechanisms that prevented p16 protein expression in a large percentage of some tumor types. p16 promoter hypermethylation is one of these mechanisms (Merlo et al., 1995; Herman, 1995; Gonzalez-Zulueta, 1995). Restoration of wild-type $p16^{INK4}$ function by transfection with a plasmid expression vector reduced colony formation by some human cancer cell lines (Okamoto, 1994; Arap, 1995). Delivery of p16 with adenovirus vectors inhibits proliferation of some human cancer lines and reduces the growth of human tumor xenografts.

C-CAM (designated 2 in Table 1) is expressed in virtually all epithelial cells (Odin and Obrink, 1987). C-CAM, with an apparent molecular weight of 105 kD, was originally isolated from the plasma membrane of the rat hepatocyte by its reaction with specific antibodies that neutralize cell aggregation (Obrink, 1991). Recent studies indicate that, structurally, C-CAM belongs to the immunoglobulin (Ig) superfamily and its sequence is highly homologous to carcinoembryonic antigen (CEA; designated 3 in Table 1) (Lin and Guidotti, 1989). Using a baculovirus expression system, Cheung et al. (1993) demonstrated that the first Ig domain of C-CAM is critical for cell adhesive activity.

Cell adhesion molecules, or CAM's are known to be involved in a complex network of molecular interactions that regulate organ development and cell differentiation (Edelman, 1985). Recent data indicate that aberrant expression of CAM's maybe involved in the tumorigenesis of several neoplasms; for example, decreased expression of E-cadherin, which is predominantly expressed in epithelial cells, is associated with the progression of several kinds of neoplasms (Edelman and Crossin, 1991; Frixen et al., 1991; Bussemakers et al., 1992; Matsura et al., 1992; Umbas et al., 1992). Also, Giancotti and Ruoslahti (1990) demonstrated that increasing expression of $\alpha_5\beta_1$ integrin by gene transfer can reduce tumorigenicity of Chinese hamster ovary cells in vivo. C-CAM now has been shown to suppress tumor growth in vitro and in vivo.

Other tumor suppressors that may be employed according to the present invention include p21, p15, BRCA1, BRCA2, IRF-1, PTEN (MMAC1), RB, APC, DCC, NF-1, NF-2, WT-1, MEN-I, MEN-II, zac1, p73, VHL, FCC, MCC, DBCCR1, DCP4, and p57.

2. Inducers of Apoptosis

Inducers of apoptosis, such as Bax, Bak, Bcl-$X_5$, Bad, Bim, Bik, Bid, Harakiri, E1B, Bad, ICE-CED3 proteases, TRAIL, SARP-2, and apoptin, similarly could find use according to the present invention.

3. Enzymes

Various enzyme genes are of interest according to the present invention. Such enzymes include cytosine deaminase, adenosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase, and human thymidine kinase, and extracellular proteins such as collagenase, matrix metalloprotease, RSKB, RSK1, RSK2, RSK3, thrombospondin, fibronectin, and plasminogen. In other embodiments of the present invention, the use of anti-angiogenic factors are contemplated.

4. Cytokines

Another class of genes that is contemplated to be inserted into the nucleic acid molecules of the present invention include interleukins and cytokines. Interleukin 1 (IL-1), IL-2, IL-3, IL-4, IL-5, IL-6, IL-7, IL-8, IL-9, IL-10, IL-11, IL-12, IL-13, IL-14, IL-15, β-interferon, α-interferon, γ-interferon, angiostatin, thrombospondin, endostatin, METH-1, METH-2, GM-CSF, G-CSF, M-CSF, and tumor necrosis factor.

5. Toxins

Various toxins are also contemplated to be useful as part of the expression vectors of the present invention, these toxins include bacterial toxins such as ricin A-chain (Burbage, 1997), diphtheria toxin A (Massuda et al., 1997; Lidor, 1997), pertussis toxin A subunit, *E. coli* enterotoxin toxin A subunit, cholera toxin A subunit, and pseudomonas toxin c-terminal. Recently, it was demonstrated that transfection of a plasmid containing the fusion protein regulatable diphtheria toxin A chain gene was cytotoxic for cancer cells. Thus, gene transfer of regulated toxin genes might also be applied to the treatment of cancers (Massuda et al., 1997).

6. Single Chain Antibodies

In yet another embodiment, one gene may comprise a single-chain antibody. Methods for the production of single-chain antibodies are well known to those of skill in the art. The skilled artisan is referred to U.S. Pat. No. 5,359,046, (incorporated herein by reference) for such methods. A single chain antibody is created by fusing together the variable domains of the heavy and light chains using a short peptide linker, thereby reconstituting an antigen binding site on a single molecule.

Single-chain antibody variable fragments (scFvs) in which the C-terminus of one variable domain is tethered to the N-terminus of the other via a 15 to 25 amino acid peptide or linker, have been developed without significantly disrupting antigen binding or specificity of the binding (Bedzyk et al., 1990; Chaudhary et al., 1990). These Fvs lack the constant regions (Fc) present in the heavy and light chains of the native antibody.

Antibodies to a wide variety of molecules are contemplated, such as oncogenes, growth factors, hormones, enzymes, transcription factors or receptors. Also contemplated are secreted antibodies, targeted to serum, against angiogenic factors (VEGF/VSP; βFGF; αFGF; and others) and endothelial antigens necessary for angiogenesis (i.e., V3 integrin). Specifically contemplated are growth factors such as transforming growth factor, and platelet derived growth factor (PDGF).

7. Transcription Factors and Regulators

Another class of genes that can be applied in an advantageous combination are transcription factors. Examples include C/EBPα, IκB, NFκB, Par-4, Sp1, TBP, TBP-binding proteins, and CREB.

8. Cell Cycle Regulators

Cell cycle regulators provide possible advantages, when combined with other genes. Such cell cycle regulators include p27, p16, p21, p57, p18, p73, p19, p15, E2F-1, E2F-2, E2F-3, p107, p130, and E2F-4. Other cell cycle regulators include anti-angiogenic proteins, such as soluble F1t1(dominant negative soluble VEGF receptor, soluble Wnt receptors, soluble Tie2/Tek receptor, soluble hemopexin domain of matrix metalloprotease 2, and soluble receptors of other angiogenic cytokines (e.g. VEGFR1/KDR, VEGFR3/F1t4-both VEGF receptors).

9. Chemokines

Genes that code for chemokines also may be used in the present invention. Chemokines generally act as chemoattractants to recruit immune effector cells to the site of chemokine expression. It may be advantageous to express a particular chemokine gene in combination with, for example, a cytokine gene, to enhance the recruitment of other immune system components to the site of treatment. Such chemokines include RANTES, MCAF, MIP 1-alpha, MIP 1-Beta, and IP-10. The skilled artisan will recognize that certain cytokines are also known to have chemoattractant effects and could also be classified under the term chemokines.

B. Treatment by Infection with GBV-C

In other embodiments, however, GBV-C infection comprises a therapeutic or preventative treatment for AIDS. As a therapeutic measure, an infectious GBV-C nucleic acid molecule can be used to reduce the severity or progression of AIDS, including the prevention of AIDS in HIV-infected individuals. A reduction in severity or progression of AIDS includes, but is not limited to prevention of or a reduction in the severity, duration, or discomfort associated with the following conditions: prolonged and unexplained fatigue; swollen glands; prolonged fever; chills; excessive sweating; swollen gums and mouth lesions; sore throat; cough; shortness of breath; constipation; diarrhea; symptoms of well-known opportunistic infections; Kaposi sarcomas; skin rashes or lesions; loss of appetite or weight loss; malaise; headaches; speech impairment; muscle atrophy; memory loss; reduced cognitive functioning; swelling of the joints; joint stiffness or pain; cold intolerance; pain or tenderness in bones; energy level; anxiety, stress, and tension; groin lump; pruritus; genital sores; blurred or decreased vision; diplopia; light sensitivity; pain in chest, sides, back, muscle or stomach; and seizures. As a preventative measure, infection of CD4+ T cells with GBV-C or a recombinant version of GBV-C can be used to inhibit infection of these cells by HIV. Alternatively, treatment with the GBV-C compositions of the present invention may effect a combination of preventative and therapeutic treatments insofar as infection of other cells in an HIV-infected subject's body is prevented.

Alternatively, inhibition of AIDS progression may be demonstrated by reduction of detectable HIV in the HIV-infected subject; maintaining a CD4 count above 200 for a longer than average period of time; maintaining a normal T cell count; or maintaining normal p24 antigen. The term "therapeutic benefit" used throughout this application refers to anything that promotes or enhances the well-being of the subject with respect to the medical treatment of his condition, which includes treatment of HIV-infection (before the onset of AIDS), AIDS, as well as treatment of Hepatitis C. A list of nonexhaustive examples of this includes extension of the subject's life by any period of time; decrease or delay in the progression of AIDS (HIV, as described above) or Hepatitis C; decrease in viral load of HIV or HCV; decrease in HIV replicationclearance of HIV or HCV viremiareduced transmission of HCV or HIV; decrease in liver damage or complications; and a decrease in pain to the subject that can be attributed to the subject's condition.

A. Pharmaceutical Compositions and Routes of Administration

The present invention contemplates infectious GBV-C nucleic acid molecules as well as infectious nucleic acid molecules encoding, in some embodiments, a heterologous sequence. In some embodiments, pharmaceutical compositions are administered to a subject. Different aspects of the present invention involve administering an effective amount of an aqueous composition. In another embodiment of the present invention, infectious GBV-C is administered to a subject to either prevent the infection by HIV or prevent the progression of HIV infection to development of AIDS. Additionally, such compounds can be administered in combination with treatment by HAART or by administration of AZT, or both. Though typically, infectious GBV-C will be administered separately from medication. Such compositions will generally be dissolved or dispersed in a pharmaceutically acceptable carrier or aqueous medium.

Those of skill in the art are well aware of how to apply gene delivery to in vivo and ex vivo situations. For viral vectors, one generally will prepare a viral vector stock. Depending on the kind of virus and the titer attainable, one will deliver 1 to 100, 10 to 50, 100–1000, or up to $1\times10^4$, $1\times10^5$, $1\times10^6$, $1\times10^7$, $1\times10^8$, $1\times10^9$, $1\times10^{10}$, $1\times10^{11}$, or $1\times10^{12}$ infectious particles to the patient. Similar figures may be extrapolated for liposomal or other non-viral formulations by comparing relative uptake efficiencies. Formulation as a pharmaceutically acceptable composition is discussed below.

The phrases "pharmaceutically acceptable" or "pharmacologically acceptable" refer to molecular entities and compositions that do not produce an adverse, allergic, or other untoward reaction when administered to an animal, or human, as appropriate. As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in the therapeutic compositions is contemplated. Supplementary active ingredients, such as other anti-cancer agents, can also be incorporated into the compositions.

In addition to the compounds formulated for parenteral administration, such as those for intravenous or intramuscular injection, other pharmaceutically acceptable forms include, e.g., tablets or other solids for oral administration; time release capsules; and any other form currently used, including cremes, lotions, mouthwashes, inhalants and the like.

The active compounds of the present invention can be formulated for parenteral administration, e.g., formulated for injection via the intravenous, intramuscular, intrathoracic, sub-cutaneous, or even intraperitoneal routes. Administration by i.v. or i.m. are specifically contemplated to achieve infection. The preparation of an aqueous composition that contains a compound or compounds that increase the expression of an MHC class I molecule will be known to those of skill in the art in light of the present disclosure. Typically, such compositions can be prepared as injectables, either as liquid solutions or suspensions; solid forms suitable for use to prepare solutions or suspensions upon the addition of a liquid prior to injection can also be prepared; and, the preparations can also be emulsified.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The active compounds may be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandolin, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier also can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques, which yield a powder of the active ingredient, plus any additional desired ingredient from a previously sterile-filtered solution thereof.

In certain cases, the therapeutic formulations of the invention also may be prepared in forms suitable for topical administration, such as in cremes and lotions. These forms may be used for treating skin-associated diseases, such as various sarcomas.

Administration of therapeutic compositions according to the present invention will be via any common route so long as the target tissue is available via that route. In cases where the present invention is used as a viral vector, a primary consideration will be the desired location for the heterologous sequences carried by the vector. Routes of administration include oral, nasal, buccal, rectal, vaginal or topical. For example, topical administration would be particularly advantageous for treatment of AIDS- or HCV-related skin conditions, or where a heterologous gene useful in treating a skin condition is carried by a viral vector. Alternatively, administration will be by orthotopic, intradermal subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery to the lung is contemplated. Volume of the aerosol is between about 0.01 ml and 0.5 ml. Similarly, a preferred method for treatment of colon-associated disease would be via enema. Volume of the enema is between about 1 ml and 100 ml. Direct intratumoral injection is the preferred mode, with continuous intratumoral perfusion a more specific embodiment.

In certain embodiments, it may be desirable to provide a continuous supply of therapeutic compositions to the patient. For intravenous or intraarterial routes, this is accomplished by drip system. For topical applications, repeated application would be employed. For various approaches, delayed release formulations could be used that provided limited but constant amounts of the therapeutic agent over and extended period of time. For internal application, continuous perfusion, for example with a GBV-C viral vector carrying a heterologous nucleic acid segment, of the region of interest may be preferred. This could be accomplished by catheterization, post-operatively in some cases, followed by continuous administration of the therapeutic agent. The time period for perfusion would be selected by the clinician for the particular patient and situation, but times could range from about 1–2 hours, to 2–6 hours, to about 6–10 hours, to about 10–24 hours, to about 1–2 days, to about 1–2 weeks or longer. Generally, the dose of the therapeutic composition via continuous perfusion will be equivalent to that given by single or multiple injections, adjusted for the period of time over which the injections are administered. It is believed that higher doses may be achieved via perfusion, however.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media that can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, Remington's Pharmaceutical Sciences, 1990). Some variation in dosage will necessarily occur depending on the condition of the subject being treated. The person responsible for administration will, in any event, determine the appropriate dose for the individual subject.

An effective amount of the therapeutic composition is determined based on the intended goal. The term "unit dose" or "dosage" refers to physically discrete units suitable for use in a subject, each unit containing a predetermined-quantity of the therapeutic composition calculated to produce the desired responses, discussed above, in association with its administration, i.e., the appropriate route and treatment regimen. The quantity to be administered, both according to number of treatments and unit dose, depends on the protection desired.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability, and toxicity of the particular therapeutic substance.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

As used herein, the term in vitro administration refers to manipulations performed on cells removed from an animal, including, but not limited to, cells in culture. The term ex vivo administration refers to cells that have been manipulated in vitro, and are subsequently administered to a living animal. The term in vivo administration includes all manipulations performed on cells within an animal.

In certain aspects of the present invention, the compositions may be administered either in vitro, ex vivo, or in vivo. In certain in vitro embodiments, transcribed RNA from a GBV-C clone is transfected into PBMC using DEAE-dextran. The transduced cells can then be used for in vitro analysis, or alternatively for in vivo administration.

U.S. Pat. Nos. 4,690,915, and 5,199,942, both incorporated herein by reference, disclose methods for ex vivo manipulation of blood mononuclear cells and bone marrow cells for use in therapeutic applications.

In vivo administration of the compositions of the present invention are also contemplated. Examples include, but are not limited to, transduction of bladder epithelium by administration of the transducing compositions of the present invention through intravesicle catheterization into the bladder (Bass, 1995), and transduction of liver cells by infusion of appropriate transducing compositions through the portal vein via a catheter (Bao, 1996). Additional examples include direct injection of tumors with the instant transducing compositions, and either intranasal or intratracheal (Dong, 1996) instillation of transducing compositions to effect transduction of lung cells.

1. Vaccines

The present invention includes methods for preventing the development of AIDS in both infected and uninfected persons, as well as the elicitation of an immune response to a heterologous polypeptide. As such, the invention contemplates vaccines for use in both active and passive immunization embodiments. Immunogenic compositions, proposed to be suitable for use as a vaccine, may be prepared most readily directly from infectious GBV-C nucleic acid molecules prepared in a manner disclosed herein. Preferably the antigenic material is extensively dialyzed to remove undesired small molecular weight molecules and/or lyophilized for more ready formulation into a desired vehicle.

The preparation of vaccines that contain GBV-C sequences as active ingredients is generally well understood in the art by analogy, as exemplified by U.S. Pat. Nos. 5,958,895, 6,004,799, and 5,620,896, all incorporated herein by reference. Typically, such vaccines are prepared as injectables either as liquid solutions or suspensions: solid forms suitable for solution in or suspension in liquid prior to injection may also be prepared. The preparation may also be emulsified. The active immunogenic ingredient is often mixed with excipients that are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants that enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1% to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10% to about 95% of active ingredient, preferably about 25% to about 70%.

The GBV-C infectious nucleic acids and GBV-C expressed heterologous proteins of the present invention may be formulated into the vaccine as neutral or salt forms. Pharmaceutically-acceptable salts include the acid addition salts (formed with the free amino groups of the peptide) and those that are formed with inorganic acids such as, for example, hydrochloric or phosphoric acids, or such organic acids as acetic, oxalic, tartaric, mandelin, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol(®) used as an about 0.25% solution, aggregation of the protein in the vaccine by heat treatment with temperatures ranging between about 70° to about 101° C. for a 30-second to 2-minute period, respectively. Aggregation by reactivating with pepsin-treated (Fab) antibodies to albumin, mixture with bacterial cells such as *C. parvum* or endotoxins or lipopolysaccharide components of Gram-negative bacteria, emulsion in physiologically acceptable oil vehicles such as mannide mono-oleate (Aracel A), or emulsion with a 20% solution of a perfluorocarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

2. Viruses as Therapeutic Compositions

The engineered viruses of the present invention may be administered directly into animals, or alternatively, administered to cells that are subsequently administered to animals. The viruses can be combined with the various β-interferon inhibiting formulations to produce transducing formulations with greater transduction efficiencies. A discussion of suitable viruses is presented above.

3. Treatment Additives a. Carrier Molecules

As is well known in the art, a given composition may vary in its immunogenicity. It is often necessary therefore to boost the host immune system, as may be achieved by coupling the heterologous polypeptide immunogen or GVH-C infectious nucleic acid to a carrier. Exemplary and preferred carriers are keyhole limpet hemocyanin (KLH) and bovine serum albumin (BSA). Other albumins such as ovalbumin, mouse serum albumin, or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde, and bis-biazotized benzidine.

b. Adjuvants

As is also well known in the art, the immunogenicity of a polypeptide or peptide composition can be enhanced by the use of non-specific stimulators of the immune response, known as adjuvants. Suitable adjuvants include all acceptable immunostimulatory compounds, such as cytokines, toxins, or synthetic compositions.

Adjuvants that may be used include IL-1, IL-2, IL-4, IL-7, IL-12, γ-interferon, GMCSP, BCG, aluminum hydroxide, MDP compounds, such as thur-MDP and nor-MDP, CGP (MTP-PE), lipid A, and monophosphoryl lipid A (MPL). RIBI, which contains three components extracted from bacteria, MPL, trehalose dimycolate (TDM) and cell wall skeleton (CWS) in a 2% squalene/Tween 80 emulsion. MHC antigens may even be used.

Exemplary, often preferred adjuvants include complete Freund's adjuvant (a non-specific stimulator of the immune response containing killed *Mycobacterium tuberculosis*), incomplete Freund's adjuvants and aluminum hydroxide adjuvant.

In addition to adjuvants, it may be desirable to coadminister biologic response modifiers (BRM), which have been shown to upregulate T cell immunity or downregulate suppresser cell activity. Such BRMs include, but are not limited to, Cimetidine (CIM; 1200 mg/d) (Smith/Kline, Pa.); or low-dose Cyclophosphamide (CYP; 300 mg/$m^2$) (Johnson/Mead, N.J.) and cytokines such as γ-interferon, IL-2, or IL-12 or genes encoding proteins involved in immune helper functions, such as B-7.

B. Combination Therapies

Of course it is understood that the method of the present invention, particularly administration of infectious GBV-C nucleic acid molecules as treatment for an HIV-infected subject, may also be used in combination with the administration of traditional therapies. Alternatively, the compositions of the present invention may be given in combination with treatment or prevention of hepatitis C, such as alpha interferon. Some such therapies are described below.

1. AZT

A well-known, traditional therapy for the treatment of AIDS involves zovidovudine (AZT™ available from Burroughs Wellcome). This is one of a class of nucleoside analogues known as dideoxynucleosides which block HIV replication by inhibiting HIV reverse transcriptase. The anti-AIDS drug zidovudine (also known as AZT) may also be used in limited circumstances, mostly in combination with rifampin, as described by Burger et al. (1993).

The compositions and methods disclosed herein will be particularly effective in conjunction with other forms of therapy, such as AZT and/or protease inhibitors that are designed to inhibit viral replication, by maintaining desirable levels of white blood cells. This, in effect, buys the patient the time necessary for the anti-viral therapies to work.

2. HAART

New combination drug therapy has shown promising results in the treatment of HIV-infected patients. Treatment with potent anti-HIV drug combinations is referred to as "highly active antiretroviral therapy" (HAART), and it has provided clinical improvement, longer survival, and improved quality of life for people infected with HIV during all four stages of HIV disease. Examples of HAART include a protease inhibitor (indinavir, nelfinavir, ritonavir, ritonavir/saquinavir, or saquinavir) combined with two nucleoside analogs (AZT/ddI, d4T/ddI, AZT/ddC, AZT/3TC, or d4T/3TC).

III. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

Isolation and Preparation of Cells

Peripheral blood mononuclear cells (PBMCs) from healthy blood donors (HCV RNA and antibody negative, HGV RNA negative, and HBV surface antigen negative) were isolated from heparinized blood by centrifugation on Ficoll-Hypaque gradients, washed twice with phosphate-buffered saline (PBS), and suspended in RPMI 1640 medium (Sigma, St. Louis, Mo.) supplemented with 10% fetal calf serum (FCS) and antibiotics as previously described (Cook et al., 1997). PBMC ($2\times10^6$ cells/ml) were maintained at 36° C. in 5% $CO_2$. Phytohemagglutinin (PHA, 10 $\mu$g/ml; DIFCO, Detroit, Mich.) and *Escherichia coli* lipopolysaccharide (LPS, 10$\mu$g/ml; Sigma) were added to the medium for 48 hours, following which, $10^7$ cells/ml were maintained in RPMI supplemented with 5% of interleukin-2 (IL-2) (Cellular Products Inc., Buffalo, N.Y.) and 5 $\mu$g/ml of PHA.

GBV-C RNA Preparation and RT-PCR

A previously described GBV-C RNA positive patient with a diagnosis of chronic liver disease was selected for this study (Xiang et al., 1998). This patient did not have detectable HCV antibody (Abbott EIA 2.0, North Chicago, Ill.) or RNA. RNA was prepared from plasma using a previously described guanidinium isothiocyanate (GITC) RNA extraction method (Schmidt et al., 1995). GBV-C RNA was detected using nested oligonucleotide primers from the 5' non-translated region as previously described (Xiang et al., 1998). Primers used for producing the full-length clone are described below. All RT-PCR reactions utilized MMLV RT (40 units) as previously described (Stapleton et al., 1999), followed by 35 cycles of PCR™ (94° C. for 30 s, 55° C. for 30 s, and 72° C. for 45 s). Three microliters of the first round served as the template for 35 cycles of second round PCR using nested primers and the same time and temperature settings (Schmidt et al., 1995).

Cloning and Sequencing of PCR™ Products

PCR™ products were separated by agarose gel electrophoresis, visualized by ethidium bromide staining, excised and purified using the Promega DNA purification system kit (Promega Co., Madison, Wis.). Amplicons were ligated into PCR™ 2.1 (Original TA Cloning® Kit, Invitrogen, Carlsbad, Calif.), and plasmid DNA was sequenced in both directions using primers complementary to the T7 polymerase or the M13 universal primer sequences present in the vector as previously described (Stampleton et al., 1999). Automated fluorescent dye terminator cycle sequencing was performed by the University of Iowa DNA Core Facility (Applied Biosystems automated DNA sequencer 373A, Foster City, Calif.).

Construction of Full-length GBV-C cDNA

Based on conserved sequences throughout the GBV-C genome, a series of primers were designed which contained suitable restriction sites in their overlapping sequences. Primer sets that generated products were used to prepare the full-length clone. FIG. 1 demonstrates the 6 primer sets and fragments generated in this study. The rapid amplification of cDNA ends (RACE) method was used to prepare the 5' and 3' terminal RNA (GIBCO BRL, Rockville, Md.). The eight DNA fragments were ligated into a full-length clone by using the restriction enzymes in either the overlapping sequences or in the vector DNA.

RNA Transcription and Transfection

10 $\mu$g GBV-C full-length DNA in pCR 2.1 was digested into linear DNA by Spe I and transcribed using T7 RNA polymerase (Promega) for 1 h at 37° C. An infectious HCV clone (Kolykhalov et al., 1997) was obtained (Genbank access # AF 009606). This clone was digested with Spe I, and RNA transcription was carried out in the same fashion. To eliminate plasmid DNA sequences, RQI Rnase-Free DNase (IU/$\mu$g) digestion of template DNA was completed for 15 min at 37° C. RNA transcripts were purified by chloroform extraction and ethanol precipitation. RNA from transcription reactions was denatured with formamide and formaldehyde, and analyzed on a 1% agarose-formaldehyde gel. Transcribed RNA in DEAE-dextran (1 mg/ml in HBSS) was added to washed PHA and LPS stimulated PBMC ($1\times10^6$), and the cells were incubated for 30 min at 36° C. in 5% $CO_2$ RPMI supplemented with 10% FCS was added, and the cells were incubated at 36° C. for 6 h with gentle rocking. After 6 h the medium was removed, the cells were washed twice, and incubated in RPM1 (10% FCS) at 36° C. in 5% $CO_2$. Fresh PHA, IL-2 stimulated donor cells were added each week to the cultured cells at a ratio of 4:1. After 4 weeks, cell culture supernatant from the transfected cells was used to inoculate fresh cells ($2\times10^6$/ml) for at least four consecutive passages.

Negative Strand GBV-C RT-PCR

For detection of GBV-C antisense RNA, cDNA synthesis was performed with an oligonucleotide primer containing a sequence unrelated to GBV-C (5'TCATGGTGGCGAAT AAAAGCCCCAGAAACCGACGCC 3', bold letters indicate non-GBV-C sequences), as described by others (Laskus et al., 1998). cDNA synthesis was stopped by heating at 99° C. for 1 h, and samples were treated with 50 $\mu$g/ml RNase A at 37° C. for 30 min. Subsequent amplification of plus-sense RNA by Taq polymerase used only the tag sequence (5'TCATGGTGGCGAATAA, Tag) for both first round of amplification and for the nested PCR™ reaction.

CD4 Staining and Flow Cytometry

Seventy two hours post infection, PMBC's ($2\times10^7$) were pelleted, resuspended in PBS containing 10% normal goat serum for 30 min at 4° C. prior to incubation with mouse anti-CD4 antibody (10 $\mu$g/ml, Molecular Probes) for 45 min at 4° C. Anti-CD4 binding was detected using Texas-Redconjugated goat anti-mouse antibody (10 μg/ml, Molecular Probes, Eugene, Oreg.) for 45 min at 4° C. Between each step, cells were washed two times with PBS. CD4 positive and CD4 negative cells were sorted by Flow Cytometry (FACScan, Becton Dickinson, San Jose, Calif.), and the two populations were collected for analysis.

Immunofluorescence

Indirect immunofluorescence was performed using a mouse monoclonal antibody against GBV-C E2 protein (Biodesign, Saco, Me.). Forty-eight hours post-infection, PBMCs were fixed with 10% formalin for 15 min, then permeabilized in acetone at −20° C. for 5 min. Following blocking with 10% normal goat sera, the cells were incubated for 1 hour at room temperature with the anti-GBV-C E2 antibody (10 μg/ml). After being washed, cells were incubated for 1 hour (5 μg/ml fluorescein Texas-red-labeled goat anti-mouse IgG, Molecular Probes). Images were recorded using confocal microscopy (519 nm, Zeiss, Jena, Germany) as previously described (Wünschmann and Stapleton, 2000).

Equilibrium Centrifugation in Sucrose

500 μl of either infected cell culture supernatant fluid or the infected cell lysates were layered onto 10 ml of a 20% to 60% sucrose gradient, and centrifugation was performed using a Beckman SW41 rotor at 156 000×g for 16 h at 4° C. as previously described (Xiang et al., 1999). Fourteen fractions (750 μl each) were collected, RNA extracted as above, and GBV-C RNA was detected by RT-PCR.

Immuno-electron Microscopy

Cell culture supernatants were collected 96 h post infection, and then concentrated by centrifugation at 80 000×g for 16 h at 4° C. in a SW 28 rotor (Beckman). The pellet was resuspended in 200 μl PBS. GBV-C E2 monoclonal antibody (5 μg/ml, Biodesign) was added to 50 μl of the virus pellet for 2 h at 37° C. Virus-IgG complexes were pelleted by centrifugation at 17,115×g for 15 min (Rotor 220.88 V01 Hermle). Gold-labeled goat anti-mouse monoclonal antibody (1:100 dilution, Aurlon, Netherlands) was used to detect GBV-C particles. The resuspended pellet was applied to a carbon coated copper grid, and was negatively stained with 1 uranyl acetate (pH 7.0). Particles were visualized by an H7000 Hitachi transmission electron microscope (75 V accelerating voltage).

Example 2

Construction of GBV-C Clone

To construct full-length GBV-C cDNA, nested RT-PCR was performed on plasma RNA obtained from a GBV-C infected individual using a variety of oligonucleotide sets spanning the entire genome. Six primer sets were identified which generated overlapping products containing restriction sites useful for ligation (Table 4). These six fragments started at nucleotide 25 and ended at nucleotide 9340. To identify the 5' and 3' ends of the genome, the 5' and 3' RACE methods were used. Primers used for these reactions were located from nt 284 to nt 305 (antisense) for 5' RACE and 9085 to 9106 (positive sense) for the 3' RACE. Each of these eight PCR™ amplification products was cloned into the pCR 2.1 vector and the nucleotide sequence was determined (FIG. 1A, Genbank access # AF 121950). Following ligation of the 8 fragments shown in FIG. 1A, a clone containing the full length GBV-C sequence of the GBV-C isolate was obtained. All cloning sites were again sequenced to exclude the possibility of cloning artifacts. Restriction digests of this full-length cDNA in the pCR 2.1 vector were consistent with the sequence data.

TABLE 4

Synthetic Oligonucleotide Primers Used to Construct a Full-Length GBV-C cDNA

| Clone | POSITIVE SENSE | | NEGATIVE SENSE | |
|---|---|---|---|---|
| Number | Outer | Inner | Outer | INNER |
| 2 | NA | NA | NA | 284–305* |
| 3 | 25–45 | 66–87 | 2550–2572 | 2543–2564 |
| 4 | 2224–2245 | 2250–2271 | 4464–4485 | 4358–4379 |
| 5 | 4275–4296 | 4281–4302 | 5547–5568 | 5538–5559 |
| 6 | 5328–5349 | 5334–5355 | 7491–7512 | 7483–7504 |
| 7 | 7380–7401 | 7389–7410 | 8644–8665 | 8638–8659 |
| 8 | 8475–8496 | 8483–8504 | 9417–9438 | 9319–9340 |
| 9 | NA | 9085–9106* | NA | NA |

*The 5' and 3' ends were generated using the RACE method. The numbers represent the nucleotide sequence numbers based on this isolate (GenBank AF 121950).

Example 3

GBV-C Sequence Analysis and Comparison with GBV-B and HCV

Figure 2:
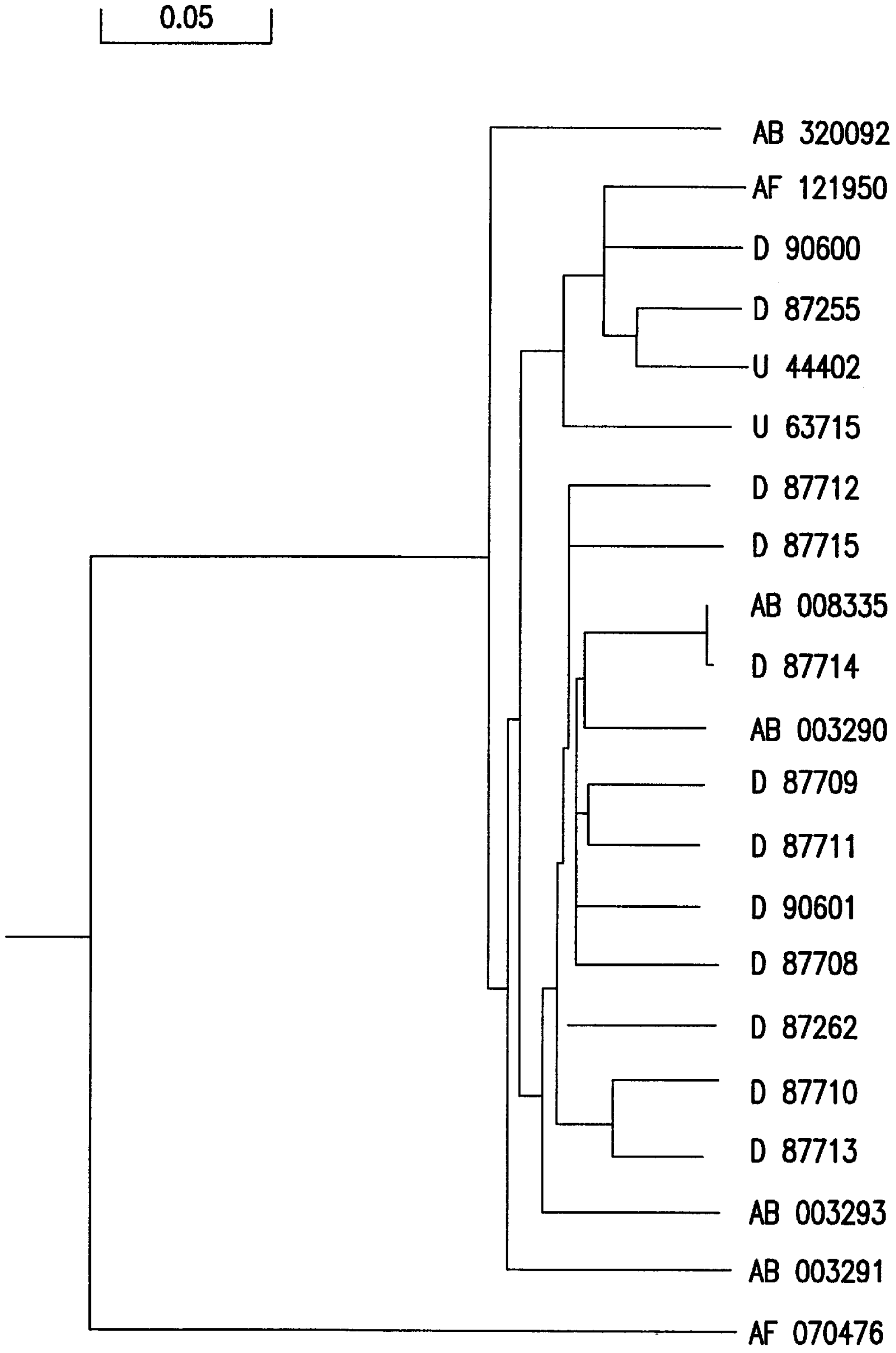
FIG. 2 Phylogenetic relationship between 20 full length human GBV-C isolates including the full-length clone described in this report (AF121950), and a chimpanzee full-length isolate (AF 070476) (Birkenmeyer et al., 1998). The GenBank accession number of each isolate is shown.

The GBV-C sequence the inventors obtained (AF121950) contained an open reading frame (ORF) beginning at nucleotide (nt) 351 and extending to nt 9080. This ORF is predicted to encode a 2910 amino acid long polyprotein with a molecular weight of 314,548 daltons. The complete GBV-C sequence of this isolate was compared with 19 additional human isolates and one chimpanzee isolate obtained by searching Genbank for complete GBV-C sequences. Nucleotide sequences were aligned, and the evolutionary distance between sequences was determined using the Jukes-Canter method (DNAMAN software; Lynnon BioSoft Inc, Quebec, Canada). Computed distances were used to construct phylogenetic trees by using the neighbor joining method (DNAMAN). FIG. 2 demonstrates that except for the chimpanzee isolate (AF 070476, GBV-Ctro) (6), there were close phylogenetic relationships between the isolate and all published GBV-C isolates. Twelve of these sequences contain the complete 5' ntr and 3' ntr. Comparison of these 12 revealed 92.79% homology at the nucleotide level. The isolate is most closely related to a Japanese isolate D 90600 (FIG. 2) (Okamoto et al., 1997). A list of the sequence accession numbers is displayed in FIG. 2.

Based on in vitro translation studies, the 5' nontranslated region (ntr) was shown to direct translation from the AUG starting at nt 554 of the isolate (Okamoto et al., 1997; Simons et al., 1996). There are three upstream AUG sequences in isolate AF 121950 that are in frame with the polyprotein, and 2 additional AUG's upstream of 554 which are not in frame. Thus, there are an additional 68 amino acids upstream of AUG-554 in the isolate. Fourteen of the 21 isolates studied provided complete 5' ntr sequence data. Comparison of potential translational start codons in frame with the polyprotem of these isolates revealed that 10 of the 14 contained only one AUG upstream of the AUG-554. This ORF would encode 31 amino acids upstream of the putative start site. Three of the 14 isolates had no AUG's upstream of AUG-554 in frame, although isolate D90600 had 5 AUG's in frame (which if translated, would encode 144 amino acids upstream of the proposed translational start site). The isolate and 3 additional isolates contained a single nt insertion at position 376 of the 5' ntr. If the remaining 10 isolates contained this insertion, all would include an in-frame AUG at position 381.

Evaluation of the predicted amino acid composition of the 21 GBV-C polyproteins intiating translation at 554 revealed them to be highly conserved with the exception of the chimpanzee isolate, AF 070476 (Birkenmeyer et al., 1998). The E1 and E2 coding regions displayed the most heterogeneity. The isolate (AF 121950) contained 9 amino acids that were not present in any of the complete sequences studied (E1: 117R. 122L; 127K; E2: 281 P; NS2: 157 1; NS3: 179K, 1848; NS5b: 2091, 522R). Comparison of the 20 human isolates for amino acid insertions and deletions revealed a single 12 amino acid insertion in the NS5a protein in isolate AB003291, and a single amino acid deletion found in NS5b of isolates D87710 and D87711. The chimpanzee isolate contained a 12 amino acid insertion in NS5a, which was very similar to the insertion in AB003291. In addition, the chimpanzee isolate contained a single amino acid insertion in E1 and E2 and several deletions that were not present in any of the human isolates (2 isolated deletions in E2, a 6 amino acid deletion in NS2, a 4 amino acid deletion in NS4, a 10 amino acid deletion in NS5a, a two amino acid deletion in NS5b, and a truncated carboxy-terminus with 15 amino acids fewer than AF121950 and 10 other isolates).

The complete 3' nontranslated region (ntr) from 11 of the 21 full-length isolates studied were available. There was 96.46% homology among these sequences, with AF121950 containing no unique nucleotide sequences. Of the 312 nucleotides present in the 3' ntr, there was only a single nt difference between AF121950 and D 90600. In both HCV and GBV-B, additional 3' ntr sequences were found at the 3' terminus subsequent to the original publication of the sequence (Bukh et al., 1999; Kolykhalov et al., 1996). Because of this, the inventors were concerned that there may be additional sequences on the 3' end of GBV-C. Consequently, the inventors performed 3' RACE studies eight times, and also carried out RT-PCR across 5'-to-3'-end-ligated viral RNA four times in an attempt to identify additional sequences downstream of the previously published 3' terminus. However, no additional nucleotide sequences were identified.

Figure 3A:
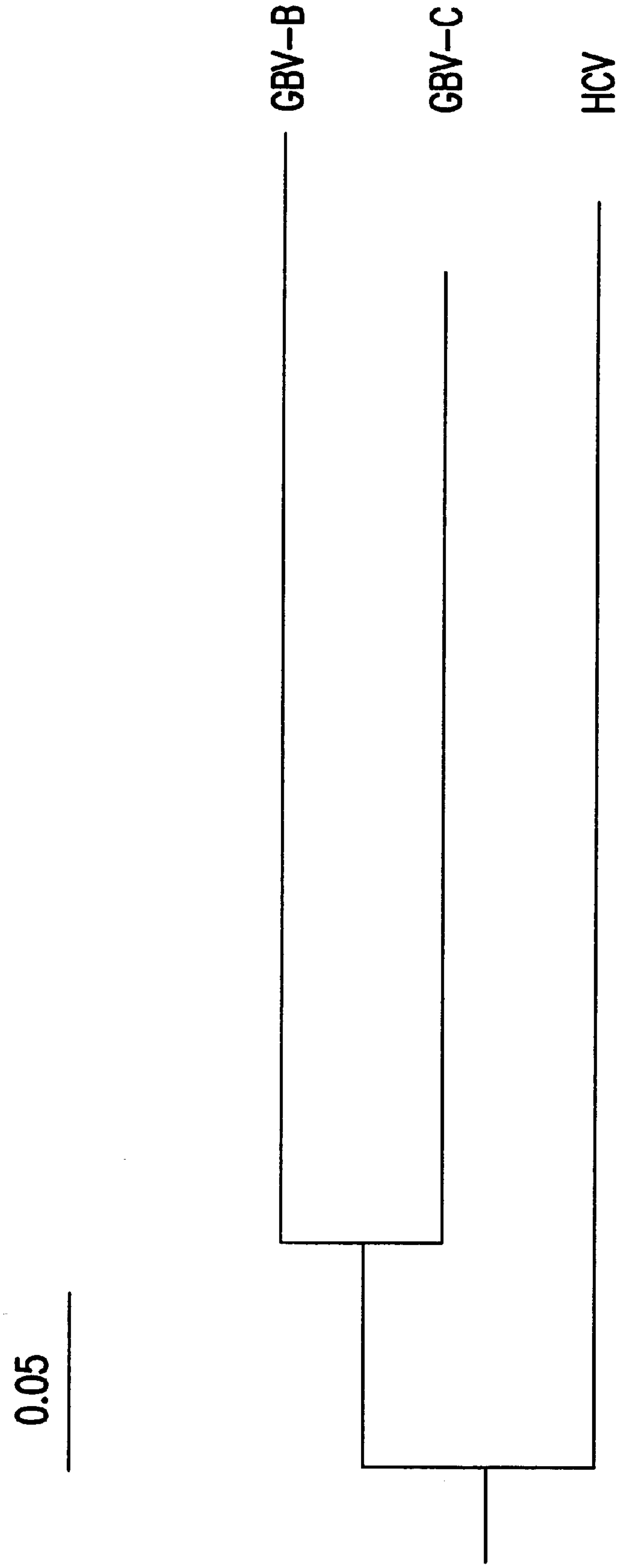
FIGS. 3A–D Phylogenetic relationship of the 3'ntr sequences of GBV-C, GBV-B and HCV (FIG. 3A). The predicted secondary structure of 3'ntr regions for GBV-C (FIG. 3B), GBV-B (FIG. 3C) and HCV (FIG. 3D) is shown.
Figure 3B:
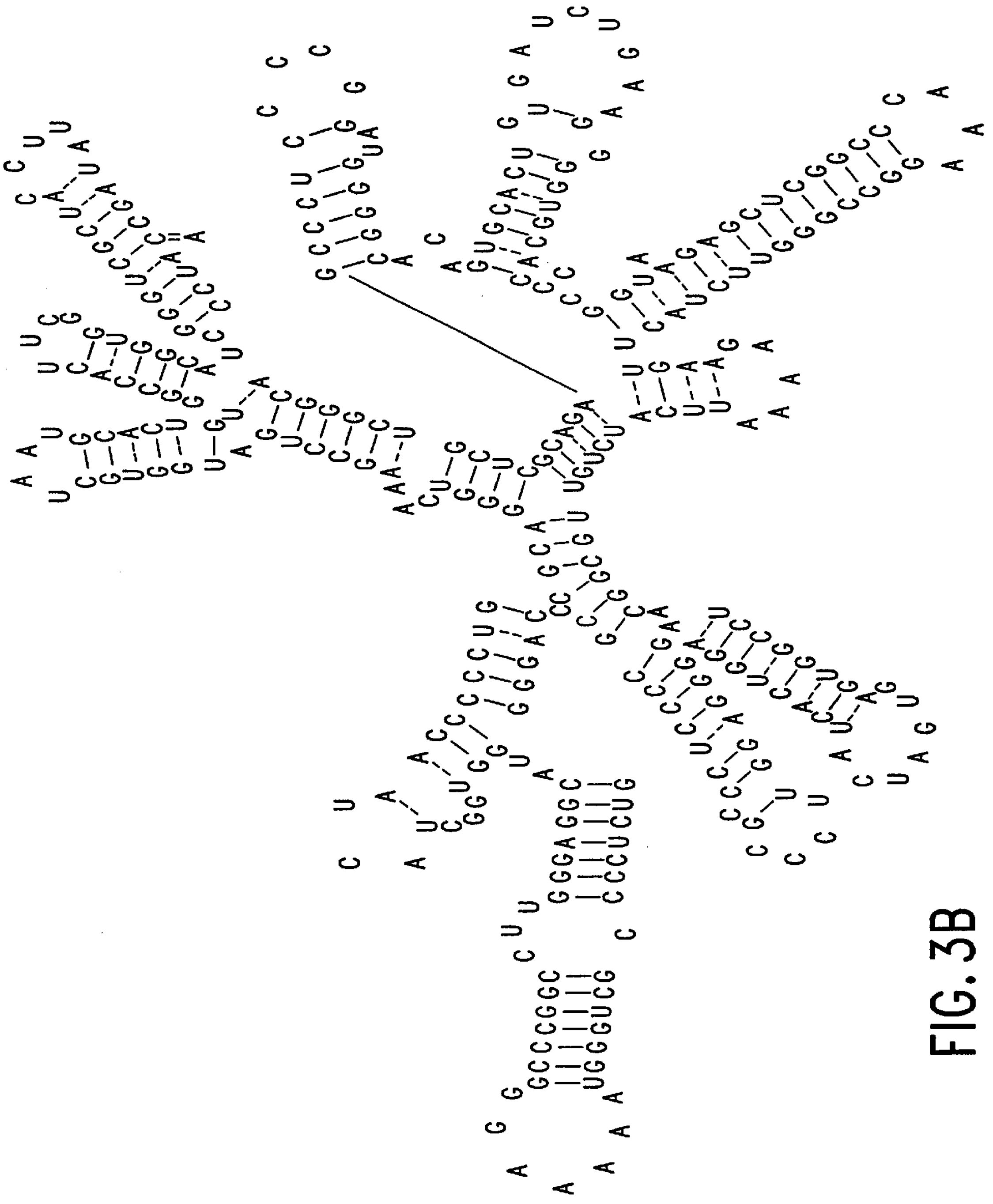
Figure 3C:
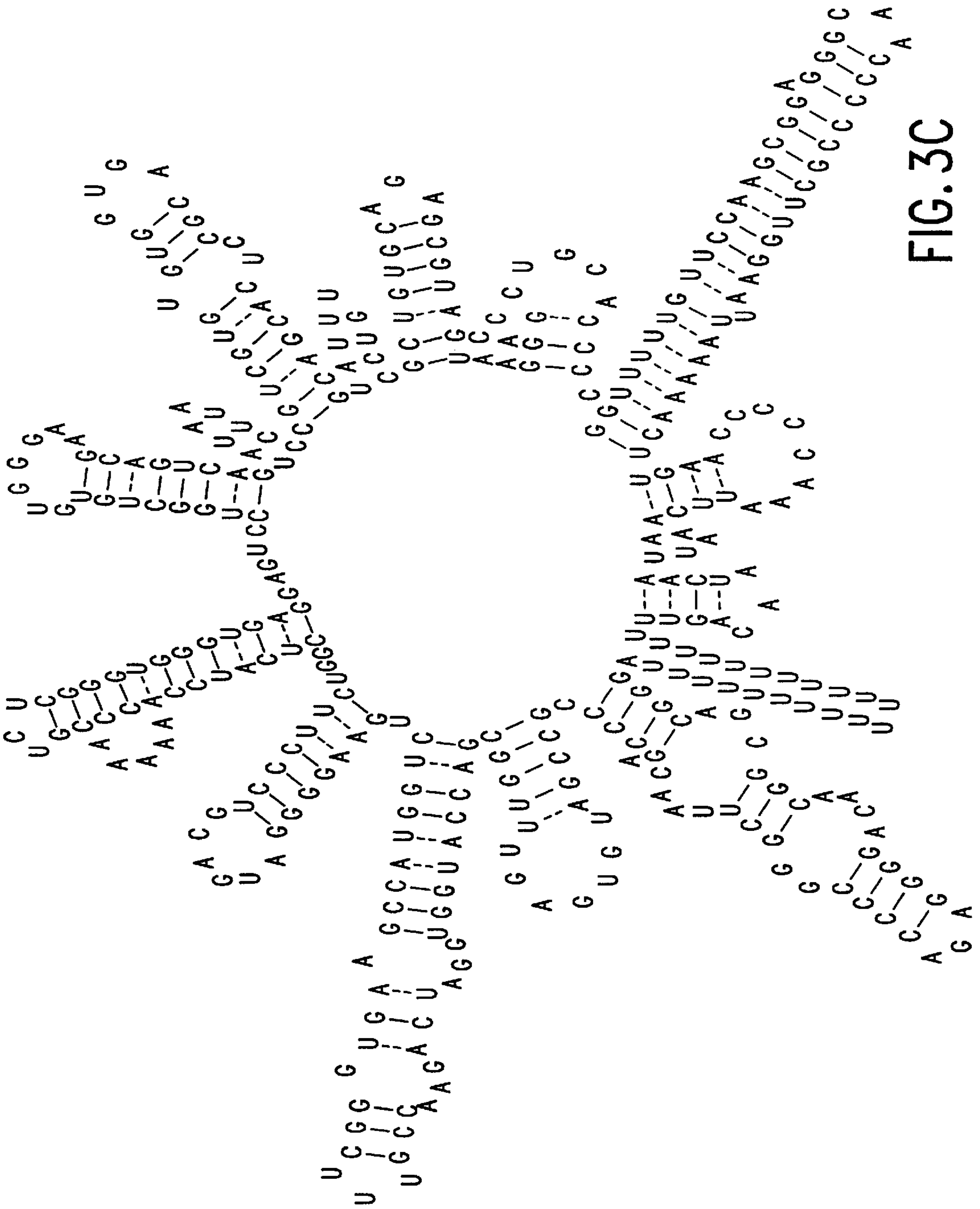
Figure 3D:
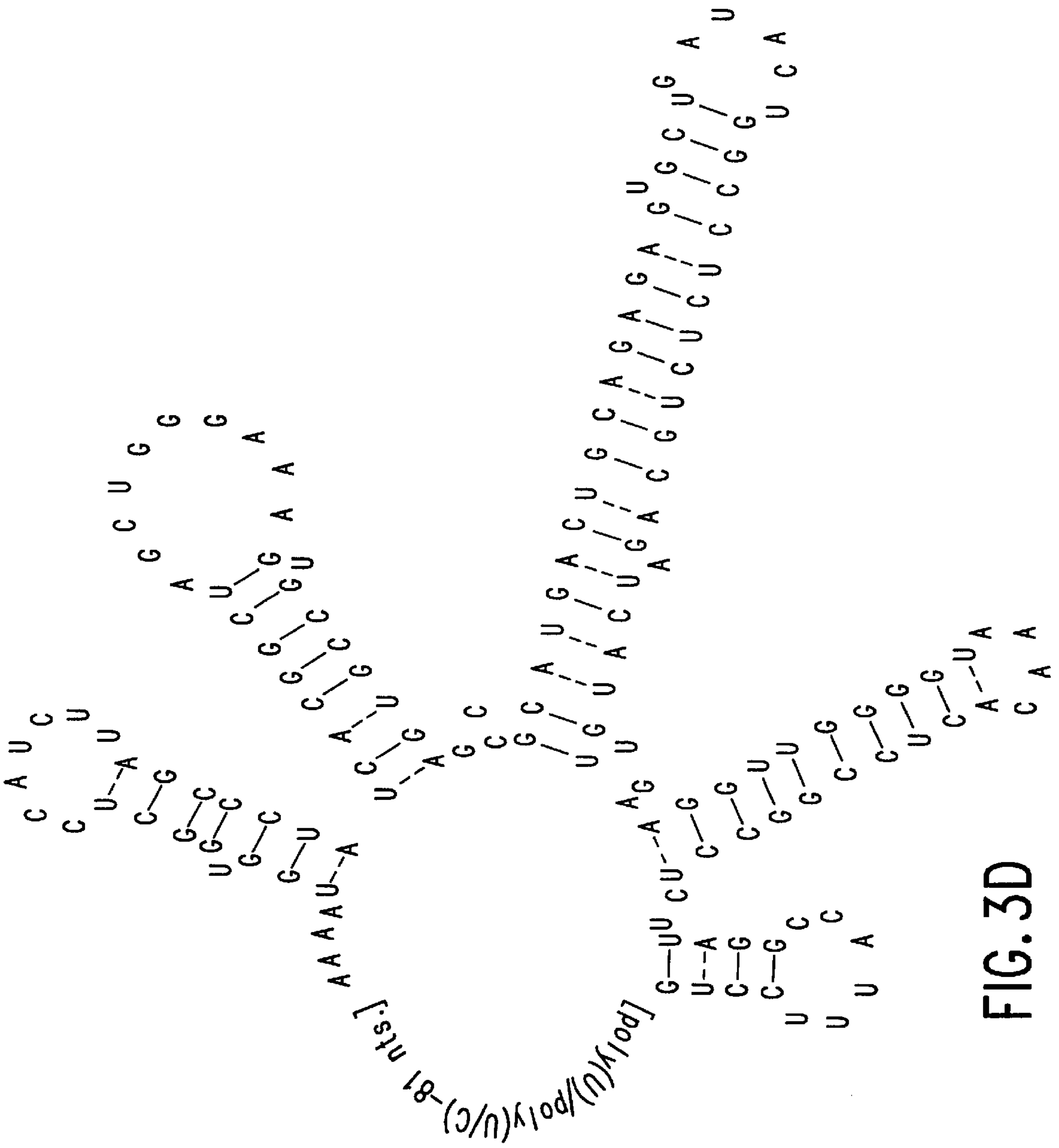

Not surprisingly, comparison of the 3' ntr of GBV-C with the 3' ntr of an infectious GBV-B clone and the infectious HCV clone used as a control demonstrated only 45.69% homology among the three sequences. GBV-C was more closely related to GBV-B than HCV, and of the two GB-hepatitis agents, GBV-C was more closely related to HCV than was GBV-B (FIG. 3A). Although there was little sequence homology of this region, analysis of the predicted secondary structures demonstrated several similarities (FIGS. 3B–D), particularly at the extreme 3' end (RNAdraw: an integrated program for RNA secondary structure calculation and analysis under 32-bit Microsoft Windows) Matzura and Wennborg, 1996). Although GBV-C does not have a polypyrimidine tract, the 3' end has three stem-loop structures closely resembling the HCV and GBV-B 3' end (FIG. 3B, FIG. 3C, and FIG. 3D, respectively). In addition, the 5' end of this region bears remarkable structural resemblance to GBV-B (FIG. 3B and FIG. 3C). The predicted free energy of the GBV-C, GBV-B, and HCV 3' ntr RNA structures (37° C.) were −92.98 kCal, −109.01 kCal, and −55.08 kCal, respectively (Matzura and Wennborg, 1996).

Example 4

Full-Length GBV-C RNA is Infectious in Cell Culture

Figure 1B:
Figure 4A:
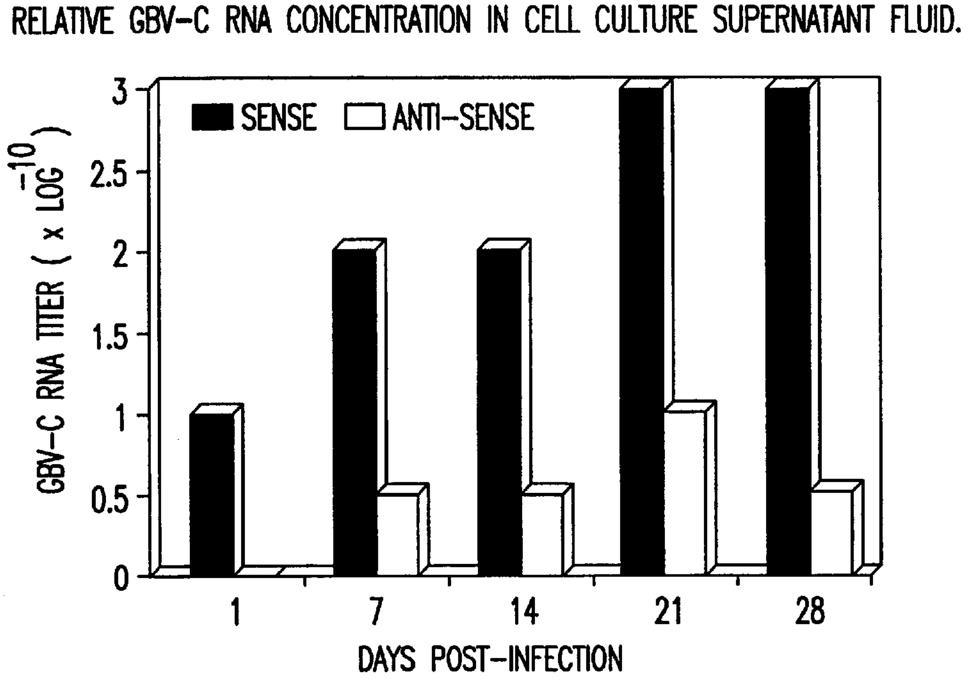
FIGS. 4A–B Detection of GBV-C RNA in cell culture supernatants (FIG. 4A) and cell lysates (FIG. 4B). Results are expressed as the relative GBV-C RNA end point dilution titer. GBV-C RNA was detected 1 day following infection, and after 7, 14, 21, and 28 days of culture.
Figure 4B:
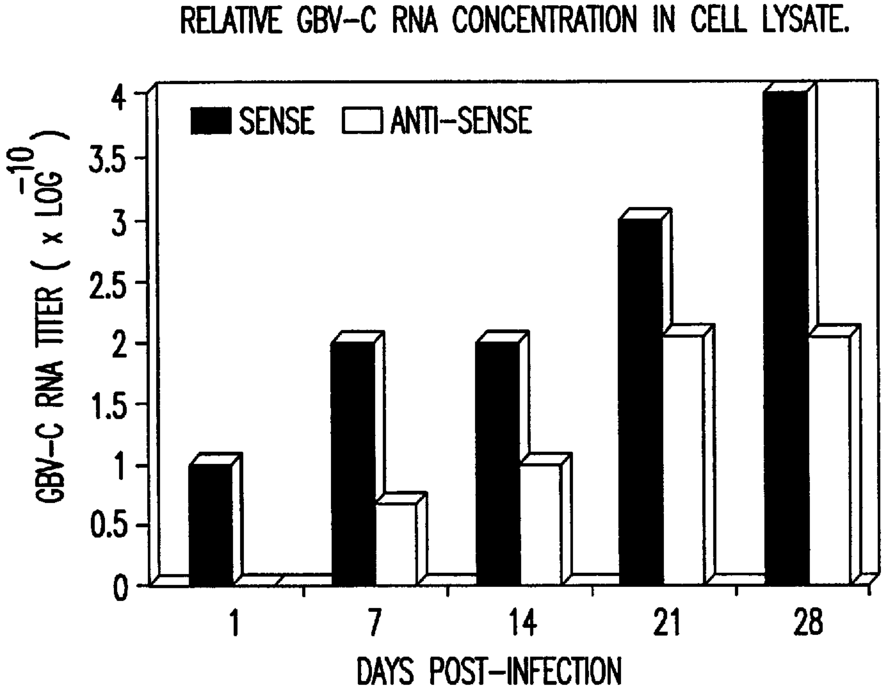

Full-length GBV-C transcripts were generated using T7 polymerase. For comparison, full length HCV RNA was also transcribed from an infectious cDNA clone using T7 polymerase (Kolykhalov et al., 1997). RNA from the transcription reactions was denatured with formamide and analyzed on a 1% agarose formaldehyde gel (FIG. 1B). The GBV-C transcript was approximately 9.4 kb, whereas the HCV transcript was approximately 9.7 kb. GBV-C and HCV RNA transcripts were transfected into PBMCs, Molt-4 and HepG-2 cell lines. Following transfection, PBMC's were supplemented with fresh, PHA-IL2 stimulated PBMC's weekly for four weeks. Culture supernatants and cell lysates were evaluated for GBV-C and HCV RNA, and GBV-C RNA was detected in all PBMC lysates and culture supernatants (Table 2). In contrast, HCV RNA was not detected in PBMCs cell lysates or culture supernatants after three weeks in culture (Table 5). GBV-C and HCV RNA were detected in MOLT-4 cell lysates for three or fewer weeks, and were detected in the culture supernatants for only the week of transfection (Table 5). GBV-C and HCV RNA were not detected in HepG2 cells within one week of transfection. Cell lysates and cell culture supernatants from the GBV-C transfected cells were used to infect fresh PHA-IL2 stimulated PBMC cultures for four passages, and persistent GBV-C infection was demonstrated (Table 5). All studies were performed in duplicate or triplicate, and transfections were repeated twice. To ensure that the GBV-C RNA detected in PBMC cell lysates and culture supernatants did not represent amplification of residual plasmid DNA, the cell lysate and supernatant fluids from which GBV-C RNA was detected were amplified in PCR™ reactions not containing MMLV RT. These reactions did not produce PCR™ products. In addition, the relative concentration of GBV-C positive and negative sense RNA in culture supernatants and cell lysates was determined by terminal dilution. FIG. 4 demonstrates that a low concentration of negative strand RNA was present in culture supernatants following 7 days of infection (pass 5 virus), concomitantly with an increase in positive strand RNA. Negative strand RNA was detected 14 days post-infection in the cell lysates, and increased on day 21 and 28.

Figure 5:
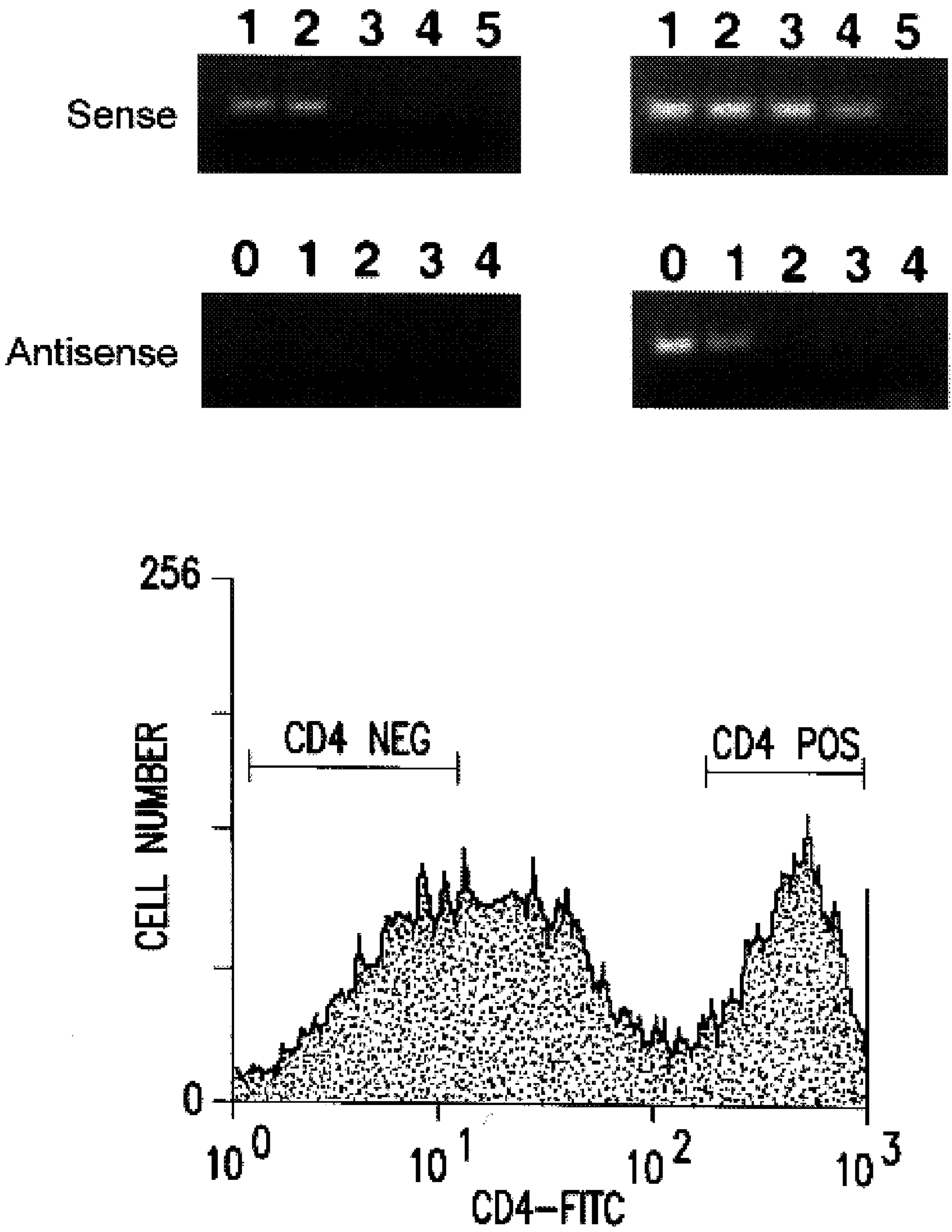
FIG. 5 CD4 positive and CD4 negative cells were sorted and collected by flow cytometry. The bars represent the cell populations sorted for these experiments. RNA was extracted from equal numbers of CD4+ and CD4− cells, and the relative end-point dilution titer of sense and antisense GBV-C RNA was measured. The numbers represent the dilution titer ($Log_{10}$).

To determine the immunophenotype of the PBMCs that supported GBV-C replication, cells were infected with passage 4 supernatant and five days later, CD4 positive and CD4 negative cells were sorted by flow cytometry. RNA was extracted from $1.5\times10^5$ CD4 positive and $2\times10^5$ CD4 negative cells respectively, and GBV-C RNA was evaluated by RT-PCR in each cell population. The relative concentration of both positive and negative strand viral RNA was 100-fold higher in CD4 positive cells than in CD4 negative cells, indicating that ≧99% of viral replication in PBMCs occurred in the CD4+ subset (FIG. 5).

Figure 6A:
FIGS. 6A–D GBV-C E2 expression in PBMCs. PBMCs were infected with supernatant from pass 4, and 24 h (FIG. 6A) and 96 h (FIG. 6B) post-infection, the cells were fixed and processed as described in Materials and Methods. GBV-C E2 expression was detected using a murine monoclonal anti-HGV E2 antibody as described in Materials and Methods. The same cells (24 hrs. post-infection) did not show specific cytoplasmic fluorescence when evaluated without the GBV-C E2 antibody (FIG. 6C), and mock infected PBMCs evaluated exactly the same as panel A and B did not demonstrate cytoplasmic fluorescence (FIG. 6D).
Figure 6B:
Figure 6C:
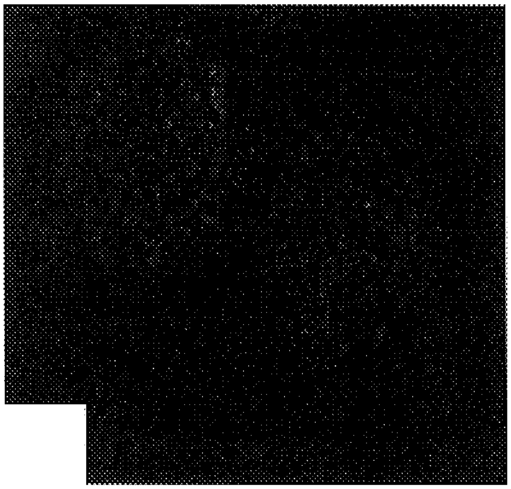
Figure 6D:
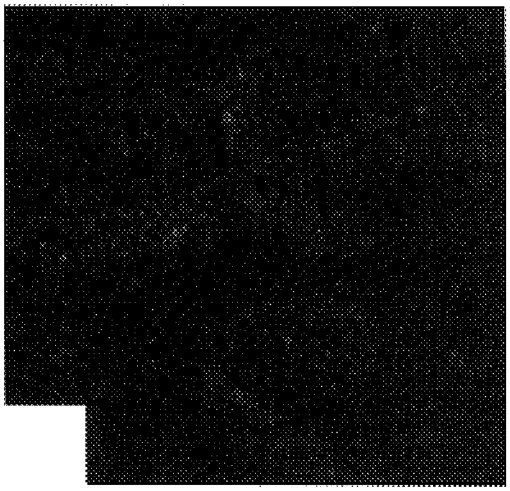

To further confirm that GBV-C RNA detection in cells represented viral replication, the $5^{th}$ passage of GBV-C infection cells was evaluated by indirect immunofluorescence. Two and 4 days post-infection, PBMCs were fixed and GBV-C E2 expression was assessed using a commercial anti-E2 monoclonal antibody. FIG. 6 demonstrates E2 expression in the cytoplasm of cells from pass 5 (FIGS. 6A, B) but not uninfected cells (FIG. 6D). Panel C shows infected cells evaluated as in A; however, an isotype control monoclonal antibody was used in place of the GBV-C E2 specific monoclonal antibody.

TABLE 5

Passage history of in vitro transfection of GBV-C and HCV full length RNA's and subsequent infection of primary peripheral blood mononuclear cells (PBMC) and MOLT-4 cells.

| Cells | Viruses | *Week 0 | 1 | 2 | 3 | 4 | 5 | 6 | 7 | 8 |
|---|---|---|---|---|---|---|---|---|---|---|
| | | | | Cells | | | | | | |
| PBMC | GBV-C | T | + | + | + | + | + | + | + | + |
| | HCV | T | + | + | + | − | − | − | − | − |
| MOLT-4 | GBV-C | T | + | + | + | − | − | − | − | − |
| | HCV | T | + | + | − | − | − | − | − | − |
| | | | | Culture Supernatant | | | | | | |
| PBMC | GBV-C | + | + | + | + | + | + | + | + | + |
| | HCV | + | − | − | − | − | − | − | − | − |
| MOLT-4 | GBV-C | + | − | − | − | − | − | − | − | − |
| | HCV | + | − | − | − | − | − | − | − | − |
| | **Generation | 0 | Ia | Ib | Ic | Id | II | III | IV | V |

T = DEAE transfection of cells with full length RNA transcripts;
+ = Viral RNA detected by RT-PCR;
− = Viral RNA not detected by RT-PCR.
*The number of weeks in culture as shown on top.
**The passage generation for PBMC's is shown. Following transfection, fresh PHA-IL2 stimulated PBMC's were added to the cells weekly for 4 weeks (generation Ia, Ib, Ic, and Id). Following this, cell culture supernatant was used to infect fresh cells (generation II, III, IV, V) MOLT-4 cells were passed weekly.

Example 5

GBV-C Particle Characterization

Figure 7A:
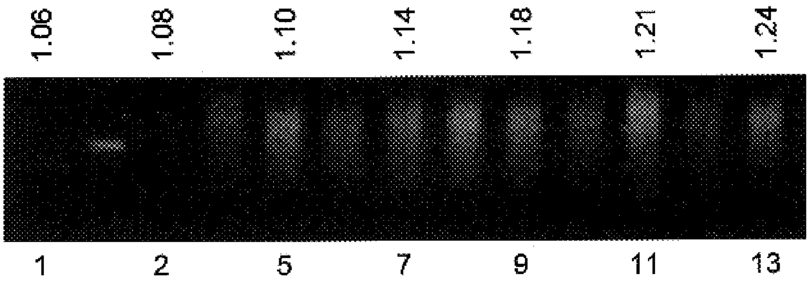
FIG. 7 Cell lysate and concentrated cell culture supernatant from the fourth passage of GBV-C in PBMCs were separated on a 20 to 60% (wt/wt) sucrose equilibrium gradient. The sucrose density of each fraction is shown on top in gram per milliliter. GBV-C RNA was extracted from each fraction, and detected by RT-PCR.
Figure 7B:
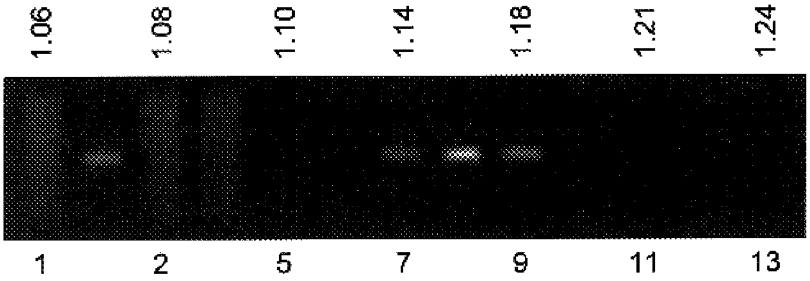
Figure 8A:
FIGS. 8A–C Electron micrographs of GBV-C particles precipitated with an anti-GBV-C E2 antibody (FIG. 8A). Immuno-gold labeling of particles with (FIG. 8B) and without (FIG. 8C) the E2 antibody are shown. The arrow indicates an immuno-gold labeled particle.
Figure 8B:
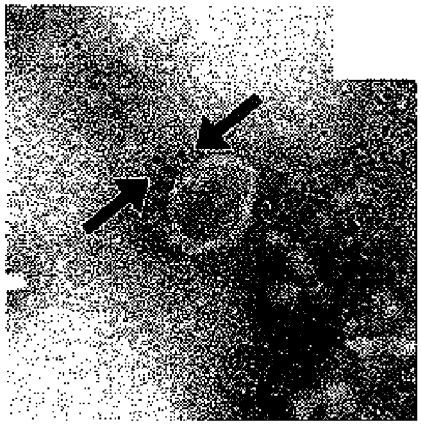

In order to determine the biophysical properties of GBV-C particles generated by the infectious clone, concentrated supernatants and cell lysates from infected PBMCs ($5^{th}$ passage) were characterized by sucrose gradient centrifugation (FIG. 7). RNA was extracted from each fraction, and GBV-C RNA was detected by RT-PCR. Similar to GBV-C particles found in plasma (Xiang et al., 1998), a very low density particle type was identified with a density of 1.06 g/ml in cell lysates (FIG. 8A). This particle type, and an intermediate density particle were identified in supernatant samples (buoyant densities of 1.06 g/ml and 1.12 to 1.17 g/ml, respectively) (FIG. 8B).

Figure 8C:
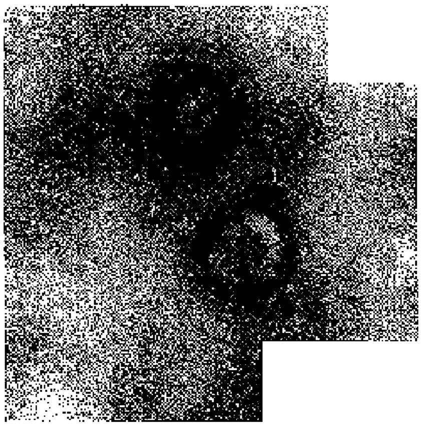

To visualize GBV-C particles, culture supernatants were concentrated from the $5^{th}$ passage and incubated with the anti-E2 MAb. Polymorphic virus-like particles, 60–70 nm in diameter, were seen which appeared to be enveloped (FIG. 8A and FIG. 8C). Many of these particles had electron-dense structures in the center suggestive of nucleocapsids. Gold-labeled anti-mouse IgG was applied to GBV-C containing grids with (B) or without (C) the anti-E2 MAb. Immunogold labeled particles were observed only in the grids first incubated with anti-E2 antibody.

Example 6

GBV-C Inhibits HIV Replication and Delays Aids

Materials and Methods

Clinical Evaluation

All serum and plasma specimens were prepared within 2 hours of blood sampling, and were stored at −80° C. until use. Patient demographics and $CD4^+$ T cell counts were prospectively entered onto a relational database (Paradox, Borland Scientific), and surivival statistics were obtained from state health department records. To identify GBV-C viremia, RNA was extracted from serum or plasma (200 $\mu$l) using a GITX extraction methods previously described (Xiang et al. 1998). One-fourth of the RNA preparation was used as the template in a nested RT-PCR reaction to amplify GBV-C RNA using primers from the 5'ntr region (Xiang et al., 1988; Xiang et al., 1999). PCT products were separated by agarose gel electrophoresis and visualized by ethidium bromide staining. Negative control samples and positive control samples were evaluated with each PCT reaction. To be considered positive, the sample was positive on two separate occasions, or two samples from differents dates were positive. A chi-square or Fisher;s exact test was used for the comparison of categorical variables, and a two-samples t-test was used for the comparison of continuous variables. A cod proportional hazards model was used to compare survival between GBV-C infected and non-infected individuals, controlling for age, baseline CD4 count, gender, race, HCV antibody status, and HIV transmission category. Statistical analysis was performed using SPSS version 8.0 (Chicago, Ill.).

Cells and Viruses

PBMCs from healthy blood donors (HCV RNA and antibody negative, HGV RNA negative,a nd HBV surface antigen negative) were prepared and incubated in RPMI 1640 media containing phytohemagglutinin (PHA 10 $\mu$g/ml; DIFCO, Detroit, Mich.), and 5% interleukin-2 (IL-2; Cellular Products Inc., Buffalo, N.Y.) at 35° C. in 5% CO for 48 hours prior to infection as previously described (Xiang et al., 2000). Cell viability was measured by trypan blue exclusion microscopy. Protein synthesis in mock- and GBV-C-infected PBMC's was determined by metabolically ravelling cellular proteins with $^{35}$S-methionine and determining the counts per minute of incoporation by acid precipitation as previously described (Wunschmann et al., 2000). The GBV-C isolate used in this study was derived from cell culture supernatant fluids previously transfected with full-length GBV-C RNAtranscripts and passed 3 to 6 times in PBMC cultures as previously described (XIang et al., 2000). The HIV isolate used in these studies was an NSI strain (NIH AIDS Research and Reference Reagent Program strain 92UG031; Catalog #1741). HIV stock preparations were propagated as previously described Wunschmann and Stapleton, 2000). Following activation in PHA/IL-2 for two days $1\times10^6$ PBMC's were washed, re-suspended in 100 $\mu$l of virus preparation containing HIV, GBV-C or both viruses (multiplicity of infection approximately 0.1). Co-infection was also done varying the timing of HIV or GBV-C infection. Cells were incubated for 4 hours at 37° C. prior to the addition of 2 ml fresh media, and cells were incubated overnight. The next morning, cells were washed and culture supernatant sampes were immediately collected (time 0), and twice weekly thereafter. HIV replication was determined by measuring positive RNA in culture supernatants (Wunschmnann and Stapleton, 2000; Cook et al., 1997), and GBV-C replication was determined by measuring positive sense RNA in culture supernatants and positive and negative sense RNA in cell lysates as described (Xiang et al., 2000).

Flow Cytometry

HIV receptor (CD4) and major co-receptor (CXCR4 and CCR5) expression on PBMC's following infection with GBV-C was determined by flow cytometry (FACScan, Becton Dickinson, San Jose, Calif.) (Xiang et al., 2000; Wunschmann and Stapleton, 2000). Cells were infected for varying lengths of time with GBV-C or mock-infected culture supernatants. Cells were pelleted, re-suspended in 10 μg/ml murine anti-CD4 (IgG1 conjugated with FITC), biotinylated anti-CXCR4 (IgG2a), anti-CCR5 antibodies (IgG 2a, R-PE conjugated) (Pharmingen, Inc., San Diego, Calif.) or murine isotype control antibodies (murine IgG1-FITC, IgG2a-biotin, and IgG2s R-PE, respectively) for 30 min at 4° C. CXCR4 and the appropriate isotype control-stained cells were incubated with streptavidin conjugated CyChrome for 30 min (Pharmingen, Inc.). Between each steps, cells were washed two times with PBS.

Results

Figure 9:
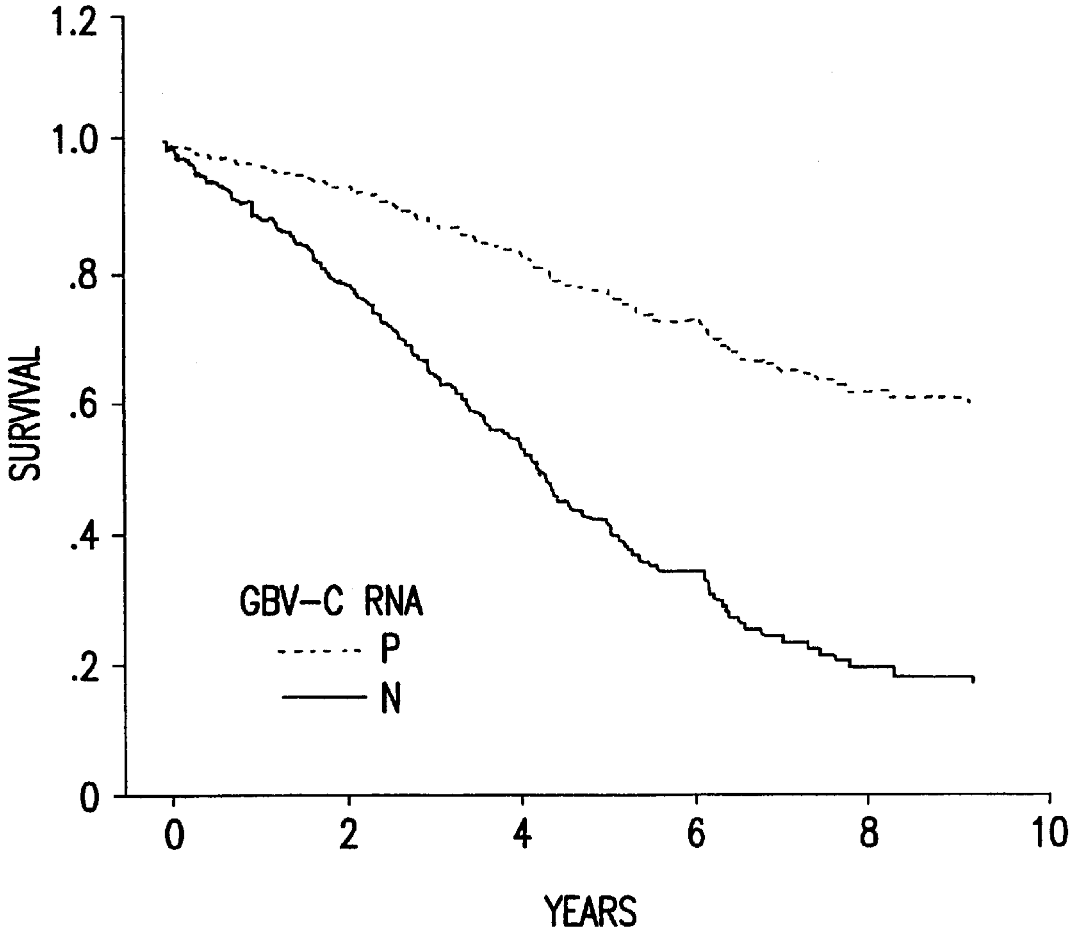
FIG. 9 Survival curves for HIV-infected individuals with and without GBV-C viremia from a Cox proportional hazards analysis. P GBV-C RNA positive (144 subjects) and N=GBV-C RNA negative (218 subjects).

To determine if GBV-C infection prolonged survival in a large population of HIV-1 infected people with a variety of modes of HIV transmission, frozen serum and plasma samples from 362 HIV-positive individuals were studied. Samples were tested for the presence of GBV-C RNA using a previously described RT-PCR method (Xiang et al., 1998). One hundred forty-four (39.7%) of our patients were viremic on replicate samples. The baseline clinical and demographic variables for the GBV-C RNA positive and negative groups were very similar, except for the baseline CD4+ T cell count and HCV antibody status (Table 6). The mean CD4 count was higher in the GBV-C RNA positive group, although the difference was not statistically significant (Table 6). Using a Cox proportional hazards analysis, controlling for baseline CD4 count, age, race, gender, HIV transmission category, and HCV antibody status, the adjusted relative risk of mortality among GBV-C negative individuals was 3.41 ($p<0.001$; confidence intervals 2.37–4.91) compared to the GBV-C viremic group. FIG. 9 demonstrates the survival curve for GBV-C RNA positive and GBV-C RNA negative HIV-positive patients. A significant mortality difference between the two groups was seen in individuals with CD4+ T cell counts of 0 to 50 per $mm^3$, 51 to 200 cells per $mm^3$, and 201 to 500 cells per $mm^3$. The number of deaths among people with more than 500 CD4+T cells/$mm^3$ was lower in the GBV-C viremic group, although the numbers were too small to achieve statistical significance (Table 7). By Cox regression analysis, the likelihood of survival at 9 years was approximately 62% in the GBV-C RNA positive group compared to only 18% in the GBV-C negative group.

TABLE 6

Baseline demographics and mortality among human GB virus (GBV-C) RNA positive and negative individuals

| Variable | GBV-C RNA status: Positive (N = 144) | Negative (N = 218) | Two tailed p-value* |
|---|---|---|---|
| Age (mean yrs) | 34.5 | 35.1 | 0.48 |
| Gender: N (%) female | 17 (11.8) | 26 (11.9) | 1.0 |
| Race: N (%) caucasian | 128 (88.9) | 189 (86.7) | 0.626 |
| Baseline CD4 + T cell count (mean) | 313.5 | 263.5 | 0.07 |
| HCV antibody positive: N (%) | 35 (24.3) | 97 (44.5) | <0.001 |
| Transmission category: | | | |
| Intravenous drug use: N (%) | 23 (16.0) | 36 (16.5) | 1.0 |
| Sexual**: N (%) | 113 (78.4) | 162 (74.3) | 0.365 |
| Blood or blood products: N (%) | 8 (5.6) | 20 (9.2) | 0.2 |
| Died during follow up period: N (%) | 41 (28.5) | 123 (56.4) | <0.001 |

*Pearsons's Chi-square or Fisher's Exact test for categorical variables, t-test for continuous variables.
**80% of the sexual transmission was in men having sex with men, and the remaining 20% was heterosexual. There was no difference in the distribution of sexual transmission category by GBV-C RNA status.

TABLE 7

Mortality rates among GBV-C RNA positive and negative individuals stratified by baseline CD4+ T cell count

| Baseline CD4 count | N | HGV (GB Virus C) RNA status: Positive (N = 144) | Negative (N = 218) | two tailed p-value |
|---|---|---|---|---|
| ≦50 cells/$mm^3$ | 73 | 11/25 (44.0%) | 36/48 (75.0%) | 0.01 |
| 51–200 cells/$mm^3$ | 98 | 14/32 (43.8%) | 50/66 (75.8%) | 0.003 |
| 201–500 cells/$mm^3$ | 122 | 13/56 (23.2%) | 29/66 (43.9%) | 0.022 |
| >500 cells/$mm^3$ | 69 | 3/31 (6.5%) | 8/38 (21.1%) | 0.322 |

Figure 11:
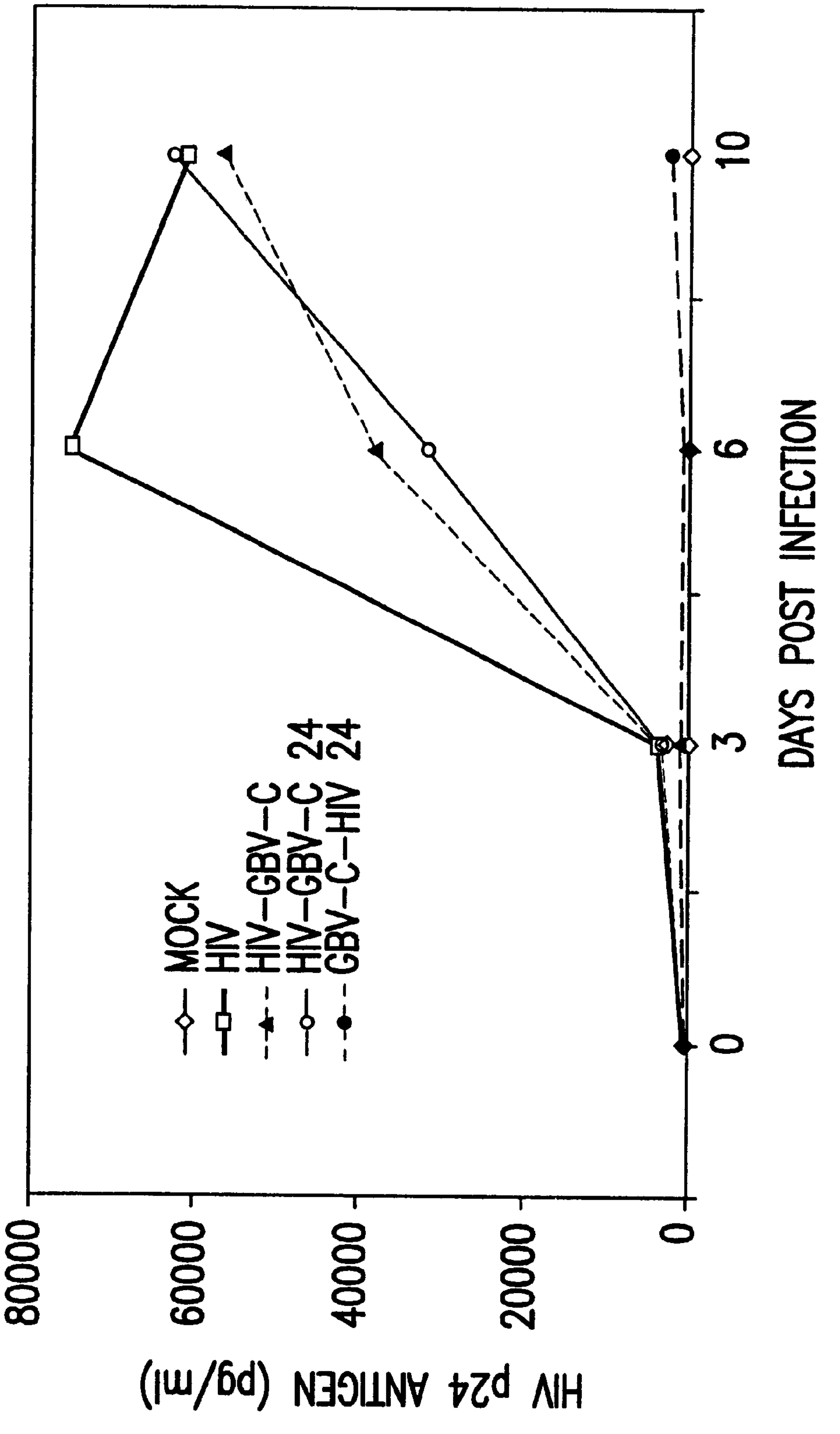
FIG. 11 GBV-C infection of PBMCs inhibits HIV replication. PHA-IL-2-stimulated PBMCs were mock infected (mock) or infected with HIV alone (HIV), HIV and GBV-C simultaneously (HIV-GB), HIV followed by GBV-C 24 hours later (HIV-GBV 24), or GBV-C followed by HIV 24 hours later (GB-HIV 24). HIV replication was measured by determining the concentration of HIV p24 antigen in culture supernatants immediately post infection, and 3, 6 and 10 days later.

To examine potential mechanisms to explain why HIV-GBV-C co-infected subjects live longer than patients infected only with HIV, the effects of GBV-C on HIV infection was examined in vitro. To determine if GVB-C infection altered HIV replication in vitro, replicate PBMC cultures were infected with HIV alone, GBV-C alone, or with HIV and GBV-C. Mock-infected PBMC's served as the negative controls. In vitro, HIV replication was diminished in cells infected with both GBV-C and HIV compared to control cells infected with HIV alone, although the inhibition was not complete. Since the inhibitory effect of GBV-C replication on HIV growth in cell culture occurred when HIV infection preceded GBV-C, and since GBV-C did not decrease the expression of CD4, CXCR4 or CCR5, the mechanism of inhibition does not appear to involve an HIV cell receptor. GBV-C isolates were obtained from culture supernatants following transfection of PBMCs with full-length RNA transcripts from our infectious GBV-C clone (Xiang, et al. 2000; three separate GBV-C isolates with different passage histories were used in these studies and all demonstrated inhibition activity. The NSI HIV isolate used in these studies was obtained from the NIH AIDS Repository as previously described, Wünschmann and Stapleton, 2000). PBMCs were stimulated with PHA and IL-2 as previously described (Xiang et al., 2000), and replicate cultures were infected with HIV alone, GBV-C alone, HIV and GBV-C simultaneously, HIV for 24 hours followed by GBV-C, or GBV-C for 24 hours followed by HIV or the mock control. FIG. 11 demonstrates that HIV replication, demonstrated by the production of p24 antigen in the cell culture supernatant fluid, was inhibited by 31.6% after 3 days in culture, and further inhibited by 49.4% following 6 days in culture when GBV-C and HIV were used to infect cells simultaneously. Similarly, HIV replication decreased 23% (3 days) and 58.1% (6 days) post-infection when the HIV infection was initiated 24 hours prior to GBV-C infection. However, HIV replication was almost completely abrogated 3 and 6 days post-infection if GBV-C infection was initiated 24 hours prior to HIV infection (87.4% and 100% reduction at day 3 and 6 respectively). If the cultures were fed with fresh, PHA-IL2-stimulated PBMCs on Day 6 post-infection, the extent of inhibition in the co-infected cells diminished (FIG. 11). GBV-C was detected in cell culture supernatants by RT-PCR and replication was confirmed by detecting negative strand GBV-C RNA. These experiments have been repeated a total of seven times using three GBV-C virus preparations with different passage history, and with two different HIV virus preparations with similar results. In most experiments, HIV replication increased over time, even in cells initially infected with GBV-C. Thus, the inhibitory effect of GBV-C infection was not completely protective.

Figure 10:
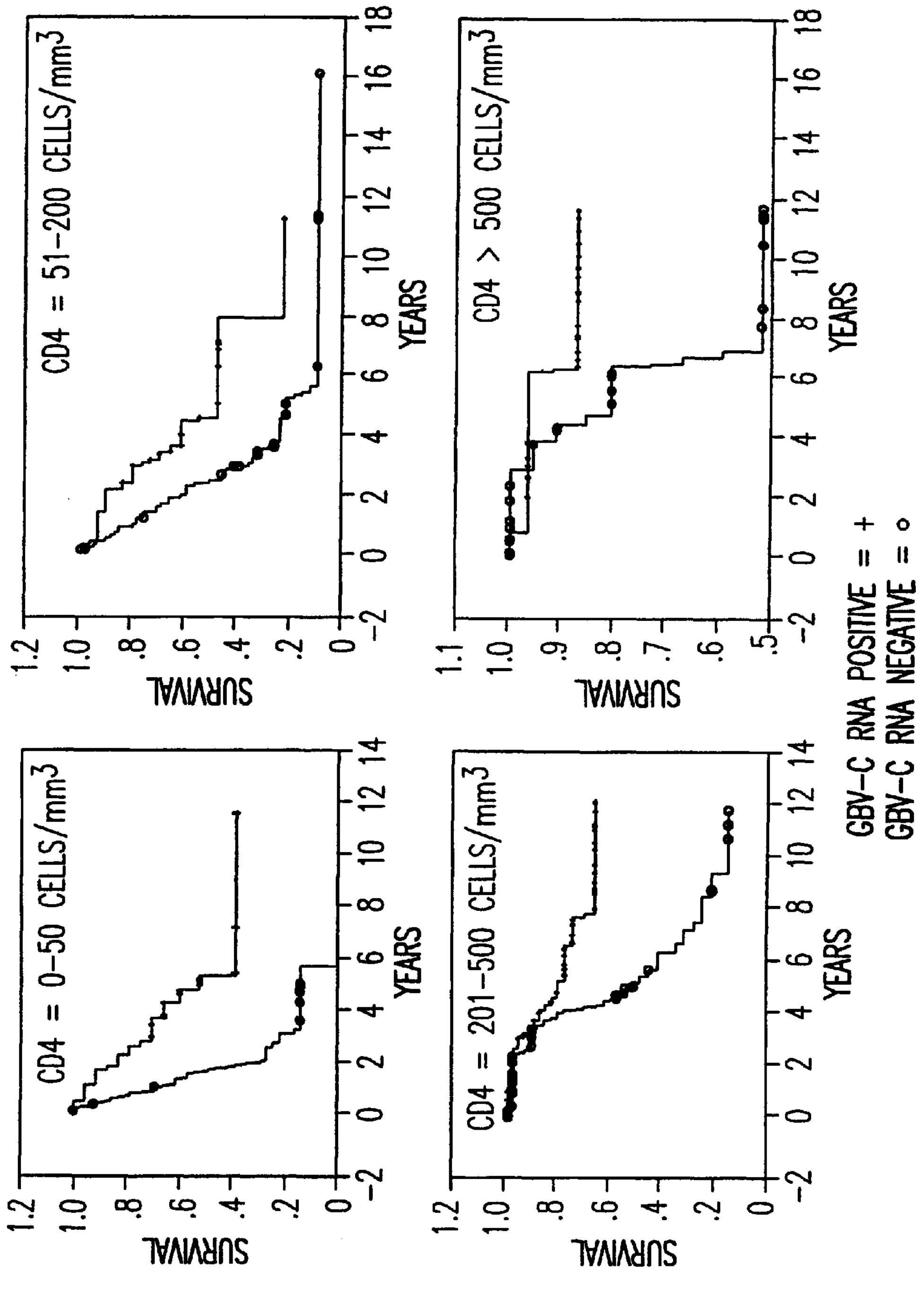
FIG. 10 Survival in HIV-infected people with and without GBV-C viremia stratigied by baseline CD4+ T cell counts. Survival rates among people with more than 500 CD4+ T cells/$mm^3$ were much higher in both groups (note different scale).

The difference in mortality between HIV and HIV-GBV-C co-infected people was observed in all CD4+ T cell count strata (Table 7). FIG. 10 demonstrates the Kaplan-Meier survival curves for the HIV-GBV-C co-infected and HIV only groups based on their baseline CD4+ T cell count. Examiner subjects who entered our clinic prior to 1990, 6 years prior to the availability of highly active antiretroviral therapy (HAART), 9 of 27 GBV-C RNA positive patients died compared to 48 of 67 GBV-C RNA negative individuals ($p<0.001$). Of the 47 HIV-infected people in our study who entered our clinic after 1995, one died prior to Jul. 1, 2000, the time data collection ceased.

HIV-related mortality was significantly lower among GBV-C-viremic individuals, independent of baseline CD4 count, age, race, gender, transmission category and HCV antibody status. GBV-C does not completely prevent CD4 T cell depletion, as at baseline, there were 25 individuals with HIV-GBV-C co-infection who had fewer than 50 CD4+ T cells/mm$^3$, 32 with 51 to 200 CD+ T cells/mm$^3$ and 56 with 201 to 500 CD 4+ T cells/mm$^3$ (Table 7). However, even these patients demonstrated a significant decreased mortality rate compared to HIV infected people without GBV-C infection. Thus, the effect of GBV-C infection on mortality is more pronounced than the effect on CD4 count. Decreased mortality was observed even when controlled for variables known to be associated with rapid HIV disease progression (e.g., age and baseline CD4).

Figure 12:
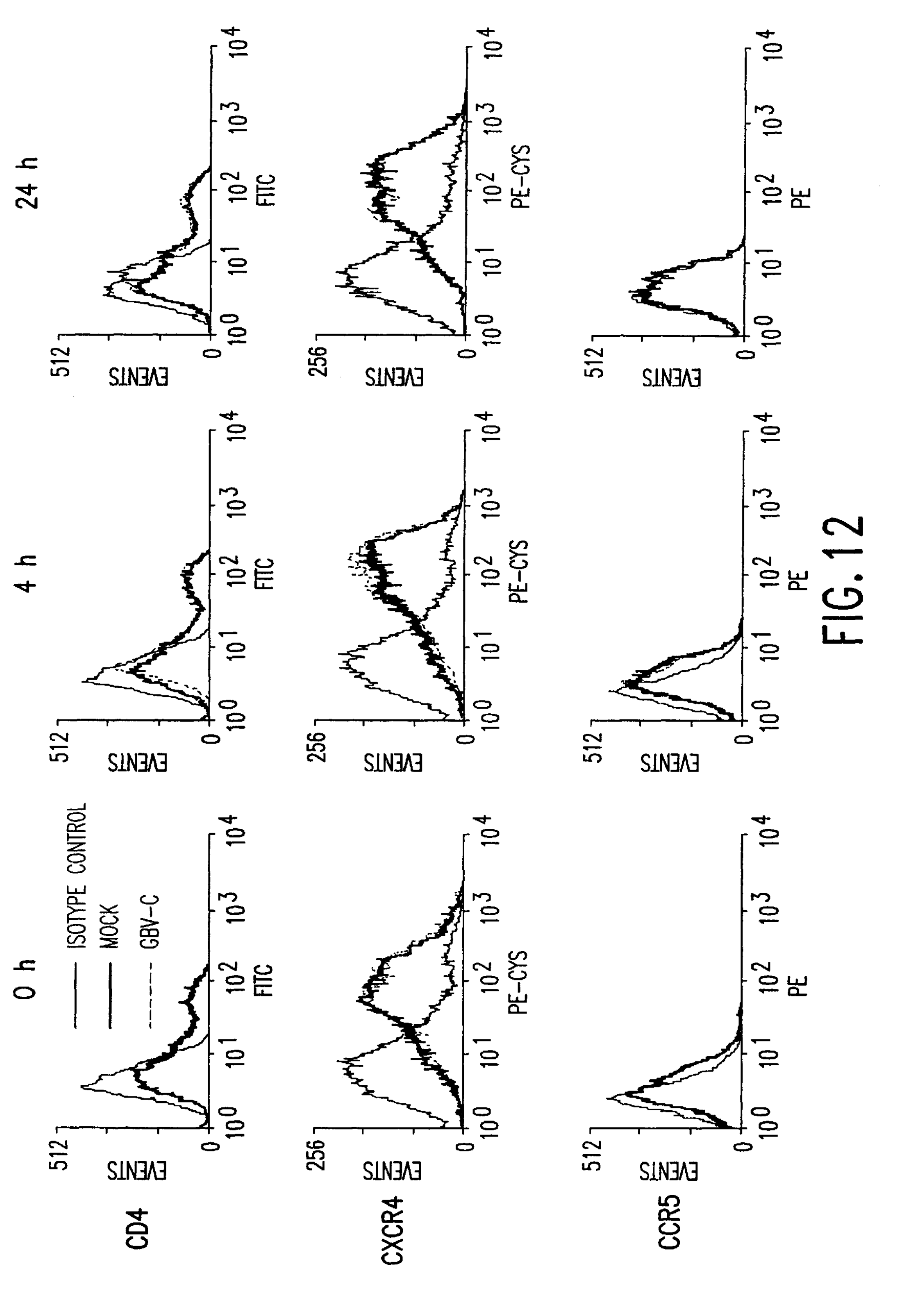
FIG. 12 GBV-C infection does not alter surface expression of HIV receptors. PHA-IL-2-stimulated normal donor PBMCs were infected with GBV-C or mock infected, and cells were evaluated by FACS immediately (0 hr), 4 and 24 hours later. CD4 expression, CXCR4 expression and CCR5 expression are demonstrated in the top, middle and lower panels respectively. FITC, PE-Cy5 and PE conjugated antibodies were used to quantify receptor expression, and the isotype controls are shown as previously described (W ünschmann et al., 2000). There were no difference between mock-infected and GBV-C-infected cell surface expression of any of these HIV receptors.

To determine if GBV-C infection led to a change in the expression of HIV cell receptors, thus decreasing HIV entry, the surface expression of CD4, CXCR4 and CCR5 on GBV-C- and mock-infected PBMC cultures was measured using flow activated cell sorting (FACS) analysis (Xiang et al., 2000). The antibodies used in FACS analysis were obtained from Pharmingen, Inc., San Diego, Calif. There were no differences between mock- and GBV-C-infected cells in the expression of either the major HIV receptor (CD4) or the co-receptors (CXCR4 or CCR5) immediately after infection, and 5, 20, 60, 240 and 1440 minutes after GBV-C infection. FIG. 12 demonstrates data obtained from selected time points. Thus, the inhibitory effect that GBV-C infection had on HIV replication appears to involve a step in HIV replication which occurs after receptor binding.

Example 7

Further Characterization of GBV-C in PBMCs

Figure 13:
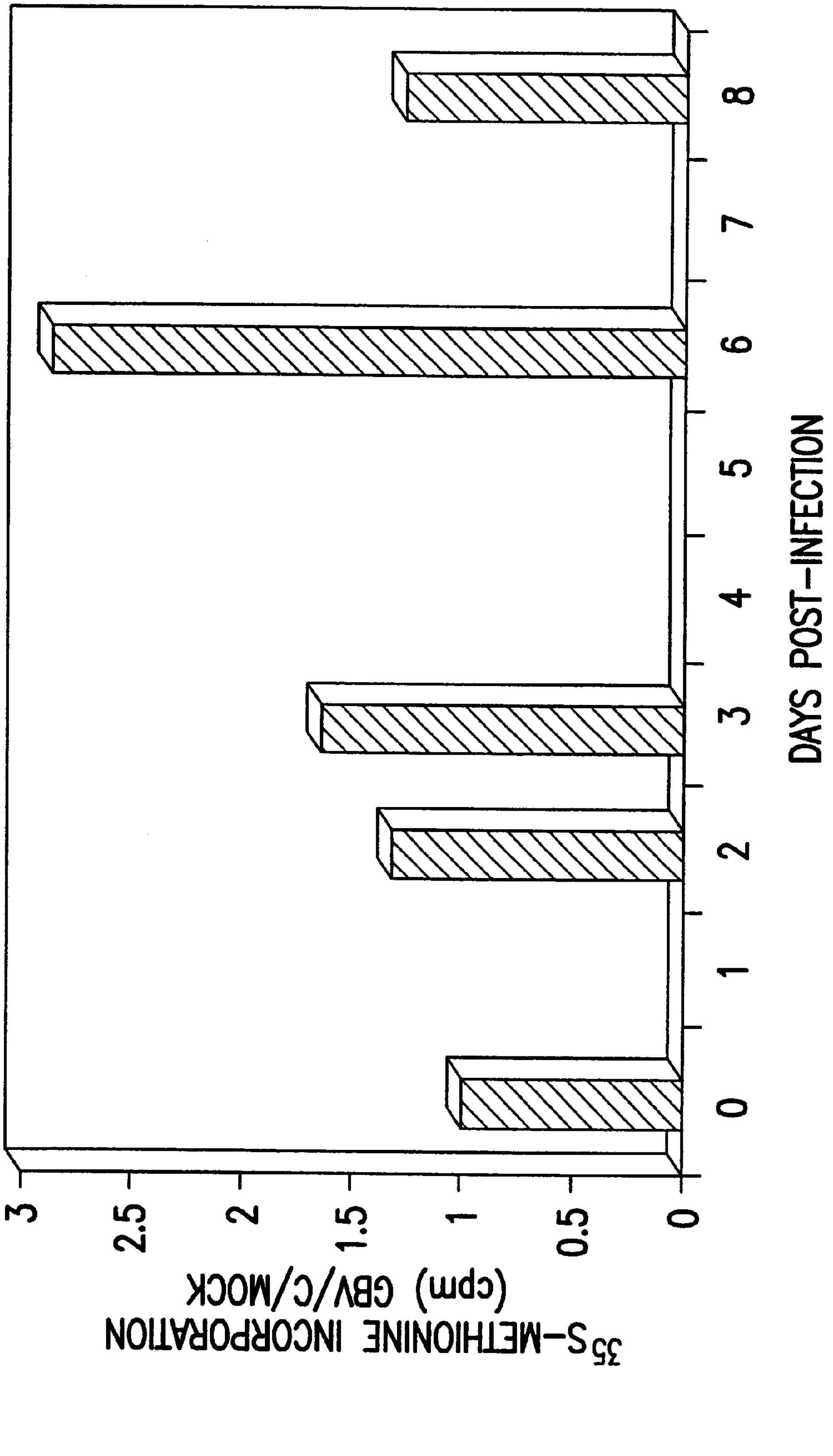
FIG. 13 Metabolic activity of cells infected with GBV-C. Peripheral blood mononuclear cells infected with GBV-C or mock-infected PBMCs were compared for metabolic activity by assaying for incorporation of $^{35}S$-methionine.

The effect of GBV-C infection on the metabolic activity of IL-2-, PHA-activated peripheral blood mononuclear cells (PBMC's) was investigated. Equal volumes of culture supernatants from GBV-C- or mock-infected PBMCs were used to infect replicate cultures of activated PBMC's ($1\times10^6$). Immediately following (day 0) and 2, 3, 6 and 8 days later, cells in culture wells were washed, placed in methionine-free media and incubated with $^{35}$S-methionine-cysteine (trans-label) for 15 minutes. Mock- and GBV-C-infected cells were again washed, lysed and incorporated $^{35}$S-methionine was determined by acid-precipitation and counted as previously described (Wünschmann et al., 2000). Data are shown as the ratio of incorporated $^{35}$S-methionine counts per minute (cpm) in GBV-C infected cells divided by cpm in mock-infected cells. The data indicate that GBV-C increases metabolic activity of PBMCs following infection (FIG. 13), thus the effect on HIV is not related to toxicity of GBV-C infection. In addition, GBV-C may influence cellular factors that increase either proliferation, protein synthesis, or prevent apoptosis relative to mock-infected cells.

Figure 14:
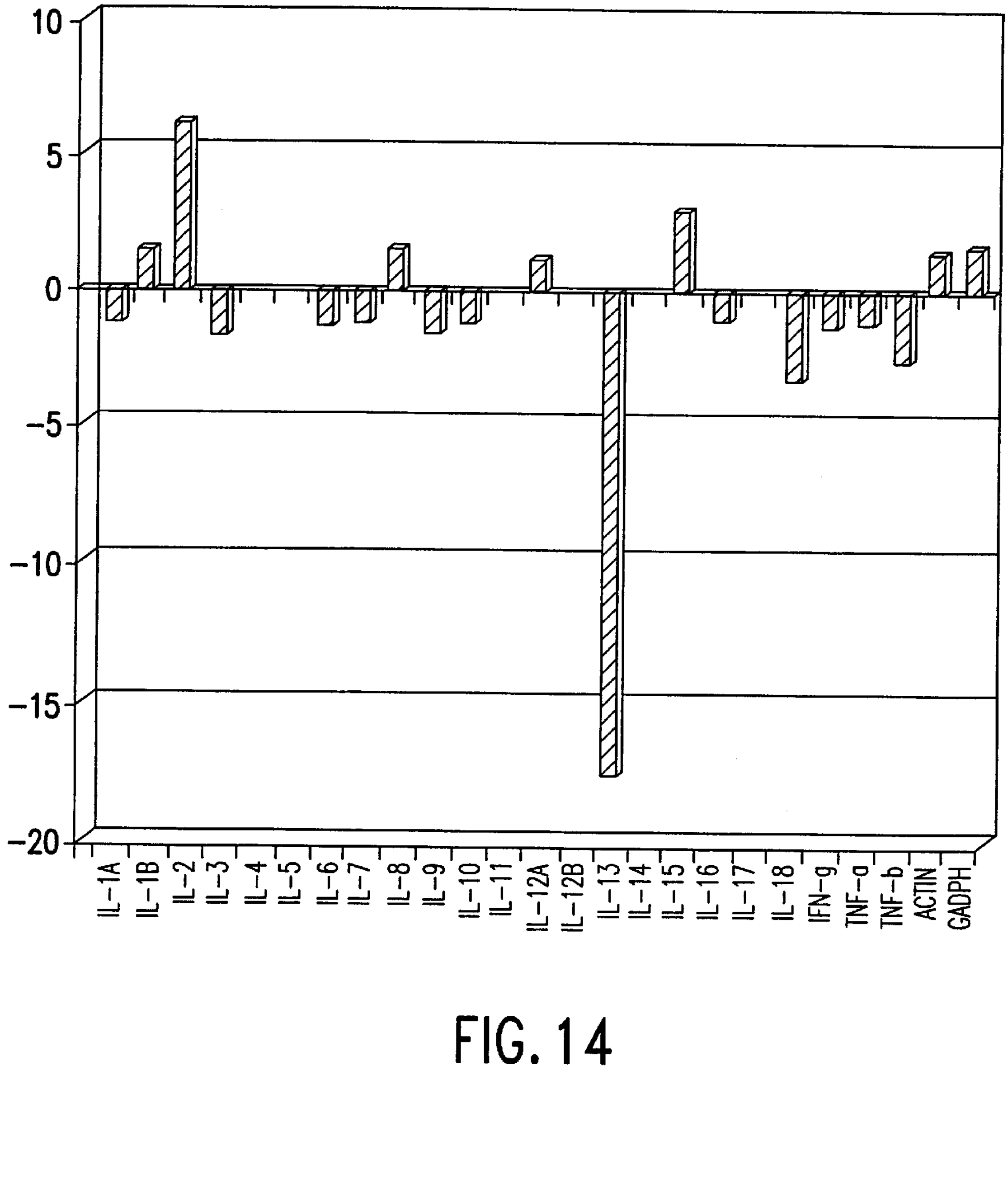
FIG. 14 Alteration of Cytokine Expression with GBV-C Infection. A cytokine array assay on GBV-C-infected PBMCs is shown.

Using the "Cytokine Array" (SuperArray, Inc.), the effect of GBV-C infection on induction of cytokines in PBMC's was compared with Mock-infected PBMCs. Cells were infected with GBV-C or mock-infected culture supernatants, and 24 hrs. later RNA was prepared using the Trizol RNA extraction methodology. RNA was used to generate $^{32}$P-dCTP labeled probes, and these were hybridized to nitrocellulose membranes containing cytokine genes, and actin and GADPH controls. Hybridization intensity was determined by counting $^{32}$P counts per minute (cpm) with a phosphoimager. Data represent the cpm for each gene (shown on the X axis) in the GBV-C-infected cells divided by the mock-infected cells (FIG. 14). IL-2 was increased more than 5-fold and IL-13 decreased more than 20-fold. In addition, IL-1B, IL-8, IL-15 were increased relative to control, and all other cytokines were decreased relative to controls.

Figure 15:
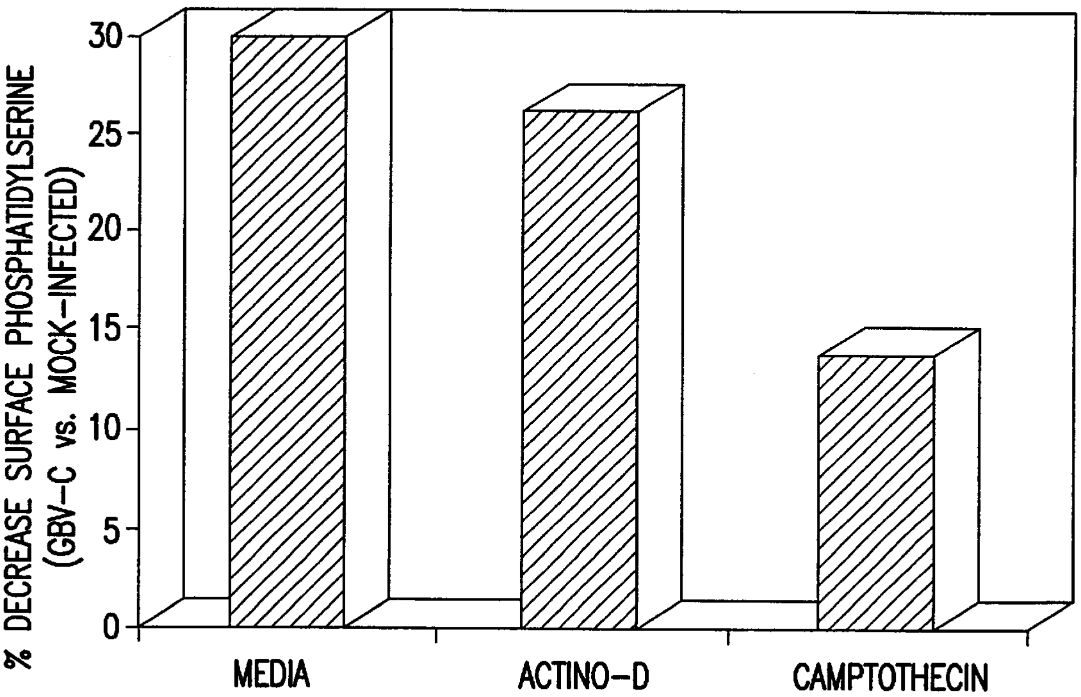
FIG. 15 Annexin binding to phosphatidylserine on surface of cells is a marker of apoptosis. GBV-C-infected and mock-infected PBMCs were evaluated for apoptosis.

GVB-C was also evaluated for its ability to induce apoptosis. Annexin binding to phosphatidylserine on surface of cells is a marker of apoptosis. PBMCs were stimulated for 48 h in PHA, LPS/IL-2 medium, infected with GBV-C (pass3 JX and pass $4_{pb}$) for 48 h. To determine if GBV-C inhibits apoptosis, mock-infected and GBV-C-infected cells were incubated in either media, or in the presence of inducers of apoptosis for 5 h (actinomycin-D or Camptothecin). AnnexinV staining of phosphatidylserine on the outer leaflet of the cell plasma membrane (a marker of apoptosis) was done according to manufacturer's instructions (Vybrant Apoptosis Assay Kit 2—Molecular Probes). AnnexinV staining was done according to manufacturer's instructions (Vybrant Apoptosis Assay Kit 2 —Molecular Probes) and annexin labeling was accomplished by flow cytometry. Both actinomycin-D and media treated cells demonstrated reduced apoptosis in GBV-C-infected cells compared to mock-infected cells (FIG. 15). Thus, GBV-C did not induce apoptosis, but instead reduced or inhibited it.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 3,949,064, issued Apr. 6, 1976
U.S. Pat. No. 4,174,384, issued Nov. 13, 1979
U.S. Pat. No. 4,554,101, issued Nov. 19, 1985
U.S. Pat. No. 4,683,195, issued Jul. 28, 1987
U.S. Pat. No. 4,683,202, issued Jul. 28, 1987
U.S. Pat. No. 4,690,915, issued Sep. 1, 1987
U.S. Pat. No. 4,800,159, issued Jan. 24, 1989
U.S. Pat. No. 4,879,236, issued Nov. 7, 1989
U.S. Pat. No. 4,883,750, issued Nov. 28, 1989
U.S. Pat. No. 4,946,773, issued Aug. 7, 1990
U.S. Pat. No. 5,187,260, issued Feb. 16, 1993
U.S. Pat. No. 5,199,942, issued Apr. 6, 1993
U.S. Pat. No. 5,279,721, issued Jan. 18, 1994
U.S. Pat. No. 5,354,855, issued Oct. 11, 1994
U.S. Pat. No. 5,359,046, issued Oct. 25, 1994
U.S. Pat. No. 5,620,896, issued Apr. 15, 1997
U.S. Pat. No. 5,650,298, issued Jul. 22, 1997
U.S. Pat. No. 5,840,873, issued Nov. 24, 1998
U.S. Pat. No. 5,843,640, issued Dec. 1, 1998
U.S. Pat. No. 5,843,650, issued Dec. 1. 1998
U.S. Pat. No. 5,843,651, issued Dec. 1, 1998
U.S. Pat. No. 5,843,663, issued Dec. 1, 1998
U.S. Pat. No. 5,846,708, issued Dec. 8, 1998
U.S. Pat. No. 5,846,709, issued Dec. 8, 1998
U.S. Pat. No. 5,846,717, issued Dec. 8, 1998
U.S. Pat. No. 5,846,726, issued Dec. 8, 1998
U.S. Pat. No. 5,846,729, issued Dec. 8, 1998
U.S. Pat. No. 5,846,783, issued Dec. 8, 1998
U.S. Pat. No. 5,849,481, issued Dec. 15, 1998
U.S. Pat. No. 5,849,483, issued Dec. 15, 1998
U.S. Pat. No. 5,849,486, issued Dec. 15, 1998
U.S. Pat. No. 5,849,487, issued Dec. 15, 1998
U.S. Pat. No. 5,849,497, issued Dec. 15, 1998
U.S. Pat. No. 5,849,546, issued Dec. 15, 1998
U.S. Pat. No. 5,849,547, issued Dec. 15, 1998
U.S. Pat. No. 5,851,770, issued Dec. 22, 1998
U.S. Pat. No. 5,851,772, issued Dec. 22, 1988
U.S. Pat. No. 5,853,990, issued Dec. 29, 1998
U.S. Pat. No. 5,853,992, issued Dec. 29, 1998
U.S. Pat. No. 5,853,993, issued Dec. 29, 1998
U.S. Pat. No. 5,856,092, issued Jan. 5, 1999
U.S. Pat. No. 5,858,652, issued Jan. 12, 1999
U.S. Pat. No. 5,861,244, issued Jan. 19, 1999
U.S. Pat. No. 5,863,732, issued Jan. 26, 1999
U.S. Pat. No. 5,863,753, issued Jan. 26, 1999
U.S. Pat. No. 5,866,331, issued Feb. 2, 1999
U.S. Pat. No. 5,866,336, issued Feb. 2, 1999
U.S. Pat. No. 5,866,337, issued Feb. 2, 1999
U.S. Pat. No. 5,866,366, issued Feb. 2, 1999
U.S. Pat. No. 5,871,986, issued Feb. 16, 1999
U.S. Pat. No. 5,874,563, issued Feb. 23, 1999
U.S. Pat. No. 5,882,864, issued Mar. 16, 1999
U.S. Pat. No. 5,900,481, issued May 4, 1999
U.S. Pat. No. 5,905,024, issued May 18, 1999
U.S. Pat. No. 5,910,407, issued Jun. 8, 1999
U.S. Pat. No. 5,912,124, issued Jun. 15, 1999
U.S. Pat. No. 5,912,145, issued Jun. 15, 1999
U.S. Pat. No. 5,912,148, issued Jun. 15, 1999
U.S. Pat. No. 5,916,776, issued Jun. 29, 1999
U.S. Pat. No. 5,916,779, issued Jun. 29, 1999
U.S. Pat. No. 5,919,626, issued Jul. 6, 1999
U.S. Pat. No. 5,919,630, issued Jul. 6, 1999
U.S. Pat. No. 5,922,574, issued Jul. 13, 1999
U.S. Pat. No. 5,925,517, issued Jul. 20, 1999
U.S. Pat. No. 5,925,525, issued Jul. 20, 1999
U.S. Pat. No. 5,925,565, issued Jul. 20, 1999
U.S. Pat. No. 5,928,862, issued Jul. 27, 1999
U.S. Pat. No. 5,928,869, issued Jul. 27, 1999
U.S. Pat. No. 5,928,870, issued, Jul. 27, 1999
U.S. Pat. No. 5,928,905, issued Jul. 27, 1999
U.S. Pat. No. 5,928,906, issued Jul. 27, 1999
U.S. Pat. No. 5,929,227, issued Jul. 27, 1999
U.S. Pat. No. 5,932,413, issued Aug. 3, 1999
U.S. Pat. No. 5,932,451, issued Aug. 3, 1999
U.S. Pat. No. 5,935,791, issued Aug. 10, 1999
U.S. Pat. No. 5,935,819, issued Aug. 10, 1999
U.S. Pat. No. 5,935,825, issued Aug. 10, 1999
U.S. Pat. No. 5,939,291, issued Aug. 17, 1999
U.S. Pat. No. 5,942,391, issued Aug. 24, 1999
U.S. Pat. No. 5,958,895, issued Sep. 28, 1999
U.S. Pat. No. 6,004,799, issued Dec. 21, 1999
European Application No. 0273085
European Application No. 320 308
European Application No. 329 822
GB Application No. 2 202 328
PCT Application No. PCT/US87/00880
PCT Application No. PCT/US89/01025
PCT Application WO 88/10315
PCT Application WO 89/06700
PCT Application WO 90/07641
Agnello et al., *PNAS*, 96:12766–12771, 1999.
Akiyoshi et al., *Am. J. Gastroenterol.*, 94:1627–1631, 1999.
Aksentijevich et al., *Hum. Gene Ther.*, 7(9):1111–22, 1996.
Almendro, et al., *J Immunol.*, 157(12):5411–21, 1996.
Alter et al., *N. Engl. J. Med.*, 336:741–746. 1997a.
Alter et al., *N. Engl. J. Med.*, 336:747–754. 1997b.
Angel et al., *Cell*, 49:729, 1987b.
Angel et al., *Mol. Cell. Biol.*, 7:2256, 1987a.
Arap et al., *Cancer Res.*, 55:1351–1354, 1995.
Asada et al., *J. Virol.* 73:4019–4028, 1999.

Atchison and Perry, *Cell*, 46:253, 1986.
Atchison and Perry, *Cell*, 48:121, 1987.
Ausubel et al., *Current Protocols in Molecular Biology*, Greene Publishing Associates and Wiley Interscience, N.Y., 1989.
Baichwal and Sugden, In: *Gene Transfer*, Kucherlapati R, ed., New York, Plenum Press, pp. 117–148, 1986.
Banerji et al., *Cell*, 35:729, 1983.
Bao et al., *Hum. Gene Ther.*, 7:355–365, 1996.
Bass et al., *Cancer Gene Ther.*, 2:97–104, 1995.
Beard et al., *Hepatology*, 30:316–324, 1999.
Bedzyk et al., *J. Biol. Chem.*, 265:18615, 1990
Benvenisty and Neshif, *Proc. Nat. Acad. Sci. USA*, 83:9551–9555, 1986.
Berkhout et al., *Cell*, 59:273, 1989.
Birkenmeyer et al., *J. Med. Virol.*, 56:44–51, 1998.
Blanar et al., *EMBO J.*, 8:1139, 1989.
Bodine and Ley, *EMBO J.*, 6:2997, 1987.
Boshart et al., *Cell*, 41:521, 1985.
Bosze et al., *EMBO J.*, 5:1615, 1986.
Braddock et al., *Cell*, 58:269, 1989.
Bukh et al., *Virol.*, 262:470–478, 1999.
Bukh et al., *J. Inf. Dis.*, 177:855–862, 1998.
Bulla and Siddiqui, *J. Virol.*, 62:1437, 1986.
Burbage et al., *Leuk Res*, 21(7):681–690, 1997.
Burger et al., *Antimicrob Agents Chemother.*, 37(7):1426–31, 1993.
Bussemakers et al., *Cancer Res.*, 52:2916–2922, 1992.
Caldas et al., *Nat. Genet.*, 8:27–32, 1994.
Campbell and Villarreal, *Mol. Cell. Biol.*, 8:1993, 1988.
Campere and Tilghman, *Genes and Dev.*, 3:537, 1989.
Campo et al., *Nature*, 303:77, 1983.
Capaldi et al., *Biochem Biophys. Res. Comm.*, 76:425, 1977.
Carbonell et al., *FEMS Microbiol. Lett.*, 177(1):75–82, 1999.
Casey et al., *Oncogene*, 6:1791–1797, 1991.
Celander and Haseltine, *J. Virology*, 61:269, 1987.
Celander et al., *J. Virology*, 62:1314, 1988.
Chandler et al., *Cell*, 33:489, 1983.
Chandler et al., *Proc Natl. Acad. Sci. USA*, 94(8):3569–601, 1997.
Chang et al., *Hepatology*, 14:134A, 1991.
Chang et al., *Mol. Cell. Biol.*, 9:2153, 1989.
Chatterjee et al., *Proc. Nat'l Acad. Sci. USA.*, 86:9114, 1989.
Chaudhary et al., *Proc. Nat'l Acad. Sci.*, 87:9491, 1990
Chen and Okayama, *Mol. Cell Biol.*, 7:2745–2752, 1987.
Cheng et al., *Cancer Res.*, 54:5547–5551, 1994.
Cheung et al., *Arch Biochem. Biophys.*, 305(2):563–9, 1993.
Chol et al., *Cell*, 53:519, 1988.
Cocea, *Biotechniques*, 23(5):814–6, 1997.
Coffin, In: *Virology*, ed., New York: Raven Press, pp. 1437–1500, 1990.
Cohen, Hirschhorn, Horowitz, Rubinstein, Polmar, Hong. and Martin, Jr., *Proc. Nat'l Acad. Sci. USA* 75, 472–476, 1978.
Cohen et al., *J. Virol.*, 61:3035–3039, 1987.
Cook et al., *J. Invest. Med.*, 45:265–271, 1997.
Costa et al., *Mol. Cell. Biol.*, 8:81, 1988.
Coupar et al., *Gene*, 68:1–10, 1988.
Cripe et al., *EMBO J*, 6:3745, 1987.
Culotta and Hamer, *Mol Cell. Biol.*, 9:1376, 1989.
Dandolo et al., *J. Virology*, 47:55, 1983. Dawson et al., *J. Med. Virol.* 50:97–103, 1996.
Dawson et al., *J. Med. Virol.*, 50:97–103. 1996.
de Martino et al., *J. Infect. Dis.*, 178:862–865, 1998.
De Villiers et al., *Nature*, 312:242, 1984.
Deacon et al., *Science* 270:988–991, 1995.
Deschamps et al., *Science*, 230:1174, 1985.
Dickens et al., *Hepatology*, 25:1285–1286. 1997.
Dong et al., *Hum. Gene Ther.*, 7:319–331, 1996.
Dubensky et al., *Proc. Nat'l Acad. Sci. USA*, 81:7529–7533, 1984.
Easterbrook, *J. Infect.* 38:71–73, 1999.
Edbrooke et al., *Mol. Cell. Biol.*, 9:1908, 1989.
Edelman and Crossin, *Annu. Rev. Biochem.*, 60:155–190, 1991.
Edelman, *Annu. Rev. Biochem.*, 54:135–169, 1985.
Edlund et al., *Science*, 230:912, 1985.
Elvander et al., *Acta. Vet.Scand.* 39:251–264, 1998.
Emerson et al., *J. Virol.*, 66:6649–6654, 1992.
Fechheimer et al., *Proc. Nat'l Acad. Sci. USA*, 84:8463–8467, 1987.
Felgner et al., *Proc. Nat'l. Acad. Sci. USA*, 84(21):7413–7, 1987.
Feng and Holland, *Nature*, 334:6178, 1988.
Ferkol et al., *FASEB J.*, 7:1081–1091, 1993.
Feucht et al., *Hepatology*, 26:491–494, 1997.
Firak and Subramanian, *Mol. Cell. Biol.*, 6:3667, 1986.
Fogeda et al.,. *J. Virol.* 73:4052–4061, 1999.
Fogeda et al., *J. Virol.*, 73:4052–4061, 1999.
Forster and Symons, "Self-cleavage of plus and minus RNAs of a virusoid and a structural model for the active sites," *Cell*, 49:211–220, 1987.
Fraley et al., *Proc. Nat'l Acad. Sci. USA*, 76:3348–3352, 1979.
Freshney, R. I. "Animal Cell Culture: a Practical Approach", Second Edition, Oxford/N.Y., IRL Press, Oxford University Press, 1992.
Friedmann, *Science*, 244:1275–1281, 1989.
Frixen et al., *J. Cell Biol.*, 113:173–185, 1991.
Frohman, In: *PCR Protocols: A Guide To Methods And Applications*, Academic Press, N.Y., 1990.
Fujita et al., *Cell*, 49:357, 1987.
Gabizon et al., *Cancer Res.*, 50(19):6371–8, 1990.
Gale, Jr. et al., *Mol.Cell.Biol.* 18:5208–5218, 1998
Gerlach et al., *Nature* (London), 328:802–805, 1987.
Ghosh and Bachhawat, In: *Liver diseases, targeted diagnosis and therapy using specific receptors and ligands*, (Wu G, Wu C ed.), New York: Marcel Dekker, pp. 87–104, 1991.
Giancotti and Ruoslahti, *Cell*, 60:849–859, 1990.
Gilles et al., *Cell*, 33:717, 1983.
Gloss et al., *EMBO J*, 6:3735, 1987.
Godbout et al., *Mol. Cell. Biol.*, 8:1169, 1988.
Gomez-Foix et al., *J. Biol. Chem.* 267:25129–25134, 1992.
Gonzalez-Zulueta et al., *Cancer Research*, 55(20):4531–4535, 1995.
Goodboum and Maniatis, *Proc. Nat'l Acad. Sci. USA*, 85:1447, 1988.
Goodman et al., *Blood*, 84:1492–1500, 1994.
Gopal, *Mol. Cell Biol.*, 5:1188–1190, 1985.
Gossen et al., *Proc. Nat'l Acad. Sci. USA*, 89:5547–5551, 1992.
Gossen et al., *Science*, 268:1766–69, 1995.
Graham and Prevec, *Biotechnology*, 20:363–390, 1992.
Graham and Van Der Eb, *Virology*, 52:456–467, 1973.
Greene et al., *Immunology Today*, 10:272, 1989.
Grosschedl and Baltimore, *Cell*, 41:885, 1985.
Grunhaus and Horwitz, *Seminar in Virology*, 3:237–252, 1992.
Gutierrez et al., *J. Med. Virol.*, 53:167–173. 1997.
Haslinger and Karin, *Proc. Nat'l Acad. Sci. USA.*, 82:8572, 1985.
Hauber and Cullen, *J. Virology*, 62:673, 1988.

Hen et al., *Nature*, 321:249, 1986.
Hensel et al., *Lymphokine Res.*, 8:347, 1989.
Heringlake et al., *J. Infect. Dis.*, 177:1723–26, 1998.
Herman et al., *Cancer Research*, 55(20):4525–4530, 1995.
Hermonat and Muzyczka, *J. Cell Biol.*, 101:1094–1099, 1985.
Herr and Clarke, *Cell*, 45:461, 1986.
Herz et al., *Proc. Natl. Acad. Sci. USA*, 90:2812–2816, 1993.
Hirochika et al., *J. Virol.*, 61:2599, 1987.
Hirsch et al., *Mol. Cell. Biol.*, 10:1959, 1990.
Holbrook et al., *Virology*, 157:211, 1987.
Hollstein et al., *Science*, 253:49–53, 1991.
Hong et al., *Virology*, 256:36–44, 1999.
Horlick and Benfield, *Mol. Cell. Biol.*, 9:2396, 1989.
Horwich et al., *J. Virol.*, 64:642–650, 1990.
Huang et al., *Cell*, 27:245, 1981.
Huang et al., *Nature Med.* 2:1240–1243, 1996.
Hussussian et al., *Nature Genetics*, 15–21, 1994.
Hwang et al., *Mol. Cell. Biol.*, 10:585, 1990.
Imagawa et al., *Cell*, 51:251, 1987.
Imbra and Karin, *Nature*, 323:555, 1986.
Imler et al., *Mol. Cell. Biol.*, 7:2558, 1987.
Imperiale and Nevins, *Mol. Cell. Biol.*, 4:875, 1984.
Jakobovits et al., *Mol. Cell. Biol.*, 8:2555, 1988.
Jameel and Siddiqui, *Mol. Cell. Biol.*, 6:710, 1986.
Jaynes et al., *Mol. Cell. Biol.*, 8:62, 1988.
Johnson et al., *Mol. Cell. Biol.*, 9:3393, 1989.
Joyce, *Nature*, 338:217–244, 1989.
Kadesch and Berg, *Mol. Cell. Biol.*, 6:2593, 1986.
Kamb et al., *Nature Genetics*, 8:22–26, 1994.
Kamb et al., *Science*, 2674:436–440, 1994.
Kaneda et al., *Science*, 243:375–378, 1989.
Karin et al., *Mol. Cell. Biol.*, 7:606, 1987.
Katinka et al., *Cell*, 20:393, 1980.
Katinka et al., *Nature*, 290:720, 1981.
Kato et al., *J. Biol. Chem.*, 266:3361–3364, 1991.
Kawamoto et al., *Mol. Cell. Biol.*, 8:267, 1988.
Kiledjian et al., *Mol. Cell. Biol.*, 8:145, 1988.
Kiyosawa et al., *Intervirology*, 42:185–195, 1999.
Klamut et al., *Mol. Cell. Biol.*, 10:193, 1990.
Klein et al., *Nature*, 327:70–73, 1987.
Kobayashi et al., *J Med. Virol*, 57:114–121, 1999.
Koch et al., *Mol. Cell. Biol.*, 9:303, 1989.
Kolykhalov et al., *Science*, 277:570–574, 1997.
Kolykhalov et al., *J. Virol.*, 70:3363–3371, 1996.
Kraus et al., *FEBS Lett.*, 428(3):165–70, 1998.
Kriegler and Botchan, In: *Eukaryotic Viral Vectors*, Y. Gluzman, ed., Cold Spring Harbor: Cold Spring Harbor Laboratory, N.Y., 1982.
Kriegler and Botchan, *Mol. Cell. Biol.*, 3:325, 1983.
Kriegler et al., *Cell*, 38:483, 1984a.
Kriegler et al., *Cell*, 53:45, 1988.
Kriegler et al., In: *Cancer Cells 2/Oncogenes and Viral Genes*, Van de Woude et al. eds, Cold Spring Harbor, Cold Spring Harbor Laboratory, 1984b.
Kriegler et al., In: *Gene Expression*, D. Harner and M. Rosenberg, eds., New York: Alan R. Liss, 1983.
Kuhl et al., *Cell*, 50:1057, 1987.
Kunz et al., *Nucl. Acids Res.*, 17:1121, 1989.
Kwoh et al., *Proc. Natl. Acad. Sci. USA*, 86(4):1173–1177, 1989.
Kyte and Doolittle, *J. Mol. Biol.*, 157:105–132, 1982.
Lareyre, et al., *J. Bio. Chem.*, 274(12):8282–90, 1999.
Larsen et al., *Proc. Nat'l Acad. Sci. USA.*, 83:8283, 1986.
Laskus et al., *J. Virol.*, 72:3072–3075. 1998.
Laspia et al., *Cell*, 59:283, 1989.
Latimer et al., *Mol. Cell. Biol.*, 10:760, 1990.
Le Gal La Salle et al., *Science*, 259:988–990, 1993.
Leary et al., *J. Med. Virol.*, 48:60–67. 1996.
Lee et al., *DNA Cell Biol.*, 16(11):1267–75, 1997.
Lee et al., *Mol. Endocrinol.*, 2: 404–411, 1988.
Lee et al., *Nature*, 294:228, 1981.
Lefrere et al., *J.Infect.Dis.* 179:783–789, 1999.
Levenson et al., *Hum. Gene Ther.*, 9(8):1233–6, 1998.
Levinson et al., *Nature*, 295:79, 1982.
Levrero et al., *Gene*, 101:195–202, 1991.
Lin and Guidotti, *J. Biol. Chem.*, 264:14408–14414, 1989.
Lin et al., *Mol. Cell. Biol.*, 10:850, 1990.
Linnen et al., *Science*, 271:505–508. 1996.
Luria et al., *EMBO J.*, 6:3307, 1987.
Lusky and Botchan, *Proc. Nat'l Acad. Sci. USA.*, 83:3609, 1986.
Macejak et al., *Nature*, 353:90–94, 1991.
Majors and Varmus, *Proc. Nat'l Acad. Sci. USA.*, 80:5866, 1983.
Mann et al., *Cell*, 33:153–159, 1983.
Massuda et al., *Proc Natl Acad Sci USA* , 94(26) :14701–14706, 1997.
Matsura et al., *Brit. J. Cancer*, 66:1122–1130, 1992.
Matzura et al., *Comp. Appl. Biosci.*, 12:247–249, 1996.
McNeall et al., *Gene*, 76:81, 1989.
Melvin et al., *J. Virol. Methods*, 71:147–157, 2000.
Merlo et al., *Nat. Med.*, 1(7):686–92, 1995.
Michel et al., *J. Mol. Biol.*, 216:585–610, 1990.
Miksicek et al., *Cell*, 46:203, 1986.
Mordacq and Linzer, *Genes and Dev.*, 3:760, 1989.
Moreau et al., *Nucl. Acids Res.*, 9:6047, 1981.
Mori et al., *Cancer Res.*, 54:3396–3397, 1994.
Muesing et al., *Cell*, 48:691, 1987.
Nagayama et al., *J. Med.Virol.* 52:156–160, 1997.
Nerurkar et al., *J. Med. Virol.*, 56:123–127, 1998.
Ng et al., *Nuc. Acids Res.*, 17:601, 1989.
Nicolas and Rubenstein, In: *Vectors: A survey of molecular cloning vectors and their uses*, Rodriguez and Denhardt (eds.), Stoneham: Butterworth, pp. 493–513, 1988.
Nicolau and Sene, *Biochim. Biophys. Acta*, 721:185–190, 1982.
Nicolau et al., *Methods Enzymol.*, 149:157–176, 1987.
Nobri et al., *Nature*, 368:753–756, 1995.
Nomoto et al., *Gene*, 236(2):259–271, 1999.
Obrink, *BioEssays*, 13:227–233, 1991.
Odin and Obrink, *Exp. Cell Res.*, 171:1–15, 1987.
Ohara et al., *Proc. Natl. Acad. Sci. USA*, 86(15):5673–5677, 1989a.
Okamoto et al., *Proc. Nat'l Acad. Sci. USA*, 91:11045–11049, 1994.
Okamoto et al., *J. Gen. Virol.*, 78:737–745. 1997.
Ondek et al., *EMBO J.*, 6:1017,1987.
Orlow et al., *Cancer Res.*, 54:2848–2851, 1994.
Ornitz et al., *Mol. Cell. Biol.*, 7:3466, 1987.
Palmiter et al., *Nature*, 300:611, 1982.
Paskind et al., *Virology*, 67:242–248, 1975.
Pech et al., *Mol. Cell. Biol.*, 9:396, 1989.
Pelletier et al., *Nature*, 334(6180):320–325, 1988.
Perales et al., *Proc. Nat'l Acad. Sci.* 91:4086–4090, 1994.
Perez-Stable and Constantini, *Mol. Cell. Biol.*, 10:1116, 1990.
Pessoa et al., *Hepatol.*, 27:877–880, 1998.
Philip et al., *J. Biol. Chem.*, 268(22):16087–90, 1993.
Picard and Schaffner, *Nature*, 307:83, 1984.
Pinkert et al., *Genes and Dev.*, 1:268, 1987.
Pinto et al., *J. Virol.* 74:4505–4511, 2000.
Ponta et al., *Proc. Nat'l Acad. Sci. USA.*, 82:1020, 1985.
Porton et al., *Mol. Cell. Biol.*, 10:1076, 1990.

Potter et al., *Proc. Nat'l Acad. Sci. USA*, 81:7161–7165, 1984.
Queen and Baltimore, *Cell*, 35:741, 1983.
Quinn et al., *Mol. Cell. Biol.*, 9:4713, 1989.
Ragot et al., *Nature* 361:647–650, 1993.
Redondo et al., *Science*, 247:1225, 1990.
Reinhold-Hurek et al., *Nature*, 357:173–176, 1992.
Reisman and Rotter, *Mol. Cell. Biol*, 9:3571, 1989.
Resendez Jr. et al., *Mol. Cell. Biol.*, 8:4579, 1988.
Rich et al., "Development and analysis of recombinant adenoviruses for gene therapy of cystic fibrosis," *Hum. Gene Ther.*, 4(4):461–476, 1993.
Ridgeway, In: *Vectors: A survey of molecular cloning vectors and their uses*, Rodriguez R L, Denhardt D T, ed., Stoneham:Butterworth, pp. 467–492, 1988.
Rinaldo, Jr. et al., *Infect.Immun.* 14:660–666, 1976.
Rippe et al., *Mol. Cell Biol.*, 10:689–695, 1990.
Rittling et al., *Nucl. Acids Res.*, 17:1619, 1989.
Robertson et al., *Arch. Virol.*, 143:2493–2503, 1998.
Rosen et al., *Cell*, 41:813, 1988.
Rosenfeld et al., *Cell*, 68:143–155, 1992.
Rosenfeld et al., *Science*, 252:431–434, 1991.
Roux et al., *Proc. Nat'l Acad. Sci. USA*, 86:9079–9083, 1989.
Rowland-Jones, *J. Infect.* 38:67–70, 1999.
Sabin et al., *J. Acquir.Immune Defic.Syndr.* 19:546–547, 1998.
Sakai et al., *Genes and Dev.*, 2:1144, 1988.
Sambrook, Fritsch, Maniatis, In: *Molecular Cloning: A Laboratory Manual*, Vol. 1, Cold Spring Harbor Laboratory Press, Cold Spring Harbor, N.Y., Ch. 7,7.19–17.29, 1989.
Sarver et al., *Science*, 247:1222–1225, 1990.
Satake et al., *J. Virology*, 62:970, 1988.
Scanlon et al., Proc. Nat'l Acad. Sci. USA, 88:10591–10595, 1991.
Schaffner et al., *J. Mol. Biol*, 201:81, 1988.
Schmidt et al., *J. Med. Virol.*, 47:153–160. 1995.
Searle et al., *Mol. Cell. Biol.*, 5:1480, 1985.
Seipp et al., *J. Hepatol.*, 30:570–579, 1999.
Serrano et al., *Nature*, 366:704–707, 1993.
Serrano et al., *Science*, 267:249–252, 1995.
Sharp and Marciniak, *Cell*, 59:229, 1989.
Shaul and Ben-Levy, *EMBO J.*, 6:1913, 1987.
Sherman et al., *Mol. Cell. Biol.*, 9:50, 1989.
Shimizu, *J. Virol.*, 73:8411–8414, 1999.
Simons et al., *J. Virol.*, 70:6126–6135. 1996.
Simons et al., *Nature Med.*, 1:564–569, 1995.
Simons et al., *Proc.Natl.Acad.Sci.USA* 92:34013405.
Sleigh and Lockett, *J.EMBO*, 4:3831, 1985.
Solodin et al., *Biochemistry*, 34(41):13537–44, 1995.
Spalholz et al., *Cell*, 42:183, 1985.
Spandau and Lee, *J. Virology*, 62:427, 1988.
Spandidos and Wilkie, *EMBO J.*, 2:1193, 1983.
Stapleton et al., *J. Clin. Microbiol.*, 37:484–489, 1999.
Stephens and Hentschel, *Biochem. J.*, 248:1, 1987.
Stratford-Perricaudet and Perricaudet, "Gene transfer into animals: the promise of adenovirus," p. 51–61, In: *Human Gene Transfer*, Eds, O. Cohen-Haguenauer and M. Boiron, Editions John Libbey Eurotext, France, 1991.
Stratford-Perricaudet et al., *Hum. Gene Ther.*, 1:241–256, 1990.
Stuart et al., *Nature*, 317:828, 1985.
Sullivan and Peterlin, *Mol. Cell. Biol.*, 7:3315, 1987.
Swartzendruber and Lehman, *J. Cell. Physiology*, 85:179, 1975.
Tacke et al., *Hepatol.*, 26:1626–1633, 1997.
Takahashi et al., *Cancer Res.*, 52:734–736, 1992.
Takebe et al., *Mol. Cell. Biol.*, 8:466, 1988.
Tanaka et al., *J. Hepatol.*, 27:1110–1112, 1997.
Tavernier et al., *Nature*, 301:634, 1983.
Taylor and Kingston, *Mol. Cell. Biol.*, 10:165, 1990a.
Taylor and Kingston, *Mol. Cell. Biol.*, 10:176, 1990b.
Taylor et al., *J. Biol. Chem.*, 264:15160, 1989.
Taylor et al., *Science* 285:107–110, 1999.
Temin, In: *Gene Transfer*, Kucherlapati (ed.), New York: Plenum Press, pp. 149–188, 1986.
Templeton et al., *Nat. Biotechnol.*, 15(7):647–52, 1997.
Thierry et al., *Proc. Natl. Acad. Sci. USA*, 92(21):9742–6, 1995.
Thiesen et al., *J. Virology*, 62:614, 1988.
Thomas et al., *J.Infect.Dis.* 177:539–542, 1998.
Thomas et al. *J.Infect.Dis.* 177:539–542. 1998.
Toyoda et al., *J.Acquir.Immune Defic.Syndr.* 17:209–213, 1998.
Toyoda et al., *J.Med. Virol.* 60:34–38, 2000.
Treisman, *Cell*, 42:889, 1985.
Tronche et al., *Mol. Cell. Biol.*, 9:4759, 1989.
Trudel and Constantini, *Genes and Dev.*, 6:954, 1987.
Tsukamoto et al., *Nat. Genet.*, 9(3):243–8, 1995.
Tur-Kaspa et al., *Mol. Cell Biol.*, 6:716–718, 1986.
Tyndall et al., *Nuc. Acids. Res.*, 9:6231, 1981.
Umbas et al., *Cancer Res.*, 52:5104–5109, 1992.
Vannice and Levinson, *J. Virology*, 62:1305, 1988.
Vasseur et al., *Proc. Nat'l Acad. Sci. USA.*, 77:1068, 1980.
Wagner et al., *Proc. Nat'l Acad. Sci.* 87(9):3410–3414, 1990.
Walker et al. *Proc. Natl. Acad. Sci. USA*, 89(1):392–396, 1992.
Wang and Calame, *Cell*, 47:241, 1986.
Weber et al., *Cell*, 36:983, 1984.
Winoto and Baltimore, *Cell*, 59:649, 1989.
Wolf et al., *Comput. Appl. Biosci.*, 4(1):187–191, 1988.
Wong et al., *Gene*, 10:87–94, 1980.
Wu and Wu, *Adv. Drug Delivery Rev.*, 12:159–167, 1993.
Wu and Wu, *Biochem.*, 27:887–892,1988.
Wu and Wu, *J. Biol. Chem.*, 262:4429–4432, 1987.
Wu et al., *Biochem. Biophys. Res. Commun.*, 233(1):221–6, 1997.
Wu et al., *J. Med. Virol.*, 52:83–85. 1997.
Wünschmann & Stapleton, *J.Clin.Microbiol.* 38:3055–3060, 2000.
Wünschmann et al., *J. Virol.* 74:10055–10062, 2000
Xiang et al., *J. Virol.* 74:9125–9133, 2000.
Xiang et al., *J. Viral Hepat.*, 6:S16-S22, 1999.
Xiang et al., *J. Virol.*, 72:2738–2744. 1998.
Yanagi et al., *Proc. Nat'l. Acad. Sci.*, 94:8738–8743, 1997.
Yanagi et al., *Virology*, 244:161–172, 1998.
Yang et al., *Gene Ther.*, 4(9):950–60, 1997.
Yang et al., *Proc. Nat'l Acad. Sci USA*, 87:9568–9572, 1990.
Yeo et al., *Ann. Intern. Med.* 132:959–963, 2000.
Yutzey et al. *Mol. Cell. Biol*, 9:1397, 1989.
Zelenin et al., *FEBS Lett.*, 280:94–96, 1991.
Zhao-Emonet, et al., *Biochim. Biophys. Acta*, 1442(2–3):109–19, 1998.
Zhu et al., *Science*, 261(5118):209–11, 1993.

What is claimed is:

1. An isolated and purified DNA encoding an infectious GBV-C, wherein the DNA comprises a nucleic acid sequence encoding an amino acid sequence that is at least 99% identical to SEQ ID NO:2.

2. The nucleic acid molecule of claim 1, wherein the DNA is about 9.4 kilobases in length.

3. The nucleic acid molecule of claim 1, wherein the DNA comprises SEQ ID NO:1.

4. The nucleic acid molecule of claim 1, further comprising a heterologous nucleic acid sequence.

5. The nucleic acid molecule of claim 4, wherein the heterologous nucleic acid sequence encodes a polypeptide.

6. The nucleic acid molecule of claim 4, wherein the polypeptide is a mammalian polypeptide.

7. The nucleic acid molecule of claim 1, further comprising a heterologous promoter.

8. The nucleic acid molecule of claim 7, wherein the heterologous promoter promotes transcription in a prokaryote.

9. The nucleic acid molecule of claim 8, wherein the promoter is T7, T3, or Sp6.

10. The isolated and purified DNA of claim 1, wherein the DNA comprises a nucleic acid sequence encoding an amino acid sequence that is identical to SEQ ID NO:2.

11. The isolated and purified DNA of claim 1, wherein the DNA comprises 500 contiguous nucleotides that are identical or complementary to SEQ ID NO:1.

12. The isolated and purified DNA of claim 11, wherein the DNA comprises 1000 contiguous nucleotides that are identical or complementary to SEQ ID NO:1.

13. The isolated and purified DNA of claim 12, wherein the DNA comprises 2000 contiguous nucleotides that are identical or complementary to SEQ ID NO:1.

14. The isolated and purified DNA of claim 13, wherein the DNA comprises 5000 contiguous nucleotides that are identical or complementary to SEQ ID NO:1.

15. The isolated and purified DNA of claim 1, wherein the DNA comprises a 3' ntr or a 5' ntr of GBV-C.

16. The isolated and purified DNA of claim 15, wherein the DNA comprises a 3' ntr and a 5' ntr of GBV-C.

* * * * *

SEQUENCE LISTING

<160> NUMBER OF SEQ ID NOS: 2

<210> SEQ ID NO 1
<211> LENGTH: 9395
<212> TYPE: DNA
<213> ORGANISM: Hepatitis G virus

<400> SEQUENCE: 1
tgacgtgggg gggttgatcc cccccccccg gcactgggtg caagccccat aaaccgacgc 60
ctatctaagt agacgcaatg actcggcgcc gactcggcga ccggccaaaa ggtggtggat 120
gggtggtgac agggttggta ggtcgtaaat cccggtcatc ctggtagcca ctataggtgg 180
gtcttaagag aaggtcaaga ctcctcttgt gcctgcggcg agaccgcgca cggtccacag 240
gtgctggccc taccggtgtg aataagggcc cgacgtcagg ctcgtcgtta aaccgagccc 300
gtcacccacc tgggcaaacg acgcccacgt acggtccacg tcgcccttca atgtctctct 360
tgaccaatag gtttatccgg cgagttgaca aggaccagtg gggccggggg gttatgggga 420
aggaccccaa accctgccct tcccggtggg ccgggaaatg catggggcca cccagctccg 480
cggcggcctg cagccggggt agcccaagaa tccttcgggt gagggcgggt ggcatttctc 540
ttttctatac catcatggca gtccttctgc tccttctcgt ggttgaggcc ggggccattc 600
tggccccggc cacccacgct tgtcgagcga atgggcaata tttcctcaca aattgctgtg 660
ccccggaaga catcgggttc tgcctggaag gcggatgcct ggtggccctg gggtgcacgg 720
tttgcaccga ccgttgctgg ccactgtatc aggcgggttt ggctgtgcgg cctggcaagt 780
ccgcggccca gctcgttggg gaactgggga gcctgtacgg gcccttgtcg gtctcggctt 840
acgtagccgg gatcctgggt ctgggcgagg tttactccgg ggtcctgaca gttggtgttg 900
cgttgaggcg ccgggtctac ctgatgccca acctgaagtg tgcagtagaa tgtgacgtta 960
agtggggaag tgagttttgg agatggactg agcagttggc ctccaattac tggattttgg 1020
aatacctttg gaaagtccca tttgaatttt ggagaggagt gatgagcctg acccctctgt 1080
tggtttgggt ggccgcattg cttttgctgg agcaacggat tgtcatggtt ttcctgctgg 1140
tgacgatggc ggggatgttg caaggcgccc ccgcctccgt tttggggtcc cgcccctttg 1200
actacgggtt gaagtggcag tcatgctcct gcagggctaa cgggtcgcgt attcccactg 1260
gggagagggt gtgggatcga gggaatgtca cgctcttgtg tgactgcccc aacggcccct 1320
gggtttgggt cccggccttt tgccaggcgg ttgggtgggg cgaccccatc acccattgga 1380
gccacggaca aaaccagtgg cccctatcat gcccccaata tgtctatggg tctgtgtccg 1440
taacgtgcgt gtggggttcc gtgtcttggt ttgcctcgac cggcggtcgt gattcgaaga 1500
tcgatgtgtg gagtttggtg ccggttggat ctgccagctg caccatagcc gctctagggt 1560
catcggatcg cgacacggtg gttgagctct ccgagtgggg agtcccgtgc gtaacgtgta 1620
ttctggaccg tcggcctgct tcatgtggca cctgtgtgcg ggactgctgg cccgaaaccg 1680
ggtcggttag attccctttc catcggtgcg gcacggggcc tcggctgaca aaggacttgg 1740
aagctgtgcc cttcgtcaac aggacaactc ccttcaccat aaggggcccc ctgggcaacc 1800
aggggagagg caacccggtg cggtcgcccc tgggttttgg gtcctacacc atgaccaaga 1860
tccgggattc cctgcatttg gtgaaatgtc ccacaccagc catagagcct ccgactggaa 1920
cgttcgggtt cttccccgga gtcccgccca ttaacaactg catgccgcta ggcacggaag 1980
tgtctgaggc attgggcgga gctgggctta cgggggggtt ctacgagcct ctggttcgca 2040

-continued

```
ggtgttcgga gctgatggga cgccgaaatc cggtttgccc ggggtacgca tggctgtcct   2100
ctggtagacc tgacgggttc atacacgtcc aggggcacct gcaggaggtg gatgcgggca   2160
acttcatccc tcctccacgc tggttgctct tggattttgt atttgtcctg ctctatctga   2220
tgaagctggc tgaggcacgg ttggtcccgt tgatcttgct tctgctgtgg tggtgggtga   2280
accagttggc ggttctagga ctgccggctg tggacgctgc cgtggcgggt gaagtttttg   2340
cgggccctgc cttgtcatgg tgtttgggcc ttcccactgt cagtatgata ctaggtctag   2400
caaacctggt gttgtacttt cggtggatgg gccctcagcg cctcatgttc ctcgtgttgt   2460
ggaagctcgc tcggggagct ttcccgctgg cacttttgat ggggatttcg gcgacccgcg   2520
ggcgcacctc tgtgctcggg gccgagttct gcttcgatgt cacattcgag gtggacactt   2580
cggtgttggg ctgggtggtg gccagcgtgg tggcttgggc catagcgctc ctgagctcaa   2640
tgagcgcagg ggggtggaag cacaaggccg tgatctatag gacgtggtgt aaagggtacc   2700
aggctgtgcg ccagagggtg gtgcggagcc ccctcgggga ggggcgtcct accaagcttc   2760
tgacgttcgc ctggtgcttg gcctcataca tctggccgga tgctgtgatg atggtggtgg   2820
tggccttggt cctcctcttc ggcctgttcg acgcactgga ctgggccctg gaggagctcc   2880
tggtctcccg gccctcgtta cggcgactgg cacgggtggt tgagtgctgt gtgatggcgg   2940
gcgagaaggc caccaccatc cgactggtct ccaagatgtg cgcaagaggg gcctacctgt   3000
ttgaccacat gggctctttc tcgcgcgctg tcaaggagcg cttgttggaa tgggacgcgg   3060
ctttggagcc cttgtcattc actaggacgg actgtcgcat catcagagat gccgcgagga   3120
ccctgtcctg cggacagtgc gtcatgggtt tacccgtggt agcacggcgc ggtgatgagg   3180
ttctcatcgg cgtctttcag gatgtgaatc atttgcctcc cgggtttgtc ccgactgcac   3240
cagttgtcat ccgtcggtgc ggaaagggct tcctgggggt cacgaaggca gccttgacag   3300
gtagggatcc tgacttacat ccagggaacg tcatggtgtt ggggacggct acgtcacgaa   3360
gcatgggcac atgtctgaat ggcctgctgt tcacaacttt ccatggggct tcatcccgaa   3420
ccatcgccac gcccgtgggg gcccttaatc ccaggtggtg gtcagccagt gatgacgtca   3480
cggtgtaccc gcttccagat ggggcaactt cgttgacgcc ctgcacttgc caggcggagt   3540
cctgttgggt tattagatcc gacggggctt tgtgccatgg cttgagcaag ggggacaagg   3600
ttgagctgga tgtggccatg gaggtctctg acttccgtgg ttcgtctggt tcaccggtcc   3660
tttgcgacaa agggcacgca gtaagaatgc tcgtgtcagt gctccactct ggcggcaggg   3720
ttactgcggc gcgattcact aggccgtgga ctcaagtacc aacagatgcc aagactacca   3780
cagaaccccc tccggtgccg gcaaaaggag ttttcaagga ggccccgttg tttatgccta   3840
cgggggcggg aaagagcacc cgcgtaccgt tggagtacgg caacatgggc cacaaggtct   3900
tgatcttgaa cccgtcggta gctaccgtga gggccatggg cccatacatg gagcggctgg   3960
cggggaaaca ccccagtatt tactgtggcc atgacaccac tgctttcaca aggatcactg   4020
actcgcccct tacgtattcc acttacggaa ggtttttggc caaccctagg cagatgctga   4080
ggggtgtgtc ggtggtcatt tgtgacgagt gccacagtca tgactcaact gtgttgttgg   4140
gcattgggcg tgtcagggag ctggcgcgag gatgtggagt gcaattggtg ctctacgcca   4200
ctgccacccc tcccggatcc ccgatgaccc agcacccatc aatcattgag acaaaactgg   4260
acgtgggaga gatccccttc tatgggcatg gcatacctct tgagcggatg cggaccggaa   4320
ggcatctcgt attctgccac tccaaggctg agtgcgagcg cctggcgggc cagttttcgg   4380
```

-continued

```
ctagggggt aaatgccatc gcctattaca gggggaaaga cagttctatc atcaaagatg   4440
gagacctggt ggtgtgtgct acagacgcac tatccactgg gtacactggg aacttcgatt   4500
ctgtcaccga ttgtgggtta gtggtggagg aggtcgtcga ggtgaccctt gatcccacca   4560
ttaccatctc cctgcgcacg gtgcccgcgt cggctgaact gtcgatgcag cggcgaggac   4620
gcacgggtag gggcaggtct gggcgctact actacgcggg ggtcggcaag gcccctgctg   4680
gtgtggtgcg ctcaggtcct gtctggtcgg cggtggaagc cggtgtgacc tggtacggaa   4740
tggaacctga cctgacagca aacctactga gactttacga caactgccct tacaccgcag   4800
ccgtcgcagc tgacattggg gaagccgcgg tgttcttttc ggggcttgcc ccgttgagga   4860
tgcatcccga tgttagctgg gcaaaagttc gcggcgtcaa ctggcccttc ctggtgggtg   4920
ttcagcggac catgtgccgg gaaacactgt ctcccggccc atcggatgac ccccagtggg   4980
caggtctgaa gggcccgaat cctgtcccac tcctgctgag gtggggcaat gatttaccat   5040
ctaaagtggc cggccatcac atcgtggacg acctggtccg taggctcggg gtggcggagg   5100
gttacgtccg ctgcgatgcg ggacccatct tgatggtggg cctcgctatt gcgggggggca   5160
tgatctatgc gtcatacacc gggtctctcg tggtggttac agactgggat gtgaaggggg   5220
gtggcagccc cctttatcgg catggagacc aggccacgcc ccagccggtt gtgcaggtcc   5280
ccccggtaga ccatcggccg gggggagagt ctgcgccatc ggatgccaac acagtgacag   5340
atgcggtggc ggccatccag gtggattgcg attggtcagt catgaccctg tcgatcgggg   5400
aagtgctgtc cttggcccag gctaagacgg ccgaggccta cgcagctacc accaagtggc   5460
ttgctggctg ctacacgggg acgcgggccg tccccactgt ttcaattgtt gacaagctct   5520
tcgccggggg ctgggcggcg gtggtaggcc attgccacag tgtaatagct gcggcagtgg   5580
cggcctatgg ggcttctagg agccctccat tggctgctgc cgcttcctac ctcatggggt   5640
tgggcgtcgg aggcaacgcg caaacccgct tagcctccgc tctcctacta ggggccgctg   5700
ggaccgctct gggcacgcct gtcgtggggt taaccatggc gggcgcgttc atgggaagtg   5760
ctagcgtctc cccctccttg gtcaccattt tactgggggc cgtgggggc tgggagggcg   5820
tggtgaatgc ggctagcctt gtcttcgact ttatggcggg gaaactatca tcagaagatc   5880
tgtggtatgc catcccagtg ctaaccagtc cgggggcagg acttgcgggg atcgccctcg   5940
ggttggtgtt gtactcagct aacaactctg gcactaccac ttggttgaac cgtctgctga   6000
ctacattgcc aaggtcctca tgcatccctg acagttactt tcagcaggcc gattactgtg   6060
acaaggtctc agctgtgctc cgacgcttga gcctcactcg caccgtggtt gccctggtca   6120
acagggagcc taaggtggat gaggttcagg tggggtacgt ctgggacttg tgggagtgga   6180
tcatgcgtca agtgcgcatg gtgatggcca gacttcgggc cctctgcccc gtggtgtcat   6240
tacccttatg gcactgcggg gaggggtggt ccggagaatg gttgttggac ggccatgttg   6300
agagtcgttg tctttgtggt tgcgtgatca ccggtgatgt tttgaatggg caactcaaag   6360
atccagttta ctctaccaag ctgtgcaggc attattggat ggggacagtc cctgtgaaca   6420
tgctgggcta tggcgagacg tcgcctttgc tcgcctcaga caccccgaag gtggtaccat   6480
tcgggacgtc tgggtgggct gaggtggtgg tgacccctac ccacgttgtg atcaggcgaa   6540
catccgccta caaactgctg cgccagcaaa tcctgtcggc tgctgttgct gagccctatt   6600
acgtcgacgg cataccggtc tcatgggacg cggacgcgcg agcgcctgcc atggtctatg   6660
gccctgggca aagtgtcacc attgacgggg aacgctacac ccttccgcat caactgcggc   6720
ttaggaatgt ggcgccctct gaggtgtcat ccgaggtgtc cattgacatt gggacggaga   6780
```

-continued

```
ctgaagactc agaactgact gaggccgacc tgccgccggc ggctgcagcc cttcaggcta   6840
tcgagaatgc tgcgagaatt cttgaacctc acatagatgt catcatggaa gattgcagta   6900
caccctctct ttgtgggagt agccgagaga tgcctgtgtg gggagaagac ataccccgca   6960
ctccatcgcc agcacttatc tcggttactg agagcagccc agatgagaag accccgtcgg   7020
tgtcttcctc gcaggaggat accccgtctt ctgactcatt cgaggtcatc caagagtccg   7080
agacagccga aggggaggaa agcgtcttca acgtggctct ttccgtacta aaagccttgt   7140
ttccacagag cgatgccaca agaaagctta ccgttaagat gtcatgctgt gttgagaaga   7200
gcgtaacacg cttcttttca ttgggattga cggtcgctga cgtggcaagc ctgtgtgaga   7260
tggaaatcca gaaccataca gcctattgtg acaaggtgcg cactccgctt gaattgcagg   7320
ttgggtgctt ggtgggcaat gaacttacct ttgaatgtga caagtgtgag gctaggcaag   7380
agaccttggc ttccttctct tacatttggt ctggggtgcc actgacgagg gccactccgg   7440
ccaagccccc tgtggtgagg ccggttggct ccttgctggt ggccgacacc accaaggtgt   7500
atgtcaccaa cccggacaat gttgggagaa gagttgacaa ggttaccttc tggcgtgccc   7560
ctagggttca tgacaaattc ctcgtggact ccatagagcg cgctaagagg gcagctcaag   7620
cctgcctaag catgggttac acttatgagg aggcaataag gactgtaagg ccacatgctg   7680
ccatgggctg ggatctaag gtgtcggtca aggacctcgc caccccctgcg ggaagatgg   7740
ctgtccatga ccggctccag gagatacttg aagggacgcc agtcccttt actcttactg   7800
tgaaaaagga agtgttcttc aaagaccgaa aggaagagaa ggcccccgc ctcattgtgt   7860
tcccccccct ggacttccgg atagctgaaa agcttattct gggagaccct ggacgggtag   7920
ccaaggcggt gttgggggg gcctacgcct tccagtacac cccaaatcag cgaattaggg   7980
agatgctcaa actgtgggaa tcaaagaaga caccatgcgc catctgtgtg gacgccacat   8040
gcttcgacag tagcataact gaagaggacg tggcgctgga gacagagctt tatgccctgg   8100
cttcagacca tccagaatgg gtgcgtgccc tggggaaata ctatgcctct ggcacaatgg   8160
taacccccga gggggtgcca gtgggtgaga ggtattgtag atcctcaggg gtcttgacca   8220
ccagtgcgag caactgcttg acttgctata tcaaggtgaa agccgcctgt gagagggtgg   8280
ggctgaaaaa tgtctcgctc ctcatcgctg gcgatgactg tttgatcata tgcgaacggc   8340
ctgtgtgcga tcctagcgac gctttgggca gagccctggc gagctacggg tacgcatgcg   8400
agccttcgta tcatgcatca ctggacacgg ccccttctg ctccacttgg ctagctgagt   8460
gcaatgcaga tgggaaacgc catttcttcc tgaccacgga ctttcggagg cccctcgctc   8520
gcatgtcgag cgagtacagt gacccaatgg cttcggccat cggttacatc ctcctatacc   8580
cttggcatcc tatcacacgg tgggtcatca tccctcacgt gctcacctgc gcgtttaggg   8640
gtggtggcac accgtctgat cctgtgtggt gccaggtaca tggtaattac tacaagtttc   8700
cactggacaa actgcctaac atcatcgtgg ccctccacgg accagcagcg ttgagggtta   8760
ccgcagacac aactaagaca aaaatggagg ctggcaaggt gctgagcgac ctcaagctcc   8820
ctggcctagc agtccaccgg aagaaggccg gggcattgcg aacgcgtatg ctccggtcgc   8880
gcggttgggc tgagttggct agggggctgt tgtggcgtcc aggcctgcgg cttcccccctc   8940
cggagattgc tggtatcccc gggggtttcc ccctttcccc cccctatatg ggggtggttc   9000
atcaattgga tttcacaagc cagaggagtc gctggcggtg gttggggttc ttagccctgc   9060
tcatcgtagc cctcttcggg tgaactaaat tcatctgttg cggcaaggtc cggtgactga   9120
```

-continued

```
tcatcactgg aggaggttcc cgccctcccc gccccagggg tctccccgct gggtaaaaag   9180

ggcccggcct tgggaggcat ggtggttact aaccccctgg cagggtcaaa gcctgatggt   9240

gctaatgcac tgccacttcg gtggcgggtc gctaccttat agcgtaatcc gtgactacgg   9300

gctgctcgca gagccctccc cggatggggc acagtgcact gtgatctgaa ggggtgcacc   9360

ccggtaagag ctcggcccaa aggccgggtt ctact                              9395
```

<210> SEQ ID NO 2
<211> LENGTH: 2910
<212> TYPE: PRT
<213> ORGANISM: Hepatitis G virus

<400> SEQUENCE: 2

```
Met Ser Leu Leu Thr Asn Arg Phe Ile Arg Arg Val Asp Lys Asp Gln
  1               5                  10                  15

Trp Gly Pro Gly Val Met Gly Lys Asp Pro Lys Pro Cys Pro Ser Arg
             20                  25                  30

Trp Ala Gly Lys Cys Met Gly Pro Pro Ser Ser Ala Ala Cys Ser
         35                  40                  45

Arg Gly Ser Pro Arg Ile Leu Arg Val Arg Ala Gly Gly Ile Ser Leu
     50                  55                  60

Phe Tyr Thr Ile Met Ala Val Leu Leu Leu Leu Leu Val Val Glu Ala
 65                  70                  75                  80

Gly Ala Ile Leu Ala Pro Ala Thr His Ala Cys Arg Ala Asn Gly Gln
                 85                  90                  95

Tyr Phe Leu Thr Asn Cys Cys Ala Pro Glu Asp Ile Gly Phe Cys Leu
            100                 105                 110

Glu Gly Gly Cys Leu Val Ala Leu Gly Cys Thr Val Cys Thr Asp Arg
        115                 120                 125

Cys Trp Pro Leu Tyr Gln Ala Gly Leu Ala Val Arg Pro Gly Lys Ser
    130                 135                 140

Ala Ala Gln Leu Val Gly Glu Leu Gly Ser Leu Tyr Gly Pro Leu Ser
145                 150                 155                 160

Val Ser Ala Tyr Val Ala Gly Ile Leu Gly Leu Gly Glu Val Tyr Ser
                165                 170                 175

Gly Val Leu Thr Val Gly Val Ala Leu Arg Arg Arg Val Tyr Leu Met
            180                 185                 190

Pro Asn Leu Lys Cys Ala Val Glu Cys Asp Val Lys Trp Gly Ser Glu
        195                 200                 205

Phe Trp Arg Trp Thr Glu Gln Leu Ala Ser Asn Tyr Trp Ile Leu Glu
    210                 215                 220

Tyr Leu Trp Lys Val Pro Phe Glu Phe Trp Arg Gly Val Met Ser Leu
225                 230                 235                 240

Thr Pro Leu Leu Val Trp Val Ala Ala Leu Leu Leu Leu Glu Gln Arg
                245                 250                 255

Ile Val Met Val Phe Leu Leu Val Thr Met Ala Gly Met Leu Gln Gly
            260                 265                 270

Ala Pro Ala Ser Val Leu Gly Ser Arg Pro Phe Asp Tyr Gly Leu Lys
        275                 280                 285

Trp Gln Ser Cys Ser Cys Arg Ala Asn Gly Ser Arg Ile Pro Thr Gly
    290                 295                 300

Glu Arg Val Trp Asp Arg Gly Asn Val Thr Leu Leu Cys Asp Cys Pro
305                 310                 315                 320

Asn Gly Pro Trp Val Trp Val Pro Ala Phe Cys Gln Ala Val Gly Trp
```

-continued

```
                325                 330                 335

Gly Asp Pro Ile Thr His Trp Ser His Gly Gln Asn Gln Trp Pro Leu
            340                 345                 350

Ser Cys Pro Gln Tyr Val Tyr Gly Ser Val Ser Val Thr Cys Val Trp
        355                 360                 365

Gly Ser Val Ser Trp Phe Ala Ser Thr Gly Gly Arg Asp Ser Lys Ile
    370                 375                 380

Asp Val Trp Ser Leu Val Pro Val Gly Ser Ala Ser Cys Thr Ile Ala
385                 390                 395                 400

Ala Leu Gly Ser Ser Asp Arg Asp Thr Val Val Glu Leu Ser Glu Trp
                405                 410                 415

Gly Val Pro Cys Val Thr Cys Ile Leu Asp Arg Arg Pro Ala Ser Cys
            420                 425                 430

Gly Thr Cys Val Arg Asp Cys Trp Pro Glu Thr Gly Ser Val Arg Phe
        435                 440                 445

Pro Phe His Arg Cys Gly Thr Gly Pro Arg Leu Thr Lys Asp Leu Glu
    450                 455                 460

Ala Val Pro Phe Val Asn Arg Thr Thr Pro Phe Thr Ile Arg Gly Pro
465                 470                 475                 480

Leu Gly Asn Gln Gly Arg Gly Asn Pro Val Arg Ser Pro Leu Gly Phe
                485                 490                 495

Gly Ser Tyr Thr Met Thr Lys Ile Arg Asp Ser Leu His Leu Val Lys
            500                 505                 510

Cys Pro Thr Pro Ala Ile Glu Pro Pro Thr Gly Thr Phe Gly Phe Phe
        515                 520                 525

Pro Gly Val Pro Pro Ile Asn Asn Cys Met Pro Leu Gly Thr Glu Val
    530                 535                 540

Ser Glu Ala Leu Gly Gly Ala Gly Leu Thr Gly Gly Phe Tyr Glu Pro
545                 550                 555                 560

Leu Val Arg Arg Cys Ser Glu Leu Met Gly Arg Arg Asn Pro Val Cys
                565                 570                 575

Pro Gly Tyr Ala Trp Leu Ser Ser Gly Arg Pro Asp Gly Phe Ile His
            580                 585                 590

Val Gln Gly His Leu Gln Glu Val Asp Ala Gly Asn Phe Ile Pro Pro
        595                 600                 605

Pro Arg Trp Leu Leu Leu Asp Phe Val Phe Val Leu Leu Tyr Leu Met
    610                 615                 620

Lys Leu Ala Glu Ala Arg Leu Val Pro Leu Ile Leu Leu Leu Leu Trp
625                 630                 635                 640

Trp Trp Val Asn Gln Leu Ala Val Leu Gly Leu Pro Ala Val Asp Ala
                645                 650                 655

Ala Val Ala Gly Glu Val Phe Ala Gly Pro Ala Leu Ser Trp Cys Leu
            660                 665                 670

Gly Leu Pro Thr Val Ser Met Ile Leu Gly Leu Ala Asn Leu Val Leu
        675                 680                 685

Tyr Phe Arg Trp Met Gly Pro Gln Arg Leu Met Phe Leu Val Leu Trp
    690                 695                 700

Lys Leu Ala Arg Gly Ala Phe Pro Leu Ala Leu Leu Met Gly Ile Ser
705                 710                 715                 720

Ala Thr Arg Gly Arg Thr Ser Val Leu Gly Ala Glu Phe Cys Phe Asp
                725                 730                 735

Val Thr Phe Glu Val Asp Thr Ser Val Leu Gly Trp Val Val Ala Ser
            740                 745                 750
```

-continued

```
Val Val Ala Trp Ala Ile Ala Leu Leu Ser Ser Met Ser Ala Gly Gly
        755                 760                 765

Trp Lys His Lys Ala Val Ile Tyr Arg Thr Trp Cys Lys Gly Tyr Gln
    770                 775                 780

Ala Val Arg Gln Arg Val Val Arg Ser Pro Leu Gly Glu Gly Arg Pro
785                 790                 795                 800

Thr Lys Leu Leu Thr Phe Ala Trp Cys Leu Ala Ser Tyr Ile Trp Pro
                805                 810                 815

Asp Ala Val Met Met Val Val Val Ala Leu Val Leu Leu Phe Gly Leu
            820                 825                 830

Phe Asp Ala Leu Asp Trp Ala Leu Glu Glu Leu Leu Val Ser Arg Pro
        835                 840                 845

Ser Leu Arg Arg Leu Ala Arg Val Val Glu Cys Cys Val Met Ala Gly
    850                 855                 860

Glu Lys Ala Thr Thr Ile Arg Leu Val Ser Lys Met Cys Ala Arg Gly
865                 870                 875                 880

Ala Tyr Leu Phe Asp His Met Gly Ser Phe Ser Arg Ala Val Lys Glu
                885                 890                 895

Arg Leu Leu Glu Trp Asp Ala Ala Leu Glu Pro Leu Ser Phe Thr Arg
            900                 905                 910

Thr Asp Cys Arg Ile Ile Arg Asp Ala Ala Arg Thr Leu Ser Cys Gly
        915                 920                 925

Gln Cys Val Met Gly Leu Pro Val Val Ala Arg Arg Gly Asp Glu Val
    930                 935                 940

Leu Ile Gly Val Phe Gln Asp Val Asn His Leu Pro Pro Gly Phe Val
945                 950                 955                 960

Pro Thr Ala Pro Val Val Ile Arg Arg Cys Gly Lys Gly Phe Leu Gly
                965                 970                 975

Val Thr Lys Ala Ala Leu Thr Gly Arg Asp Pro Asp Leu His Pro Gly
            980                 985                 990

Asn Val Met Val Leu Gly Thr Ala Thr Ser Arg Ser Met Gly Thr Cys
        995                 1000                1005

Leu Asn Gly Leu Leu Phe Thr Thr Phe His Gly Ala Ser Ser Arg Thr
   1010                 1015                1020

Ile Ala Thr Pro Val Gly Ala Leu Asn Pro Arg Trp Trp Ser Ala Ser
1025                1030                1035                1040

Asp Asp Val Thr Val Tyr Pro Leu Pro Asp Gly Ala Thr Ser Leu Thr
               1045                1050                1055

Pro Cys Thr Cys Gln Ala Glu Ser Cys Trp Val Ile Arg Ser Asp Gly
           1060                1065                1070

Ala Leu Cys His Gly Leu Ser Lys Gly Asp Lys Val Glu Leu Asp Val
       1075                1080                1085

Ala Met Glu Val Ser Asp Phe Arg Gly Ser Ser Gly Ser Pro Val Leu
   1090                 1095                1100

Cys Asp Lys Gly His Ala Val Arg Met Leu Val Ser Val Leu His Ser
1105                1110                1115                1120

Gly Gly Arg Val Thr Ala Ala Arg Phe Thr Arg Pro Trp Thr Gln Val
               1125                1130                1135

Pro Thr Asp Ala Lys Thr Thr Thr Glu Pro Pro Pro Val Pro Ala Lys
           1140                1145                1150

Gly Val Phe Lys Glu Ala Pro Leu Phe Met Pro Thr Gly Ala Gly Lys
       1155                1160                1165
```

-continued

```
Ser Thr Arg Val Pro Leu Glu Tyr Gly Asn Met Gly His Lys Val Leu
   1170                1175                1180

Ile Leu Asn Pro Ser Val Ala Thr Val Arg Ala Met Gly Pro Tyr Met
1185                1190                1195                1200

Glu Arg Leu Ala Gly Lys His Pro Ser Ile Tyr Cys Gly His Asp Thr
               1205                1210                1215

Thr Ala Phe Thr Arg Ile Thr Asp Ser Pro Leu Thr Tyr Ser Thr Tyr
           1220                1225                1230

Gly Arg Phe Leu Ala Asn Pro Arg Gln Met Leu Arg Gly Val Ser Val
       1235                1240                1245

Val Ile Cys Asp Glu Cys His Ser His Asp Ser Thr Val Leu Leu Gly
   1250                1255                1260

Ile Gly Arg Val Arg Glu Leu Ala Arg Gly Cys Gly Val Gln Leu Val
1265                1270                1275                1280

Leu Tyr Ala Thr Ala Thr Pro Pro Gly Ser Pro Met Thr Gln His Pro
               1285                1290                1295

Ser Ile Ile Glu Thr Lys Leu Asp Val Gly Glu Ile Pro Phe Tyr Gly
           1300                1305                1310

His Gly Ile Pro Leu Glu Arg Met Arg Thr Gly Arg His Leu Val Phe
       1315                1320                1325

Cys His Ser Lys Ala Glu Cys Glu Arg Leu Ala Gly Gln Phe Ser Ala
   1330                1335                1340

Arg Gly Val Asn Ala Ile Ala Tyr Tyr Arg Gly Lys Asp Ser Ser Ile
1345                1350                1355                1360

Ile Lys Asp Gly Asp Leu Val Val Cys Ala Thr Asp Ala Leu Ser Thr
               1365                1370                1375

Gly Tyr Thr Gly Asn Phe Asp Ser Val Thr Asp Cys Gly Leu Val Val
           1380                1385                1390

Glu Glu Val Val Glu Val Thr Leu Asp Pro Thr Ile Thr Ile Ser Leu
       1395                1400                1405

Arg Thr Val Pro Ala Ser Ala Glu Leu Ser Met Gln Arg Arg Gly Arg
   1410                1415                1420

Thr Gly Arg Gly Arg Ser Gly Arg Tyr Tyr Tyr Ala Gly Val Gly Lys
1425                1430                1435                1440

Ala Pro Ala Gly Val Val Arg Ser Gly Pro Val Trp Ser Ala Val Glu
               1445                1450                1455

Ala Gly Val Thr Trp Tyr Gly Met Glu Pro Asp Leu Thr Ala Asn Leu
           1460                1465                1470

Leu Arg Leu Tyr Asp Asn Cys Pro Tyr Thr Ala Ala Val Ala Ala Asp
       1475                1480                1485

Ile Gly Glu Ala Ala Val Phe Phe Ser Gly Leu Ala Pro Leu Arg Met
   1490                1495                1500

His Pro Asp Val Ser Trp Ala Lys Val Arg Gly Val Asn Trp Pro Phe
1505                1510                1515                1520

Leu Val Gly Val Gln Arg Thr Met Cys Arg Glu Thr Leu Ser Pro Gly
               1525                1530                1535

Pro Ser Asp Asp Pro Gln Trp Ala Gly Leu Lys Gly Pro Asn Pro Val
           1540                1545                1550

Pro Leu Leu Leu Arg Trp Gly Asn Asp Leu Pro Ser Lys Val Ala Gly
       1555                1560                1565

His His Ile Val Asp Asp Leu Val Arg Arg Leu Gly Val Ala Glu Gly
   1570                1575                1580

Tyr Val Arg Cys Asp Ala Gly Pro Ile Leu Met Val Gly Leu Ala Ile
```

-continued

```
1585                1590                1595                1600

Ala Gly Gly Met Ile Tyr Ala Ser Tyr Thr Gly Ser Leu Val Val Val
                1605                1610                1615

Thr Asp Trp Asp Val Lys Gly Gly Gly Ser Pro Leu Tyr Arg His Gly
            1620                1625                1630

Asp Gln Ala Thr Pro Gln Pro Val Val Gln Val Pro Pro Val Asp His
        1635                1640                1645

Arg Pro Gly Gly Glu Ser Ala Pro Ser Asp Ala Asn Thr Val Thr Asp
    1650                1655                1660

Ala Val Ala Ala Ile Gln Val Asp Cys Asp Trp Ser Val Met Thr Leu
1665                1670                1675                1680

Ser Ile Gly Glu Val Leu Ser Leu Ala Gln Ala Lys Thr Ala Glu Ala
                1685                1690                1695

Tyr Ala Ala Thr Thr Lys Trp Leu Ala Gly Cys Tyr Thr Gly Thr Arg
            1700                1705                1710

Ala Val Pro Thr Val Ser Ile Val Asp Lys Leu Phe Ala Gly Gly Trp
        1715                1720                1725

Ala Ala Val Val Gly His Cys His Ser Val Ile Ala Ala Ala Val Ala
    1730                1735                1740

Ala Tyr Gly Ala Ser Arg Ser Pro Pro Leu Ala Ala Ala Ala Ser Tyr
1745                1750                1755                1760

Leu Met Gly Leu Gly Val Gly Gly Asn Ala Gln Thr Arg Leu Ala Ser
                1765                1770                1775

Ala Leu Leu Leu Gly Ala Ala Gly Thr Ala Leu Gly Thr Pro Val Val
            1780                1785                1790

Gly Leu Thr Met Ala Gly Ala Phe Met Gly Ser Ala Ser Val Ser Pro
        1795                1800                1805

Ser Leu Val Thr Ile Leu Leu Gly Ala Val Gly Gly Trp Glu Gly Val
    1810                1815                1820

Val Asn Ala Ala Ser Leu Val Phe Asp Phe Met Ala Gly Lys Leu Ser
1825                1830                1835                1840

Ser Glu Asp Leu Trp Tyr Ala Ile Pro Val Leu Thr Ser Pro Gly Ala
                1845                1850                1855

Gly Leu Ala Gly Ile Ala Leu Gly Leu Val Leu Tyr Ser Ala Asn Asn
            1860                1865                1870

Ser Gly Thr Thr Thr Trp Leu Asn Arg Leu Leu Thr Thr Leu Pro Arg
        1875                1880                1885

Ser Ser Cys Ile Pro Asp Ser Tyr Phe Gln Gln Ala Asp Tyr Cys Asp
    1890                1895                1900

Lys Val Ser Ala Val Leu Arg Arg Leu Ser Leu Thr Arg Thr Val Val
1905                1910                1915                1920

Ala Leu Val Asn Arg Glu Pro Lys Val Asp Glu Val Gln Val Gly Tyr
                1925                1930                1935

Val Trp Asp Leu Trp Glu Trp Ile Met Arg Gln Val Arg Met Val Met
            1940                1945                1950

Ala Arg Leu Arg Ala Leu Cys Pro Val Val Ser Leu Pro Leu Trp His
        1955                1960                1965

Cys Gly Glu Gly Trp Ser Gly Glu Trp Leu Leu Asp Gly His Val Glu
    1970                1975                1980

Ser Arg Cys Leu Cys Gly Cys Val Ile Thr Gly Asp Val Leu Asn Gly
1985                1990                1995                2000

Gln Leu Lys Asp Pro Val Tyr Ser Thr Lys Leu Cys Arg His Tyr Trp
                2005                2010                2015
```

-continued

```
Met Gly Thr Val Pro Val Asn Met Leu Gly Tyr Gly Glu Thr Ser Pro
            2020                2025                2030

Leu Leu Ala Ser Asp Thr Pro Lys Val Val Pro Phe Gly Thr Ser Gly
        2035                2040                2045

Trp Ala Glu Val Val Val Thr Pro Thr His Val Val Ile Arg Arg Thr
    2050                2055                2060

Ser Ala Tyr Lys Leu Leu Arg Gln Gln Ile Leu Ser Ala Ala Val Ala
2065                2070                2075                2080

Glu Pro Tyr Tyr Val Asp Gly Ile Pro Val Ser Trp Asp Ala Asp Ala
                2085                2090                2095

Arg Ala Pro Ala Met Val Tyr Gly Pro Gly Gln Ser Val Thr Ile Asp
            2100                2105                2110

Gly Glu Arg Tyr Thr Leu Pro His Gln Leu Arg Leu Arg Asn Val Ala
        2115                2120                2125

Pro Ser Glu Val Ser Ser Glu Val Ser Ile Asp Ile Gly Thr Glu Thr
    2130                2135                2140

Glu Asp Ser Glu Leu Thr Glu Ala Asp Leu Pro Pro Ala Ala Ala Ala
2145                2150                2155                2160

Leu Gln Ala Ile Glu Asn Ala Ala Arg Ile Leu Glu Pro His Ile Asp
                2165                2170                2175

Val Ile Met Glu Asp Cys Ser Thr Pro Ser Leu Cys Gly Ser Ser Arg
            2180                2185                2190

Glu Met Pro Val Trp Gly Glu Asp Ile Pro Arg Thr Pro Ser Pro Ala
        2195                2200                2205

Leu Ile Ser Val Thr Glu Ser Ser Pro Asp Glu Lys Thr Pro Ser Val
    2210                2215                2220

Ser Ser Ser Gln Glu Asp Thr Pro Ser Ser Asp Ser Phe Glu Val Ile
2225                2230                2235                2240

Gln Glu Ser Glu Thr Ala Glu Gly Glu Glu Ser Val Phe Asn Val Ala
                2245                2250                2255

Leu Ser Val Leu Lys Ala Leu Phe Pro Gln Ser Asp Ala Thr Arg Lys
            2260                2265                2270

Leu Thr Val Lys Met Ser Cys Cys Val Glu Lys Ser Val Thr Arg Phe
        2275                2280                2285

Phe Ser Leu Gly Leu Thr Val Ala Asp Val Ala Ser Leu Cys Glu Met
    2290                2295                2300

Glu Ile Gln Asn His Thr Ala Tyr Cys Asp Lys Val Arg Thr Pro Leu
2305                2310                2315                2320

Glu Leu Gln Val Gly Cys Leu Val Gly Asn Glu Leu Thr Phe Glu Cys
                2325                2330                2335

Asp Lys Cys Glu Ala Arg Gln Glu Thr Leu Ala Ser Phe Ser Tyr Ile
            2340                2345                2350

Trp Ser Gly Val Pro Leu Thr Arg Ala Thr Pro Ala Lys Pro Pro Val
        2355                2360                2365

Val Arg Pro Val Gly Ser Leu Leu Val Ala Asp Thr Thr Lys Val Tyr
    2370                2375                2380

Val Thr Asn Pro Asp Asn Val Gly Arg Arg Val Asp Lys Val Thr Phe
2385                2390                2395                2400

Trp Arg Ala Pro Arg Val His Asp Lys Phe Leu Val Asp Ser Ile Glu
                2405                2410                2415

Arg Ala Lys Arg Ala Ala Gln Ala Cys Leu Ser Met Gly Tyr Thr Tyr
            2420                2425                2430
```

-continued

```
Glu Glu Ala Ile Arg Thr Val Arg Pro His Ala Ala Met Gly Trp Gly
       2435                2440                2445

Ser Lys Val Ser Val Lys Asp Leu Ala Thr Pro Ala Gly Lys Met Ala
   2450                2455                2460

Val His Asp Arg Leu Gln Glu Ile Leu Glu Gly Thr Pro Val Pro Phe
2465                2470                2475                2480

Thr Leu Thr Val Lys Lys Glu Val Phe Phe Lys Asp Arg Lys Glu Glu
                2485                2490                2495

Lys Ala Pro Arg Leu Ile Val Phe Pro Pro Leu Asp Phe Arg Ile Ala
            2500                2505                2510

Glu Lys Leu Ile Leu Gly Asp Pro Gly Arg Val Ala Lys Ala Val Leu
       2515                2520                2525

Gly Gly Ala Tyr Ala Phe Gln Tyr Thr Pro Asn Gln Arg Ile Arg Glu
   2530                2535                2540

Met Leu Lys Leu Trp Glu Ser Lys Lys Thr Pro Cys Ala Ile Cys Val
2545                2550                2555                2560

Asp Ala Thr Cys Phe Asp Ser Ser Ile Thr Glu Glu Asp Val Ala Leu
                2565                2570                2575

Glu Thr Glu Leu Tyr Ala Leu Ala Ser Asp His Pro Glu Trp Val Arg
            2580                2585                2590

Ala Leu Gly Lys Tyr Tyr Ala Ser Gly Thr Met Val Thr Pro Glu Gly
       2595                2600                2605

Val Pro Val Gly Glu Arg Tyr Cys Arg Ser Ser Gly Val Leu Thr Thr
   2610                2615                2620

Ser Ala Ser Asn Cys Leu Thr Cys Tyr Ile Lys Val Lys Ala Ala Cys
2625                2630                2635                2640

Glu Arg Val Gly Leu Lys Asn Val Ser Leu Leu Ile Ala Gly Asp Asp
                2645                2650                2655

Cys Leu Ile Ile Cys Glu Arg Pro Val Cys Asp Pro Ser Asp Ala Leu
            2660                2665                2670

Gly Arg Ala Leu Ala Ser Tyr Gly Tyr Ala Cys Glu Pro Ser Tyr His
       2675                2680                2685

Ala Ser Leu Asp Thr Ala Pro Phe Cys Ser Thr Trp Leu Ala Glu Cys
   2690                2695                2700

Asn Ala Asp Gly Lys Arg His Phe Phe Leu Thr Thr Asp Phe Arg Arg
2705                2710                2715                2720

Pro Leu Ala Arg Met Ser Ser Glu Tyr Ser Asp Pro Met Ala Ser Ala
                2725                2730                2735

Ile Gly Tyr Ile Leu Leu Tyr Pro Trp His Pro Ile Thr Arg Trp Val
            2740                2745                2750

Ile Ile Pro His Val Leu Thr Cys Ala Phe Arg Gly Gly Gly Thr Pro
       2755                2760                2765

Ser Asp Pro Val Trp Cys Gln Val His Gly Asn Tyr Tyr Lys Phe Pro
   2770                2775                2780

Leu Asp Lys Leu Pro Asn Ile Ile Val Ala Leu His Gly Pro Ala Ala
2785                2790                2795                2800

Leu Arg Val Thr Ala Asp Thr Thr Lys Thr Lys Met Glu Ala Gly Lys
                2805                2810                2815

Val Leu Ser Asp Leu Lys Leu Pro Gly Leu Ala Val His Arg Lys Lys
            2820                2825                2830

Ala Gly Ala Leu Arg Thr Arg Met Leu Arg Ser Arg Gly Trp Ala Glu
       2835                2840                2845

Leu Ala Arg Gly Leu Leu Trp Arg Pro Gly Leu Arg Leu Pro Pro Pro
```

-continued

```
  2850                2855                2860

Glu Ile Ala Gly Ile Pro Gly Gly Phe Pro Leu Ser Pro Pro Tyr Met
2865                2870                2875                2880

Gly Val Val His Gln Leu Asp Phe Thr Ser Gln Arg Ser Arg Trp Arg
                2885                2890                2895

Trp Leu Gly Phe Leu Ala Leu Leu Ile Val Ala Leu Phe Gly
            2900                2905                2910
```